United States Patent
Pan et al.

(10) Patent No.: US 9,373,807 B2
(45) Date of Patent: Jun. 21, 2016

(54) RADIATIVE FIBERS

(75) Inventors: Junyou Pan, Frankfurt am Main (DE); Herwig Buchholz, Frankfurt am Main (DE); Ewald Aydt, Rossdorf (DE)

(73) Assignee: Merck Patent GmbH, Darmstadt (DE)

( * ) Notice: Subject to any disclaimer, the term of this patent is extended or adjusted under 35 U.S.C. 154(b) by 225 days.

(21) Appl. No.: 13/634,078

(22) PCT Filed: Feb. 15, 2011

(86) PCT No.: PCT/EP2011/000705
§ 371 (c)(1),
(2), (4) Date: Sep. 11, 2012

(87) PCT Pub. No.: WO2011/110275
PCT Pub. Date: Sep. 15, 2011

(65) Prior Publication Data
US 2013/0006118 A1    Jan. 3, 2013

(30) Foreign Application Priority Data
Mar. 11, 2010 (EP) .................................... 10002557

(51) Int. Cl.
*H01L 51/54* (2006.01)
*H05B 33/14* (2006.01)
*H01L 51/50* (2006.01)
(Continued)

(52) U.S. Cl.
CPC .......... *H01L 51/5032* (2013.01); *A61N 5/0616* (2013.01); *C09B 69/109* (2013.01); *A61N 5/062* (2013.01); *A61N 5/0621* (2013.01); *A61N 2005/063* (2013.01); *A61N 2005/0645* (2013.01)

(58) Field of Classification Search
CPC . H01L 27/304; H01L 51/447; H01L 51/5203; H01L 51/5221; H01L 51/5287; H01L 51/5237; H01L 51/5032; A61B 5/0084; A61B 19/5202; A61B 5/6874; A61B 5/0059; H01G 9/2068; H01G 9/2086; H01G 9/2095; H05B 33/11; H05B 33/14; D02G 3/441
USPC .................................................. 313/498–512
See application file for complete search history.

(56) References Cited

U.S. PATENT DOCUMENTS 3,792,308 A * 2/1974 Ota ................................ 315/150
5,485,355 A * 1/1996 Voskoboinik et al. .......... 362/84
5,753,381 A * 5/1998 Feldman et al. .............. 428/696
(Continued)

FOREIGN PATENT DOCUMENTS

JP    01-277824 A    11/1989
JP    08-190801 A    7/1996
(Continued)

OTHER PUBLICATIONS

U.S. Appl. No. 13/634,101.
(Continued)

*Primary Examiner* — Donald Raleigh
*Assistant Examiner* — Kevin Quarterman
(74) *Attorney, Agent, or Firm* — Drinker Biddle & Reath LLP

(57) ABSTRACT

The present invention relates inter alia to light emitting fibers for the application in general lighting, display backlit, information display, and for treatment and/or prophylaxis and/or diagnosis of diseases and/or cosmetic conditions. The fibers can be used for the preparation of any kind of canvas and light emitting devices.

24 Claims, 6 Drawing Sheets a)

b)

(51) Int. Cl.
 *A61N 5/06* (2006.01)
 *C09B 69/10* (2006.01)

(56) References Cited

U.S. PATENT DOCUMENTS

| | | | |
|---|---|---|---|
| 5,869,930 A * | 2/1999 | Baumberg et al. | 313/506 |
| 6,538,375 B1 | 3/2003 | Duggal et al. | |
| 8,013,527 B2 * | 9/2011 | Son et al. | 313/512 |
| 8,040,036 B2 * | 10/2011 | Choi et al. | 313/483 |
| 8,324,799 B2 * | 12/2012 | Yamamoto | 313/504 |
| 8,558,105 B2 * | 10/2013 | Carroll et al. | 136/256 |
| 2003/0099858 A1 | 5/2003 | Duggal et al. | |
| 2004/0111132 A1 | 6/2004 | Shenderova et al. | |
| 2007/0281386 A1 | 12/2007 | Park | |
| 2008/0217587 A1 * | 9/2008 | Gaudiana et al. | 252/501.1 |
| 2010/0016844 A1 * | 1/2010 | Patel, Jr. | 606/15 |
| 2010/0079846 A1 * | 4/2010 | Mazurkiewicz et al. | 359/275 |
| 2011/0263920 A1 * | 10/2011 | Bourke et al. | 600/1 |
| 2013/0006118 A1 * | 1/2013 | Pan et al. | 600/476 |
| 2013/0006119 A1 * | 1/2013 | Pan et al. | 600/476 |

FOREIGN PATENT DOCUMENTS

| | | |
|---|---|---|
| JP | 2000-109824 A | 4/2000 |
| JP | 2008-517265 A | 5/2008 |
| JP | 2009507246 A | 2/2009 |
| JP | 2009-266745 A | 11/2009 |
| WO | WO-96/37001 A1 | 11/1996 |
| WO | WO-2004052238 A2 | 6/2004 |
| WO | WO-2006/040717 A1 | 4/2006 |
| WO | WO-2006101735 A1 | 9/2006 |
| WO | WO-2007002989 A1 | 1/2007 |
| WO | WO-2007129827 A1 | 11/2007 |

OTHER PUBLICATIONS

International Search Report for PCT/EP2011/000707 mailed Jun. 6, 2011.

Written Opinion of the International Searching Authority for PCT/EP2011/000707.

International Search Report for PCT/EP2011/000705 Sep. 28, 2011.

* cited by examiner

RADIATIVE FIBERS

CROSS-REFERENCE TO RELATED APPLICATIONS

This application is a national stage application (under 35 U.S.C. §371) of PCT/EP2011/000705, filed Feb. 15, 2011, which claims benefit of European application 10002557.6, filed Mar. 11, 2010.

BACKGROUND OF THE INVENTION

The present invention relates inter alia to radiative fibers, their preparation and use in, e.g., lighting, display technologies, medical and cosmetic applications.

Organic electroluminescent devices, in particular organic light emitting diodes (OLEDs), have drawn much attention since two decades, because they have advantages over their inorganic counterparts in that they are, e.g., intrinsically flexible, and can be easily coated on large area by cheap methods, such as printing technologies like ink jet printing or screen printing. Therefore, organic electroluminescent devices are very promising devices for large area applications like general lighting and display technologies. Actually, OLED can already be found in marketed products such as the display of cell phones or digital cameras.

Another filed of application for organic electroluminescent devices is phototherapy. Phototherapy (also called light therapy) can be employed in a wide range of diseases and/or cosmetic (also called aesthetic) conditions. The therapy using light, either from LED or laser, is already being used to treat wounds, injuries, neck pain, osteoarthritis, the side effects of chemotherapy and radiotherapy, for instance.

Often the borders between therapeutic and cosmetic applications are vague and depend on individual circumstances and the assessment of a physician. Often therapeutic conditions are associated with cosmetic consideration. The treatment or prophylaxis of acne, for example, may have both therapeutic and cosmetic components, depending on the degree of the condition. The same accounts for psoriasis, atopic dermatitis and other diseases and/or conditions. Many diseases and conditions are associated with apparent implications which are often represented by a change in the visibility of a subject's skin, for instance. These cosmetic or aesthetic changes can often lead to psychological modifications resulting, at least in part, in serious diseases.

Some conditions or diseases may have an emphasis on cosmetic components, even if therapeutic elements may also play a role. Some of these are selected from anti-ageing, anti-wrinkle, the prevention and/or therapy of acne and vitiligo.

Many diagnostic tools or devices also often require light sources, e.g., in order to determine blood characteristics such as bilirubin, oxygen, or CO. In both cosmetics and medicine the skin is the main target to be radiated, but other targets of the human or animal body can also be accessed by phototherapy. These targets include, but are not limited to, the eye, wounds, nails, and internal parts of the body. Light can also be used in order to facilitate or support disinfection of wounds, surfaces of more or less solid objects, liquids, and beverages, for example. More or less solid surfaces as used herein include any surface with plasticity or elasticity which is not a liquid. Many objects fall in this category and comprise, e.g., nutrition, cuterly, instruments for use in hospitals and surgery and any other object that requires a disinfection. Even wounds of humans and animals can also be subsumed under this definition.

One of the primary effects of phototherapy is the stimulation of metabolism in the mitochondria. Certain wavelengths of light stimulate cytochrome c oxidase, an enzyme which is responsible for the production of the essential cellular energy in the form of adenosine triphosphate (ATP). ATP is required for cellular energy transfer in order to drive thermodynamically unfavoured biochemical reactions and as cellular energy storage. ATP can also act as signal molecule in order to modulate other biochemical molecules (e.g. reactive oxygen species and nitric oxide) that lead to ageing and cell death (oxidative stress). After phototherapy, the cells show an increased metabolism, they communicate better and they survive stressful conditions in a better way.

This principle can be applied for many medicinal therapeutic and cosmetic applications, such as wound healing, connective tissue repair, tissue repair, prevention of tissue death, relief of inflammation, pain, acute injuries, chronic diseases, metabolic disorders, neurogenic pain and seasonal effect disorders.

Another area of the application of light is the treatment of various cancers. In cancer therapy photodynamic therapy (PDT) plays an important role. In PDT light may be used in conjunction with a pharmaceutical. These therapies can be used to treat a variety of skin and internal diseases. In PDT, a light-sensitive therapeutic agent known as a photopharmaceutical is supplied externally or internally to an area of the body which is to be treated. That area is then exposed to light of a suitable frequency and intensity to activate the photopharmaceutical. A variety of photopharmaceutical agents are currently available. For example there are topical agents such as 5-aminolevulinic acid hydrochloride (Crawford Pharmaceuticals), methylaminolevulinic acid (Metfix®, Photocure). There are also injectable drugs used primarily for internal malignancies, including Photofin® (from Axcan) and Foscan® (from Biolitech Ltd). Often, the drug is applied in a non-active form that is metabolised to a light-sensitive photopharmaceutical.

In photodynamic therapy, the primary technique for supplying light to the photopharmaceutical is to project light of a suitable wavelength from standalone light sources such as lasers or filtered arc lamps. These sources are cumbersome and expensive, and are therefore only suitable for use in hospitals. This leads to inconveniences for the patient, and high cost for the treatment. High light irradiances are needed in order to treat an acceptable number of patients per day (for the treatment to be cost effective) and to avoid unduly inconveniencing the patient.

WO 98/46130 and U.S. Pat. No. 6,096,066 disclose arrays of LEDs for the use in photodynamic therapy. The small LED sources taught therein result in uneven light incident on the patient. Fabrication of arrays is complicated because of the large number of connections required. The devices shown therein are designed for hospital treatment.

GB 2360461 discloses a flexible garment which uses a conventional photodynamic therapy light source to produce light which is then transmitted through optical fibres. As such light sources are heavy, the device is not ambulatory and is limited to hospital use.

U.S. Pat. No. 5,698,866 discloses a light source using over-driven inorganic LEDs. A heat-sinking mechanism is required, and the device is suitable only for hospital treatment.

WO 93/21842 disclose light sources using inorganic LEDs. Although transportable, the device is not suitable for ambulatory use by a patient at home and clinical treatment is envisaged.

An essential prerequisite for the wide application of light in the fields mentioned above is the device. The commercial available systems nowadays are mostly based on lasers. However, theses systems are hospital based, i.e. stationary devices. In order to reduce costs and to increase convenience as well as compliance a portable home-use technology is required. In fact, some research has been devoted in this direction.

Organic electroluminescent devices have many advantages over their inorganic counterpart (light emitting diodes—LEDs) in that they are intrinsically flexible, and can be coated on large area by, for example, printing technologies, such as ink jet printing and screen printing. Furthermore they allow more homogenous irradiation as compared to LEDs.

Rochester et al. disclosed in GB 24082092 a flexible medical light source such as an OLED comprising flexible light emitting diodes on a flexible substrate and resulting diagnostic devices directed to monitor blood characteristics (e.g. levels of CO, oxygen, or bilirubin) and phototherapeutic devices for the treatment of ailments.

Vogle Klaus and Kallert Heiko disclosed in EP 018180773 a device for the treatment of skin. The device comprises an potentially flexible organic light emitting diode (OLED) as light source. The device can be integrated in clothes or plaster.

Attili et al. (Br. J. Dermatol. 161(1), 170-173. 2009) published a clinical open pilot study of ambulatory photodynamic therapy (PDT) using a wearable low-irradiance OLEDs in the treatment of nonmelanoma skin cancer, suggesting that OLED-PDT is less painful than conventional PDT with the added advantage of being lightweight, and therefore has the potential for more convenient PDT at home.

Samuel et al. disclosed in EP 1444008B15 an ambulatory device for the use in a therapeutic and/or cosmetic treatment, the device comprises an OLEDs and poly(p-phenylene vinylene) (PPV) is used as an example.

EP 1444008 discloses devices comprising OLEDs for the treatment of photodynamic therapy.

All of these devices used for the treatment are based on organic light emitting diodes (OLEDs).

However, state-of-the-art OLEDs use active metals, such as Ba and Ca, as cathode, and therefore they require excellent encapsulation to ensure an acceptable lifetime related to both storage and operation. For flat large area devices, appropriate encapsulation is even more critical, because defects in even small areas will lead to a total failure of the whole device. Further, in order to get good performance, particularly with respect to lifetime, OLEDs are usually designed to have a multilayer structure, wherein the different functions are optimized in individual layers. The manufacturing process of such devices requires, however, a more sophisticated manufacturing infrastructure, leading to high production costs and probably also low yields. It is highly desired to find a device, which is flexible and less insensitive to local damages.

Flexible fiber electroluminescent light sources are known in the art, as set forth, for example in U.S. Pat. No. 6,074,071, U.S. Pat. No. 5,485,355 and U.S. Pat. No. 5,876,863. Chemiluminescent fiber light sources are also known. These devices emit light when they are twisted to combine two chemicals contained in the fiber. The chemical reaction between the chemicals produces light while the chemical reaction proceeds for a few hours. However, these prior art chemiluminescent fiber light sources lack sufficient brightness, and are unable to achieve sufficient requirements for the medical or cosmetic use.

OLED fibers have been described recently in U.S. Pat. No. 6,538,375 B1, US 2003/0099858, and by Brenndan O'Connor et al. (Adv. Mater. 2007, 19, 3897-3900). Single OLED fibers and their use in lighting is described. However, the OLED fibers disclosed so far were aimed for display and general lighting applications.

Fiber OLEDs are also very interesting for the usage in so-called smart textiles. However, fiber OLEDs processed from solution remains still a technical challenge which is mainly due to the inhomogeneity of the surface of fiber and of the electrode coated on the fiber. This is because OLEDs are very sensitive to changes of the homogeneity of the surface and the thickness of the layers. For OLEDs, highly homogeneous layers are required. The thickness of layers in OLED is usually in the range between 20 to 80 nm causing a very narrow process window. For large pixels it is highly challenging to get thin films with a low roughness by employing a printing technique. The situation is even more complicated if the device is curved.

Furthermore encapsulation of such devices is still a very difficult task, because at least one reactive metal has to be used as cathode. Oxygen and humidity can inhibit or destroy the function of OLEDs.

There is, therefore, a need for the development of novel thin light sources without the drawbacks as described above.

BRIEF SUMMARY OF THE INVENTION

Surprisingly, organic light emitting electrochemical cells (OLECs) having the form of a fiber (hereinafter referred to as organic light emitting electrochemical fiber cell or OLEFC for short) can be used as light sources for general lighting, display applications, and the treatment and prophylaxis of medical and/or cosmetic diseases and conditions. OLEFCs are very simple in their structure and can therefore be prepared easily. The preparation of devices with curved surfaces is in the case of OLEFCs less complex as compared to the preparation of such surfaces in OLEDs. This is, at least in part, due to the fact that 1) in OLEFCs much thicker layers as compared to the layers in OLEDs with up to several mm of thickness can be used, 2) the requirements relating to homogeneity of the layer is less stringent for OLEFCs, 3) no reactive metal is required, and 4) processing from solution of the emissive layer is required which is due to the ionic compounds. Thus, process window is much wider and production costs in particular for mass production will be much lower as compared to the ones of OLEDs.

Furthermore, OLEFCs do not rely on air-sensitive charge-injection layers or metals such as Ba or Cs for electron injection, which further simplifies their preparation and makes them more cost efficient, as compared to OLEDs. This is due to the less stringent requirements for encapsulation of OLEFCs.

A BRIEF DESCRIPTION OF THE FIGURES

FIG. 1 schematically depicts the setup of an OLEFC (FIG. 1a and cross sectional view in FIG. 1b).

FIG. 2 illustrates fiber divided into segments emitting n different wavelengths λi (i=1 to n) or ranges of wavelengths (a). Preferably n=2 (b).

FIG. 3 illustrates parallel arrangement of light emitting fibers in a device which emits light with n different wavelengths or ranges of wavelengths.

FIG. 4 illustrates parallel arrangement of light emitting fibers in a device which emits light with two different wavelengths or ranges of wavelengths.

FIG. 5 illustrates woven fibers.

FIG. 6 illustrates woven fibers emitting two different wavelengths or ranges of wavelengths.

FIG. 7 illustrates plaster with attachment side 1, power supply 2, reflective material 3, and light emitting fibers 4.

FIG. 8 illustrates one way to prepare a fiber comprising the following steps. Step I: deposition of anode 20 on fiber core 10; step II: deposition of buffer layer 31; step III: deposition of interlayer 32; step IV: deposition of emissive layer 33; step V: deposition of cathode 40; step VI: free anode FIG. 9 illustrates electroluminescence (EL) spectrum of OLEFC1 using PB1 as EML.

FIG. 10 illustrates EL spectrum of OLEFC2 using PR1.

FIG. 11 illustrates EL spectrum of OLEFC3 using SY.

FIG. 12 illustrates schema of a plaster according to present invention with PEN substrate 300, OLEC fibers 400, cathode 40, anode 20, thin conducting wires 310 and 320, and epoxy resin encapsulation 330.

FIG. 13 illustrates fiber production line by employing dip coating. 210—fiber core; 130— deposition chamber for the first electrode; 200—deposition chamber for the second electrode; 140— container containing solution of buffer material or HIM; 160—container containing a solution or a formulation of HTM or interlayer material; 180—container containing a solution or a formulation of an emissive composition; 150, 170, and 190 are dryers.

FIG. 14 illustrates production method which is all solution based. 250—container containing an ink comprising a conductive material for the second electrode; 220 and 230 are dryers; 240—container comprising an ink comprising a conductive material for the first electrode.

A DETAILED DESCRIPTION OF THE INVENTION

The underlying technology of OLEFCs differs from the ones of OLEDs or LEDs. Both OLEDs and LEDs are working only on forward bias. In contrast to OLECs the I-V (current-voltage) curves of both OLEDs and LEDs are asymmetric. They represent semiconductor technologies whereas an OLEC or an OLEFC is basically an electrochemical or more precisely an electrolytic cell. An OLEO or an OLEFC works both on forward and backward bias. Charge transport in OLEDs occurs via the movement of holes and electrons from molecule to molecule until holes and electrons form so called excitons, i.e. electron-hole-pairs. Light is emitted when electrons and holes recombine. In OLEFCs, upon applying a voltage, ion double layers will form at first on both electrodes. Strong electric fields are built in the double layers, which reduce or even remove the energy barrier for electron and hole injection.

the electrolyte is oxidized at the anode and reduced at the cathode.

The molecular cations and anions diffuse under the electrical field and in the meanwhile doping the organic emissive materials until they meet together to form a so called p-n junction. Further an exciton is formed on the organic emissive compounds in the p-n junction. The radiative decay of the exciton leads to the emission of light. The original work and the principle of OLECs can be referred to the paper by Qibing Pei et al., Science, 1995, 269, 1086-1088. The OLE(F)Cs show symmetric I-VL curves, have low driving voltages, and there is no need for active metals as cathode.

But the time needed for forming p-n junction is long, therefore the turn-on is not instantaneous. Thus, up to date OLECs aren't suitable for display applications. However, therapeutic and cosmetic applications do not require fast turn-on or fast response times as display applications.

Another possible type of light emitting device comprising ionic materials is a device with an ionic p-n junction as reported by Daniel A. Bernards, et al., Science 2008, 313, 1416, wherein two layers are laminated together. One of the layers has a mobile anion and the other one has a mobile cation; by ion exchange an ionic p-n junction is formed in the interface between two layers. Here the ionic p-n junction is formed before the voltage is applied. The emission of light can then occur in the p-n junction. A similar light emitting device was also disclosed in US 2007/0157662 A1.

OLECs having a fiber form offer additional advantages for, e.g., lighting, display applications, and medical and/or cosmetic applications. They offer new ways to tailor devices required for specific applications, in particular if flexibility of a device is advantageous.

The present invention relates to an organic light emitting electrochemical cell (OLEC) comprising at least one ionic species, characterized in that the OLEC has the form of a fiber (OLEFC). The term fiber means a shape having a length which is much greater than the cross sectional diameter (or width or height for non-circular cross sections). In a preferred embodiment of the present invention, the term fiber means a shape that has rather large length to diameter ratio, such as 10:1 or greater. Particularly preferably, the length to diameter ratio is 100:1 or greater.

The OLEFC according to the present invention comprise at least two electrodes. Preferably the said OLEFC comprises two electrodes, a first and a second electrode. In particular the OLEFC comprises:

a) a first electrode,
b) light emitting layer, and
c) a second electrode.

The light emitting layer preferably comprises at least one organic light emitting material. Details related to the materials covered in the said OLEFC are described below in the present invention.

The present invention also relates to OLEFCs comprising a fiber core 10 (see FIG. 1). The fiber core may comprise a flexible fiber core member 10 and the first electrode 20 over the outer surface of the fiber core member 10. Preferably, the fiber core member 10 has the non-planar outer surface, such as a circular outer surface, and the first electrode 20 is formed around the entire outer surface of the fiber core member 10, such that the electrode 20 also has a non-planar outer surface, such as a circular surface. In an alternative preferred aspect of the present invention, the fiber core member 10 may be omitted, and the fiber core may consist entirely of the first electrode 20, such as a metal electrode having an elongated fiber shape. The electrode 20 may be hollow or solid.

Preferably, the electrode contains a non-planar outer surface, such as a circular surface.

The fiber core can be flexible or rigid and flexible fibers can either be ductile, i.e. it can be deformed plastically without fracture, or elastic, i.e. the fiber deforms reversibly and once the forces responsible for deformation are no longer applied, the object returns to its original shape. Preferably the fiber is flexible. By choosing the appropriate materials the degree of flexibility of the light emitting fibers can be tailored to any desired value.

The fiber core 10 may be transparent, translucent, opaque or reflective. The materials used can be glass, plastic, ceramic or metal foils, where plastic and metal foils are preferably used for flexible substrates. The fiber core member 10 may comprise a flexible polymeric or metallic material. Suitable polymeric materials for fiber core member 10 are polyolefins such as polyethylene, polypropylene, or polytetrafluoroethylene; polysiloxane; epoxy, polyacrylate; polyethyleneterephtalate; and derivatives thereof. Fiber core element 10 may comprise a glass or a metal such as aluminium, copper, or steel.

The glass used can be, for example, soda-lime glass, Ba- or Sr-containing glass, lead glass, aluminium silicate glass, borosilicate glass, Ba borosilicate glass or quartz.

Plastic plates can consist, for example, of polycarbonate resin, acrylic resin, vinyl chloride resin, polyethylene terephthalate resin, polyimide resin, polyester resin, epoxy resin, phenolic resin, silicone resin, fluorine resin, polyether sulfide resin or polysulfone resin.

For transparent fiber cores, use is made, for example, of polyethylene, ethylene-vinyl acetate copolymers, ethylene-vinyl alcohol copolymers, polypropylene, polystyrene, polymethyl methacrylate, PVC, polyvinyl alcohol, polyvinylbutyral, nylon, polyether ether ketone, polysulfone, polyether sulfone, tetrafluoroethylene-perfluoroalkyl vinyl ether copolymers, polyvinyl fluoride, tetrafluoroethylene-ethylene copolymers, tetrafluoroethylene-hexafluoropropylene copolymers, polychlorotrifluoroethylene, polyvinylidene fluoride, polyester, polycarbonate, polyurethanes, polyimide or polyether imide.

Other materials than those mentioned here can also be used as fiber core 10. Suitable materials are known to the person skilled in the art.

The core member preferably has a diameter (or height or width for noncircular cross sections) of about 1 µm to about 10 mm, particularly preferably 5 µm to 5 mm, and very particularly preferably 10 µm to 1 mm. The OLEFC may further comprise a power source electrically connected to the cathode 20 and the anode 40. The power source may be a voltage source, such as a small battery, a printed battery or a plug that plugs into a socket. The power source is connected to the cathode 20 and the anode 40. The power source may also contain a switch which allows the user to turn the device on and off, and/or a brightness control, such as a potentiometer.

The device may comprise an interactive steering unit. The steering unit may, e.g., allow a switch from continuous illumination to pulsed illumination. It also may allow the precise adaptation of irradiation intensities and/or wavelengths to be emitted. The steering unit may be directly associated to the device. It can also be separated via a permanent or temporary linkage. The device may be disposable and is suitable for uses in the hospital or outside the hospital.

The steering unit may be used interactively by the user, patient, physician, nurse, or other persons. The steering unit can also be operated according to the specification of expert, e.g. a physician, by programming it.

The fiber can also comprises a metal contact element in contact with a first portion of the outer surface of the radiation transmissive anode 40. The purpose of the contact element is to reduce the voltage drop along the length of the OLEFC, since a radiation transmissive anode material, such as indium tin oxide (ITO), may not have a high enough electrical conductivity to obtain the desired value of the voltage drop. The contact element may comprise any conductive metal, such as aluminum or copper. The moisture barrier layer 50 may comprise any material that prevents moisture from permeating into the organic layer 30, such as $SiO_2$, $Si_3N_4$ or silicon oxynitride. The encapsulation material 60 may comprise silicone or epoxy.

In a preferred embodiment the OLEFC according to the present invention comprises:
a) a fiber core 10 (see FIG. 1) having an outer first electrode 20;
b) a light emitting layer 30 comprising at least one organic electroluminescent compound and at least one ionic species, positioned over the outer surface of the said first electrode 20;
c) a radiation transmissive second electrode 40 positioned over the organic light emitting layer 30.

FIG. 1 schematically depicts the setup of an OLEFC (FIG. 1*a* and cross sectional view in FIG. 1*b*). Preferably the first electrode 20 is a cathode and the second electrode 40 is an anode. On the outer surface of the anode may be a metal contact element having a first surface in contact with a first portion of an outer surface of the anode, and a power source electrically connected to the cathode and the metal contact element.

As already mentioned, the first electrode 20 may be a cathode and the second electrode 40 may be a light transmissive anode. However, the polarity of the electrodes 20, 40 may be reversed, and electrode 20 may be the anode and electrode 40 may be the cathode. The two electrodes 20, 40 and the organic radiation emitting layer 30 comprise the OLED device.

If desired, the OLEFC may also comprise an optional radiation transmissive moisture and/or air barrier layer 50 and/or an optional radiation transmissive encapsulating material 60, as illustrated in FIG. 1. The inner surface of layer 50 surrounds the outer surface of the anode 40, and the inner surface of material 60 surrounds the outer surface of the layer 50, if layer 50 is present, or the outer surface of the anode 40.

If desired, the OLEFC may also comprise an optional refractive index matching layer. The inner surface of the refractive index matching layer surrounds the outer surface of the anode 40, and the inner surface of material 50 surrounds the outer surface of refractive index matching layer, if layer 50 is present. Such refractive index matching layers are helpful for light out-coupling. Suitable materials are dielectric materials with a high refractive index such as CsCl, NPB, C60, MeO-TPD, ZnO, 2,9-dimethyl 4,7-diphenyl-1,10-phenanthroline (BCP), $Alq_3$, Au, and $SnO_2$. The thickness of the index matching layer can be in the range between 1 and 300 nm, preferably in the range between 5 and 100 nm, and particularly preferably in the range between 10 and 60 nm. More details on refractive index matching can be found in US 20080231959 A1.

The light emitting fiber has a high brightness and can be made flexible if it has a fiber or tube shape. The fiber or tube shaped OLEFCs may have an improved moisture resistance while remaining flexible, in contrast to prior art flat plate OLEDs, by adding an outer moisture/air barrier layer and/or by forming an outer moisture and air impervious metal electrode around the fiber core.

The OLEFC according to the present invention can emit one ore more wavelengths or ranges of wavelengths. Different wavelengths (or ranges of wavelengths) can be achieved by the use of more than one light emitting layer 30 in one fiber with different functional materials emitting light of different wavelengths or ranges of wavelengths. Preferably the light emitting fiber according to the present invention comprises 3, particularly preferably 2, and very particularly preferably 1 light emitting layer 30.

The light emitting layer 30 can also comprise different emissive materials in one light emitting layer. Preferably the radiation emitting layer 30 comprises 3, particularly preferably 2, and very particularly preferably 1 emissive materials. The different emissive materials are selected from the emissive materials as described below, but any other emissive material suitable can be employed. If two emissive materials are used in one emissive layer the absorption spectrum of one of the two emissive materials preferably overlaps with the emission spectrum of the other emissive material.

Different wavelengths can also be accomplished by dividing the light emitting fiber into small segments having n distinct light emitting layer 30 as depicted in FIGS. 2a) and b) emitting n different wavelengths or ranges of wavelengths. If multiple segments are used in one fiber then n is preferably 4, particularly preferably 3, and very particularly preferably 2 (see FIG. 2 b). Preference is also given to a n OLEFC comprising multiple segments with n equals 1, i.e. each segment emits the same wavelength or ranges of wavelengths.

Devices emitting different wavelengths or ranges of wavelengths can also be obtained by employing different light emitting fibers as depicted in FIG. 3 and FIG. 4, whereby n is defined as above. Particular preference is given to a device comprising two distinct light emitting fibers (see FIG. 4).

The parallel arrangement of light emitting fibers in an device is only one possibility. Any processing known for fibers can be employed. The fibers can, e.g. be woven as depicted in FIG. 5. Hereby different light emitting fibers can be processed in order to get a canvas emitting different wavelengths or ranges of wavelengths. The fibers emitting the same wavelength(s) can be arranged in parallel to each other so that fibers emitting different wavelength(s) are perpendicular to each other (FIG. 6). The fibers emitting different wavelength(s) can also be arranged in an alternating fashion.

The organic radiation emitting layer 30 has a thickness in the range between 440 nm and 0.5 mm, preferably in the range between 100 nm and 0.1 mm, particularly preferably in the range between 200 nm and 50 μm, and very particularly preferably in the range between 500 nm and 10 μm and the electrodes 20, 40 each have a thickness in the range between 10 and 1000 nm, preferably in the range between 20 and 200 nm, and particularly preferably in the range between 20 and 100 nm. The organic radiation emitting fiber may also include an optional radiation scattering layer, comprising scattering particles such as $TiO_2$, $Al_2O_3$, or $SiO_2$ for effective color mixing and brightness uniformity. The scattering particles can also be mixed into the encapsulating material 60, or be formed as a separate layer over the encapsulating material 60, if desired. A variety of organic radiation emitting layers 30 can be used in conjunction with exemplary embodiments of the invention. The organic radiation emitting layer may comprise at least one polymer layer or at least one organic emissive molecule containing layer.

Suitable materials for both anode and cathode are all metaly and their alloys, preferably selected form Al, Ag, Au, Pt, Cu, Fe, Ir, Mo, Pd, Sn, V, Co, Ni, W, Ga, Ta, Sb, Zn, In, mixtures of two or more elements such as alloys comprising Mg/Al or Al/Li or Mg/Ag, metal oxides preferably selected from, but not limited to, indium tin oxide (ITO), indium zinc oxide (IZO), tin oxide (SnO), ZnO, InO, aluminium-zinc-oxide (AlZnO), and other metal oxides such as Al- and In-zinc oxide doped with zinc oxide, magnesium-indium-oxide, and nickel-tungsten-oxide. Metal nitrides such as galliumnitrides and metal selenides such as zinc-selenide and metal-sulfides such as zinc-sulfide can also be used. Further materials that can be used for electrodes (i.e. anodes and cathodes) are electrically conducting polymers, e.g. polythiophenes, polyanilines and polypyrroles or other conductive polymers, such as disclosed by M. S. Freud and B. A. Deore in "Self-Doped Conducting Polymers", John Wiley & Sons, Ltd, 2007.

The electrodes, i.e. anode and cathode, can be independently from each other be transparent, opaque, or reflective. The anode can also adopt an intermediate state, e.g. both being partially reflective and partially transparent.

If the electrodes are not or only partially transparent further conducting materials can be used. Preferred materials for non transparent or partially transparent anodes are selected from, but not limited to, Au, Ir, Mo, Pd, Pt, Cu, Ag, Sn, C, Al, V, Fe, Co, Ni, W, and mixtures thereof. The conducting materials can also be mixed with further conducting materials as described above, e.g. In—Cu.

The anode is preferably transparent and a particularly preferred material for the anode is ITO. Further materials can be used for anodes, which are known to the person skilled in the art.

Further suitable materials for cathodes, used to form a thin dielectric layer, are selected from a metal which is mixed with LiF, $Li_2O$, $BaF_2$, MgO, or NaF. A typical combination is LiF/Al.

An Mg/Al cathode with ITO layer on top is described in U.S. Pat. No. 5,703,436, U.S. Pat. No. 5,707,745, U.S. Pat. No. 6,548,956 B2, U.S. Pat. No. 6,576,134 B2. An Mg/Ag alloy is described in U.S. Pat. No. 4,885,221.

While the OLEFC as depicted in FIG. 1 has a circular cross section, it may have any other desired cross section. For example, the fiber may contain an oval cross section, a polygonal cross section (e.g. a square cross section) or a combination of circular, oval or polygonal cross sections.

The light emitting fiber preferably has a diameter (or height/width for noncircular cross sections) of about 1 μm to about 2 mm, particularly preferably 5 μm to 1 mm, and very particularly preferably 10 μm to 0.5 mm.

The OLEFC according to the present invention can comprise different materials. In principle any known material known to be used in organic light emitting cells can be used.

The materials may be selected from the group of small molecules, polymers, oligomers, or dendrimers, blends or mixtures thereof.

The term small molecule as used herein is defined as molecule not being a polymer, oligomer, dendrimer, or a blend. In particular, repeating structures are absent in small molecules. The molecular weight of small molecules is typically in the range of polymers with a low number of repeating units, oligomers or less.

The molecular weight of the small molecule is preferably below 4000 g/mol, particularly preferably below 3000 g/mol, and very particularly preferably below 2000 g/mol.

The polymers of the present invention preferably have 10 to 10000, particularly preferably 20 to 5000 and very particularly preferably 50 to 2000 repeat units. Oligomers according to this invention have preferably 2 to 9 repeat units. The branching index of the polymers and oligomers is between 0 (linear polymer without branching) and 1 (completely branched dendrimer). The term dendrimer as used herein is defined according to M. Fischer et al. in Angew. Chem., Int. Ed. 1999, 38, 885).

The molecular weight (MW) of the polymers of the present invention is preferably in the range of 10000 to 2000000 g/mol, particularly preferably in the range of 100000 to 1500000 g/mol, and very particularly preferably in the range of 200000 to 1000000 g/mol. The determination of MW can be performed according to standard techniques known to the person skilled in the art by employing gel permeation chromatography (GPC) with polystyrene as internal standard, for instance.

A blend is a mixture comprising at least one polymeric dendrimeric, or oligomeric component.

The present invention also relates to said OLEFC comprising at least one organic electroluminescent compound selected from fluorescent emitter materials, phosphorescent emitter materials, and emissive organo metallic complexes.

The OLEFC comprises 4, preferably 3, particularly preferably 2, and very particularly preferably 1 organic electroluminescent compound.

Preferably the OLEFC comprises the electroluminescent compound in a concentration range between 20 wt % and 95 wt %, particularly preferably between 30 wt % and 80 wt %, and very particularly preferably between 50 wt % and 75 wt % with respect to the total mass of the emissive layer.

For all of the materials selected from HIMs, HTMs, EIMs, ETMs the concentration is in the range between 1 wt % and 30 wt %, preferably in the range between 5 wt % and 25 wt %, and particularly preferably in the range between 10 wt % and 20 wt % with respect to the total mass of the emissive layer.

Further preference is given to an OLEFC comprising 4, preferably 3, particularly preferably 2, and very particularly preferably 1 fluorescent emitter materials.

Further preference is given to an OLEFC comprising 4, preferably 3, particularly preferably 2, and very particularly preferably 1 phosphorescent emitter materials.

Further preference is given to an OLEFC comprising 4, preferably 3, particularly preferably 2, and very particularly preferably 1 organo metallic complexes.

If more than one emitter material is used the emission spectrum of one emitter material preferably overlaps with the absorption spectrum of the another emitter material in order to facilitate Förster energy transfer.

The organic electroluminescent compounds belong to the class of organic functional materials. Organic functional materials, thus, comprise fluorescent emitter materials, phosphorescent emitter materials, and organo metallic complexes. They further comprise materials such as hole transport materials (HTM), hole injection materials (HIM), electron transport materials (ETM), and electron injection materials (EIM) as described below in more detail.

Organic functional materials according to the present invention are often characterized by their molecular frontier orbitals, i.e. the highest occupied molecular orbital (HOMO) (sometimes also referred to as valence band) and the lowest unoccupied molecular orbital (LUMO)(sometimes also referred to as conduction band). The HOMO and LUMO levels are routinely measured (by e.g. XPS=X-ray photoelectron spectroscopy, UPS=ultra-violet photoelectron spectroscopy or CV=cyclovoltammetry) or calculated (by quantum chemical methods such as (time dependent) DFT=density functional theory) which are known to the person skilled in the art. One skilled in the art is also aware of the fact that absolute values of these energy levels significantly depend on the method used. The reliable comparison of HOMO and LUMO energy levels of organic functional materials requires the employment of the same measurement method or calculation method The applicants established a consistent combination method to determine the energy levels of organic semiconductors. The HOMO/LUMO levels of a set of semiconductors (more than 20 different semiconductors) are measured by CV with a reliable evaluation method and also calculated by the DFT of Gaussian 03W with the same correction functional, for example B3PW91 and the same basis set, for example 6-31 G(d). The calculated values are then calibrated according to the measured values. Such calibration factor is used for further calculation. The agreement between calculated and measured values is very good. Therefore, the comparison of the energy levels of this invention is set on a sound base. The energy gaps or band gaps are obtained by the difference between HOMO and LUMO energy levels.

The term emitter refers to a material which, upon receiving excitonic energy by any kind of energy transfers from other materials, or by forming an exciton either electrically or optically, undergoes radiative decay to emit light. There are basically two classes of emitters, fluorescent and phosphorescent emitters. The term fluorescent emitter relates to materials or compounds which undergo a radiative transition from an excited singlet state to its ground state. The term phosphorescent emitter, as used herein, relates to luminescent materials or compounds which comprise transition metals. This typically includes materials emitting light caused by spin forbidden transition(s), e.g., transitions from excited triplet or quintet states.

The term dopant as employed herein is also used for the term emitter or emitter material.

Preferred blue fluorescent emitters to be employed in an OLEFC according to the present invention are selected from polyaromatic compounds, such as, for example, 9,10-di(2-naphthylanthracene) and other anthracene derivatives, derivatives of tetracene, xanthene, perylene, such as, for example, 2,5,8,11-tetra-t-butylperylene, phenylene, for example 4,4'-(bis(9-ethyl-3-carbazovinylene)-1,1'-biphenyl, fluorene, arylpyrenes (US 2006/0222886), arylenevinylenes (U.S. Pat. No. 5,121,029, U.S. Pat. No. 5,130,603), derivatives of rubrene, coumarine, rhodamine, quinacridone, such as, for example, N,N'-dimethylquinacridone (DMQA), dicyanomethylenepyrane, such as, for example, 4 (dicyanoethylene)-6-(4-dimethylaminostyryl-2-methyl)-4H-pyrane (DCM), thiopyrans, polymethine, pyrylium and thiapyrylium salts, periflanthene, indenoperylene, bis(azinyl)imine-boron compounds (US 2007/0092753 A1), bis(azinyl)methene compounds and carbostyryl compounds.

Further preferred blue fluorescent emitters are described in C. H. Chen et al.: "Recent developments in organic electroluminescent materials" Macromol. Symp. 125, (1997), 1-48 and "Recent progress of molecular organic electroluminescent materials and devices" Mat. Sci. and Eng. R, 39 (2002), 143-222.

Preferred fluorescent dopants according to the present invention are selected from the class of the monostyrylamines, the distyrylamines, the tristyrylamines, the tetrastyrylamines, the styrylphosphines, the styryl ethers and the arylamines.

A monostyrylamine is taken to mean a compound which contains one substituted or unsubstituted styryl group and at least one, preferably aromatic, amine. A distyrylamine is taken to mean a compound which contains two substituted or unsubstituted styryl groups and at least one, preferably aromatic, amine. A tristyrylamine is taken to mean a compound which contains three substituted or unsubstituted styryl groups and at least one, preferably aromatic, amine. A tetrastyrylamine is taken to mean a compound which contains four substituted or unsubstituted styryl groups and at least one, preferably aromatic, amine. The styryl groups are particularly preferably stilbenes, which may also be further substituted. The corresponding phosphines and ethers are defined analogously to the amines. For the purposes of this invention, an arylamine or an aromatic amine is taken to mean a compound which contains three substituted or unsubstituted aromatic or heteroaromatic ring systems bonded directly to the nitrogen. At least one of these aromatic or heteroaromatic ring systems is preferably a condensed ring system, preferably having at least 14 aromatic ring atoms. Preferred examples thereof are aromatic anthracene-amines, aromatic anthracene-diamines, aromatic pyrene amines, aromatic pyrene-diamines, aromatic chrysene-amines and aromatic chrysene-diamines. An aromatic anthracene-amine is taken to mean a compound in which one diarylamino group is bonded directly to an anthracene group, preferably in the 9 position. An aromatic anthracenediamine is taken to mean a compound in which two diarylamino groups are bonded directly to an anthracene group, preferably in the 9,10-position. Aromatic pyrene-amines, pyrene-diamines, chrysene-amines and chrysene-diamines are defined analogously thereto, where the diarylamino groups on the pyrene are preferably bonded in the 1 position or in the 1,6-position.

Further preferred fluorescent dopants are selected from indenofluorene-amines and indenofluorene-diamines, for example in accordance with WO 2006/122630, benzoindenofluorene-amines and benzoindenofluorene-diamines, for example in accordance with WO 2008/006449, and dibenzoindenofluorene-amines and dibenzoindenofluorene-diamines, for example in accordance with WO 2007/140847.

Examples of dopants from the class of the styrylamines are substituted or unsubstituted tristilbene-amines or the dopants described in WO 2006/000388, WO 2006/058737, WO 2006/000389, WO 2007/065549 and WO 2007/115610. Distyrylbenzene and distyrylbiphenyl derivatives are described in U.S. Pat. No. 5,121,029. Further styrylamines are found in US 2007/0122656 A1. Particularly preferred styrylamine dopants and triarylamine dopants are the compounds of the Formulae 1 to 6 and as disclosed in U.S. Pat. No. 7,250,532 B2, DE 102005058557 A1, CN 1583691 A, JP 08053397 A, U.S. Pat. No. 6,251,531 B1, and US 2006/210830 A.

Formula 1

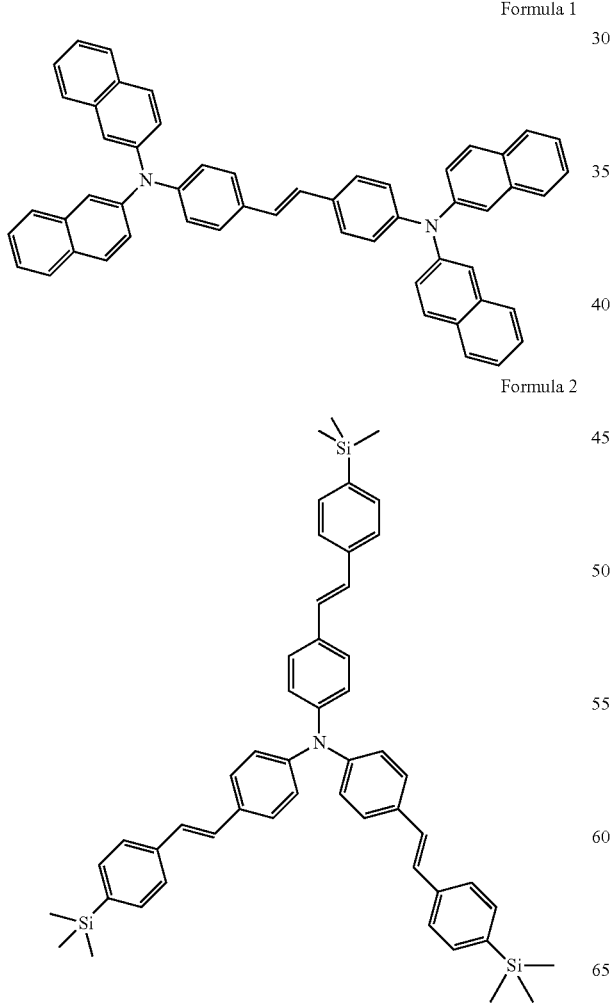

Formula 3

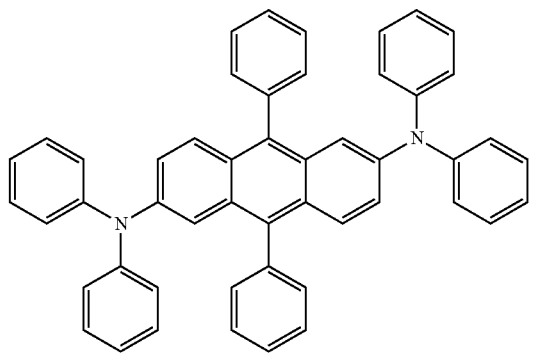

Formula 4

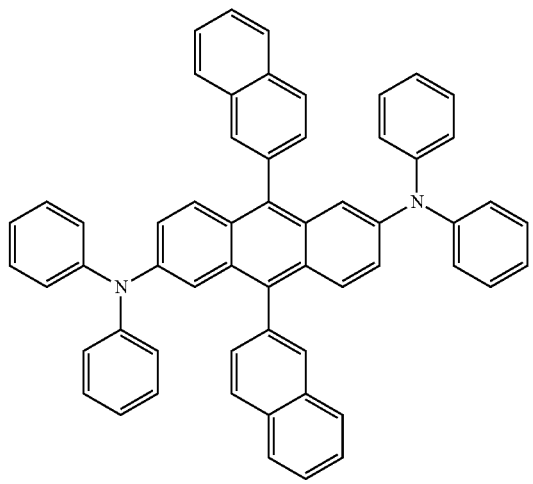

Formula 5

Formula 6

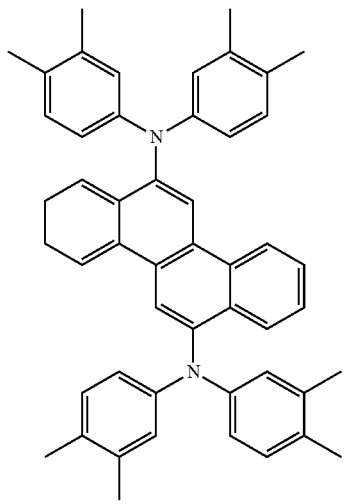

Further preferred fluorescent dopants are selected from the group of triarylamines as disclosed in EP 1957606 A1 and US 2008/0113101 A1.

Further preferred fluorescent dopants are selected from derivatives of naphthalene, anthracene, tetracene, fluorene, periflanthene, indenoperylene, phenanthrene, perylene (US 2007/0252517 A1), pyrene, chrysene, decacyclene, coronene, tetraphenylcyclopentadiene, pentaphenylcyclopentadiene, fluorene, spirofluorene, rubrene, coumarine (U.S. Pat. No. 4,769,292, U.S. Pat. No. 6,020,078, US 2007/0252517 A1), pyran, oxazone, benzoxazole, benzothiazole, benzimidazole, pyrazine, cinnamic acid esters, diketopyrrolopyrrole, acridone and quinacridone (US 2007/0252517 A1).

Of the anthracene compounds, particular preference is given to 9,10-substituted anthracenes, such as, for example, 9,10-diphenylanthracene and 9,10-bis(phenylethynyl)anthracene. 1,4-Bis(9'-ethynylanthracenyl)benzene is also a preferred dopant.

Examples of phosphorescent emitters are revealed by the applications WO 00/70655, WO 01/41512, WO 02/02714, WO 02/15645, EP 1191613, EP 1191612, EP 1191614 and WO 2005/033244. In general, all phosphorescent complexes as used in accordance with the prior art for phosphorescent compounds used in electroluminescent devices and as are known to the person skilled in the art in the area of organic electroluminescence are suitable, and the person skilled in the art will be able to use further phosphorescent complexes without inventive step.

The phosphorescent emitter may be a metal complex, preferably with the formula $M(L)_z$, wherein M is a metal atom, L is in each occurrence independently of one another an organic ligand that is bonded to or coordinated with M via one, two or more positions, and z is an integer $\geq 1$, preferably 1, 2, 3, 4, 5 or 6, and wherein, optionally, these groups are linked to a polymer via one or more, preferably one, two or three positions, preferably via the ligands L.

M is in particular a metal atom selected from transition metals, preferably selected from transition metals of group VIII, or lanthanoides, or actinides, particularly preferably selected from Rh, Os, Ir, Pt, Pd, Au, Sm, Eu, Gd, Tb, Dy, Re, Cu, Zn, W, Mo, Pd, Ag, or Ru, and very particularly preferably selected from Os, Ir, Ru, Rh, Re, Pd, or Pt. M may also be Zn.

The OLEFC according to the present invention can also comprise at least one metal complex. According to quantum mechanics the transition from excited states with high spin multiplicity, e.g. from excited triplet states, to ground state is forbidden. However, the existence of an heavy atom, for example iridium, osmium, platinum and europium, results in a strong spinorbit coupling, i.e. the excited singlet and triplet are mixed so that triplet gains some singlet character; and if singlet-triplet mixing yields a radiative decay rate faster than the non-radiative event, then the luminance can be efficient. This kind of emission can be achieved using metal complex, as firstly reported by Baldo et al.; Nature 395, 151-154 (1998).

Preferred ligands are 2 phenylpyridine derivatives, 7,8-benzoquinoline derivatives, 2 (2-thienyl)pyridine derivatives, 2 (1-naphthyl)pyridine derivatives or 2 phenylquinoline derivatives. All these compounds may be substituted, for example by fluoro- or trifluoromethyl substituents for blue emission. Auxiliary ligands are preferably acetylacetonate or picric acid.

In particular, complexes of Pt or Pd with tetradentate ligands of the Formula 7 as disclosed in US 2007/0087219 A1, wherein $R^1$ to $R^{14}$ and $Z^1$ to $Z^5$ are as defined in the reference, Pt porphyrin complexes having an enlarged ring system (US 2009/0061681 A1) and Ir complexes are suitable, for example 2,3,7,8,12,13,17,18-octaethyl-21H,23H-porphyrinPt(II), tetraphenyl-Pt(II)-tetrabenzoporphyrin (US 2009/0061681 A1), cis bis(2-phenylpyridinato-N,C2')Pt(II), cis-bis(2-(2'-thienyl)pyridinato-N,C3')Pt(II), cis-bis(2-(2'-thienyl)quinolinato-N,C5')Pt(II), (2-(4,6-difluorophenyl)pyridinato-N,C2')Pt(II) acetylacetonate, or tris(2-phenylpyridinato-N,C2')Ir(III) (Ir(ppy)₃, green), bis(2-phenylpyridinato-N,C2)Ir(III) acetylacetonate (Ir(ppy)₂ acetylacetonate, green, US 2001/0053462 A1, Baldo, Thompson et al. Nature 403, (2000), 750-753), bis(1-phenylisoquinolinato-N,C2')(2-phenylpyridinato-N,C2')iridium(III), bis(2-phenylpyridinato-N, C2')(1-phenylisoquinolinato-N,C2')iridium(III), bis(2-(2'-benzothienyl)pyridinato-N,C3')iridium(III) acetylacetonate, bis(2-(4',6'-difluorophenyl)pyridinato-N,C2')iridium(III) piccolinate (Firpic, blue), bis(2-(4',6'-difluorophenyl)pyridinato-N,C2')Ir(III) tetrakis(1-pyrazolyl)borate, tris(2-(biphenyl-3-yl)-4-tertbutylpyridine)iridium(III), (ppz)₂Ir(5phdpym) (US 2009/0061681 A1), (45ooppz)₂Ir(5phdpym) (US 2009/0061681 A1), derivatives of 2 phenylpyridine-Ir complexes, such as, for example, iridium(III) bis(2-phenylquinolyl-N,C2')acetylacetonate (PQIr), tris(2-phenylisoquinolinato-N,C)Ir(III) (red), bis(2-(2'-benzo[4,5-a]thienyl)pyridinato-N,C3)Ir acetylacetonate ([Btp2Ir(acac)], red, Adachi et al. Appl. Phys. Lett. 78 (2001), 1622-1624).

Formula 7

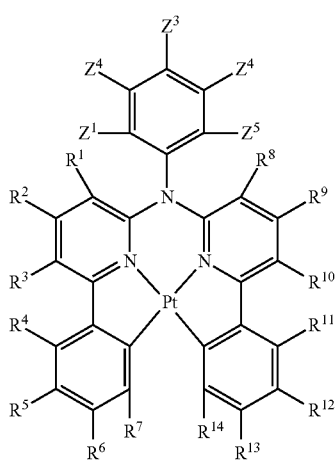

Also suitable are complexes of trivalent lanthanides, such as, for example, $Tb^{3+}$ and $Eu^{3+}$ (J. Kido et al. Appl. Phys. Lett. 65 (1994), 2124, Kido et al. Chem. Lett. 657, 1990, US 2007/0252517 A1), or phosphorescent complexes of Pt(II), Ir(I), Rh(I) with maleonitrile dithiolate (Johnson et al., JAGS 105, 1983, 1795), Re(I) tricarbonyl diimine complexes (Wrighton, JAGS 96, 1974, 998 inter alia), Os(II) complexes with cyano ligands and bipyridyl or phenanthroline ligands (Ma et al., Synth. Metals 94, 1998, 245) or $Alq_3$ without a host.

Further phosphorescent emitters with tridentate ligands are described in U.S. Pat. No. 6,824,895 and U.S. Pat. No. 7,029,766. Red-emitting phosphorescent complexes are mentioned in U.S. Pat. No. 6,835,469 and U.S. Pat. No. 6,830,828.

A particularly preferred phosphorescent dopant is a compound with the Formula 8 and further compounds as disclosed, e.g., in US 2001/0053462 A1.

A particularly preferred phosphorescent dopant is a compound with the Formula 9 and further compounds as disclosed, e.g., in WO 2007/095118 A1

Formula 8

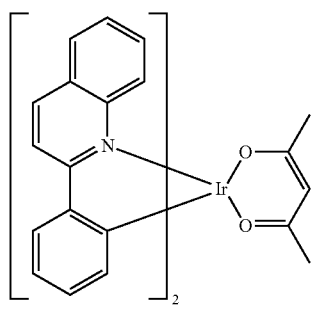

Formula 9

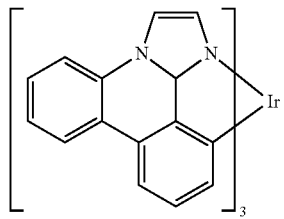

Further derivatives are described in U.S. Pat. No. 7,378,162 B2, U.S. Pat. No. 6,835,469 B2, and JP 2003/253145 A.

Further preference is given to phosphorescent emitter selected from carbene triple emitter, particularly to carbine complexes comprising iridium as metal. Preferred complexes are N-heterocyclic carbine (NHC) iridium complexes as disclosed in WO 2005/091373, WO 2005/113704, and in P. Erk et al., SID 2006, 11, 2, 131, e.g. fac-Ir(dpbic)$_3$, Ir(pmbic)$_3$, Ir(pmic)$_3$, Ir(dpnic)$_3$, Ir(cn-pmic)$_3$.

Further to metal complex mentioned elsewhere herein, a suitable metal complex according to the present invention can be selected from transition metals, rare earth elements, lanthanides and actinides is also subject of this invention. Preferably the metal is selected from Ir, Ru, Os, Eu, Au, Pt, Cu, Zn, Mo, W, Rh, Pd, or Ag.

The electroluminescent compound may also be a polymer, oligomer, dendrimer, and blend.

The polymer may also have further functions such as charge transfer transport function. Therefore, the present inventions also relates to compositions comprising further polymeric molecules.

Preferably, the said polymer comprises units, which are preferably selected from the groups comprising phosphorescent emitter, particularly emissive metal complexes as described above. Particular preference is given here to corresponding structural units which contain elements from groups 8 to 10 (Ru, Os, Rh, Ir, Pd, Pt).

The polymer is characterized in that different functions may be incorporated into one large molecule or a blend of large molecules. The functions are, inter alia, the ones of a hole injection material, hole transport material, emissive material, electron injection material, and electron transport material. The functions which are incorporated into a polymer can be categorized into different groups. By choosing the desired functional groups and the ratio between them, the polymer can be tuned to have the desired function(s).

The difference between polymers, oligomers and dendrimers is due to the size, size distribution, and branching of the molecular entities as defined elsewhere within the present invention.

Different structures are, inter alia, those as disclosed and extensively listed in WO 2002/077060 A1 and in DE 10337346 A1. The structural units may originate, for example, from the following groups:

Group 1: units which increase the hole-injection and/or transport properties of the polymers; It corresponds to the HIMs or HTMs as described elsewhere within the present invention.

Group 2: units which increase the electron-injection and/or transport properties of the polymers; It corresponds to the EIMs or ETMs as described elsewhere within the present invention.

Group 3: units which have combinations of individual units from group 1 and group 2;

Group 4: units which modify the emission characteristics to such an extent that electrophosphorescence may be obtained instead of electrofluorescence; typically, it corresponds to the phosphorescent emitter, or more preferably emissive metal complexes as described elsewhere within the present invention.

Group 5: units which improve the transition from the so called singlet state to higher spin states, e.g. to a triplet state;

Group 6: units which influence the morphology and/or emission colour of the resultant polymers;

Group 7: units which are typically used as backbone and which may have electron transport function, hole transport function or both.

Preferably, the polymer is a hole transport or injection polymer comprising units of groups 1, which are preferably selected from units comprising the low molecular weight HTMs or HIMs as described above.

Further preferred units from group 1 are, for example, triarylamine, benzidine, tetraaryl-para-phenylenediamine, carbazole, azulene, thiophene, pyrrole and furan derivatives and further O, S, or N containing heterocycles.

Preferred polymeric HTM or HIM is a polymer comprising at least one of following repeat unit according to Formulae 10.

Formula 10

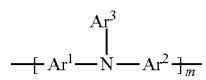

wherein
$Ar^1$ which may be the same or different, denote, independently if in different repeat units, a single bond or an optionally substituted mononuclear or polynuclear aryl group,
$Ar^2$ which may be the same or different, denote, independently if in different repeat units, an optionally substituted mononuclear or polynuclear aryl group, Ar³ which may be the same or different, denote, independently if in different repeat units, an optionally substituted mononuclear or polynuclear aryl group,
m is 1, 2 or 3.

Particularly preferred units of Formula 10 are selected from the group consisting of the Formulae 11 to 13:

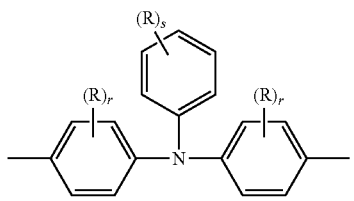

Formula 11

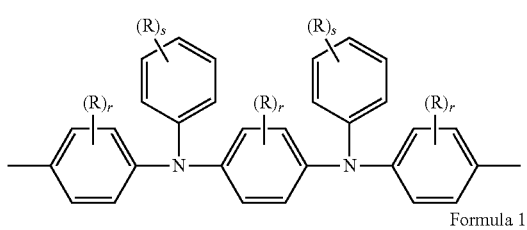

Formula 12

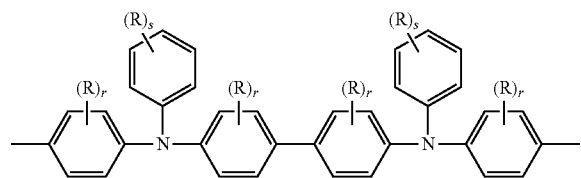

Formula 13 wherein
R which may be the same or different in each occurrence, is selected from H, substituted or unsubstituted aromatic or heteroaromatic group, alkyl, cycloalkyl, alkoxy, aralkyl, aryloxy, arylthio, alkoxycarbonyl, silyl, carboxy group, a halogen atom, cyano group, nitro group or hydroxy group,
r is 0, 1, 2, 3 or 4, and
s is 0, 1, 2, 3, 4 or 5.

Further preferred polymeric HTM or HIM is a polymer comprising at least one of following repeat unit according to Formula 14.

Formula 14 wherein
$T^1$ and $T^2$ are independently of each other selected from thiophene, selenophene, thieno[2,3b]thiophene, thieno[3,2b]thiophene, dithienothiophene, pyrrole, aniline, all of which are optionally substituted with $R^5$,
$R^5$ is in each occurrence independently of each other selected from halogen, —CN, —NC, —NCO, —NCS, —OCN, SCN, $C(=O)NR^0R^{00}$, —C(=O)X, —C(=O)R$^0$, —NH$_2$, —NR$^0R^{00}$, SH, SR$^0$, —SO$_3$H, —SO$_2$R$^0$, —OH, —NO$_2$, —CF$_3$, —SF$_5$, optionally substituted silyl, or carbyl or hydrocarbyl with 1 to 40 C atoms that is optionally substituted and optionally contains one or more hetero atoms,
Ar$^4$ and Ar$^5$ are independently of each other mononuclear or polynuclear aryl or heteroaryl, which is optionally substituted and optionally fused to the 2,3-positions of one or both of the adjacent thiophene or selenophene groups,
c and e are independently of each other 0, 1, 2, 3 or 4, with 1<c+e 6, d and f are independently of each other 0, 1, 2, 3 or 4.

Examples for polymeric HTMs are as disclosed in WO 2007/131582 A1 and WO 2008/009343A1.

Preferably, the said polymer comprises units of groups 2, which are preferably selected from groups comprising the low molecular weight ETMs or EIMs as described elsewhere within the present invention.

Further preferred units from group 2, which have electron-injection or electron-transport properties, are, for example, pyridine, pyrimidine, pyridazine, pyrazine, oxadiazole, quinoline, quinoxaline and phenazine derivatives, but also triarylboranes and further O, S, or N containing heterocycles.

Preferably, the said polymer comprises units from group 3 in which structures which increase the hole mobility and the electron mobility (i.e. units from groups 1 and 2) are bonded directly to one another. Some of these units may serve as emitters and shift the emission colour into the green, yellow or red. Their use is thus suitable, for example, for the production of other emission colours or a broad-band emission from originally blue-emitting polymers.

Preferably, the polymer comprises units of group 4, which are preferably selected from the groups comprising phosphorescent emitter, particularly emissive metal complexes as described elsewhere within the present invention. Particular preference is given here to corresponding structural units which contain elements from groups 8 to 10 (Ru, Os, Rh, Ir, Pd, Pt).

Preferably, the said polymer comprises units of group 5, which can improve the transition from the singlet state to the triplet state and which, employed in support of the structural elements from group 4, improve the phosphorescence properties of these structural elements. Suitable for this purpose are, in particular, carbazole and bridged carbazole dimer units, as described in DE 10304819 A1 and DE 10328627 A1. Also suitable for this purpose are ketones, phosphine oxides, sulfoxides, sulfones, silane derivatives and similar compounds, as described in DE 10349033 A1. Further preferred structure units can be selected from groups comprising the low molecular weight phosphorescent matrices as described elsewhere within the present invention.

Preferably, the said polymer comprises units of group 6, which influence the morphology and/or emission colour of the polymers, are, besides those mentioned above, those which have at least one further aromatic or another conjugated structure which do not fall under the above-mentioned groups, i.e. which have only little effect on the charge-carrier mobilities, which are not organometallic complexes or which have no influence on the singlet-triplet transition. Structural elements of this type may influence the morphology and/or emission colour of the resultant polymers. Depending on the unit, they can therefore also be employed as emitters. Preference is given here to aromatic structures having 6 to 40 C atoms or also tolan, stilbene or bisstyrylarylene derivatives, each of which may be substituted by one or more radicals R$^1$. Particular preference is given here to the incorporation of 1,4-phenylene, 1,4-naphthylene, 1,4- or 9,10-anthrylene, 1,6-, 2,7- or 4,9-pyrenylene, 3,9- or 3,10-perylenylene, 4,4'-biphenylylene, 4,4''-terphenylylene, 4,4'bi 1,1'-naphthylylene, 4,4'-tolanylene, 4,4'-stilbenylene or 4,4''-bisstyrylarylene derivatives.

Preferably, the said polymer comprises units of group 7 which contain aromatic structures having 6 to 40 C atoms which are typically used as polymer backbone. These are, for example, 4,5-dihydropyrene derivatives, 4,5,9,10-tetrahydropyrene derivatives, fluorene derivatives as disclosed for example in U.S. Pat. No. 5,962,631, WO 2006/052457 A2 and WO 2006/118345A1,9,9'-spirobifluorene derivatives as disclosed for example in WO 2003/020790 A1, 9,10-phenanthrene derivatives as disclosed, for example, in WO 2005/104264 A1, 9,10-dihydrophenanthrene derivatives as disclosed for example in WO 2005/014689 A2, 5,7-dihydrodibenzooxepine derivatives and cis- and trans-indenofluorene derivatives as disclosed for example in WO 2004/041901 A1, WO 2004/113412 A2 and, binaphthylene derivatives as disclosed for example in WO 2006/063852 A1, and further units as disclosed for example in WO 2005/056633A1, EP 1344788A1 and WO 2007/043495A1, WO 2005/033174 A1, WO 2003/099901 A1 and DE 102006003710.3.

Further preferred structural elements from group 7 are selected from fluorene derivatives, as disclosed for example in U.S. Pat. No. 5,962,631, WO 2006/052457 A2 and WO 2006/118345A1, spiro-bifluorene derivatives as disclosed for example in WO 2003/020790 A1, benzofluorene, dibenzofluorene, benzothiophene, dibenzofluorene and their derivatives as disclosed for example in WO 2005/056633A1, EP 1344788A1 and WO 2007/043495A1

Very preferred structural elements of group 7 are those of Formula 15:

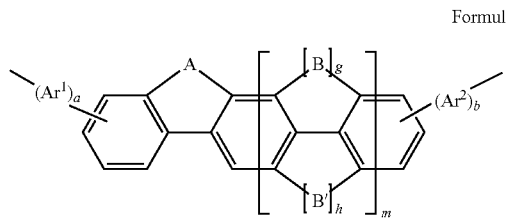

Formula 15 wherein
A, B and B' are independently of each other, and in case of multiple occurrence independently of one another, a divalent group, preferably selected from —CR$^1$R$^2$—, —NR$^1$—, —PR$^1$—, —O—, —S—, —SO—, —SO$_2$—, —CO—, —CS—, —CSe—, —P(=O)R$^1$—, —P(=S)R$^1$— and —SiR$^1$R$^2$—,
R$^1$ and R$^2$ are independently of each other identical or different groups selected from H, halogen, —CN, —NC, —NCO, —NCS, —OCN, —SCN, —C(=O)NR$^0$R$^{00}$, —C(=O)X, —C(=O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl, or carbyl or hydrocarbyl with 1 to 40 C atoms that is optionally substituted and optionally comprises one or more hetero atoms, and optionally the groups
R$^1$ and R$^2$ form a spiro group with the fluorene moiety to which they are attached,
X is halogen,
R$^0$ and R$^{00}$ are independently of each other H or an optionally substituted carbyl or hydrocarbyl group optionally comprising one or more hetero atoms,
each g is independently 0 or 1 and each corresponding h in the same subunit is the other of 0 or 1,
m is an integer ≥1
Ar$^1$ and Ar$^2$ are independently of each other mono- or polynuclear aryl or heteroaryl that is optionally substituted and optionally fused to the 7,8-positions or 8,9-positions of the indenofluorene group,
a and b are independently of each other 0 or 1.

If the groups R$^1$ and R$^2$ form a spiro group with the fluorene group to which they are attached, it is preferably spirobifluorene.

The groups of Formula 15 are preferably selected from the following Formulae 16 to 20:

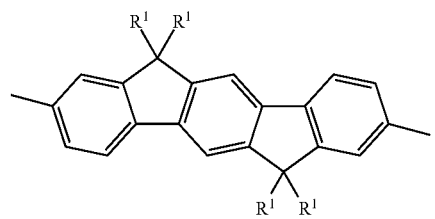

Formula 16

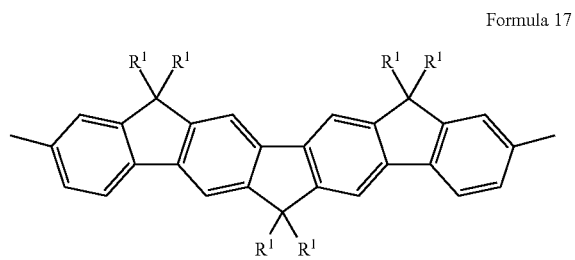

Formula 17

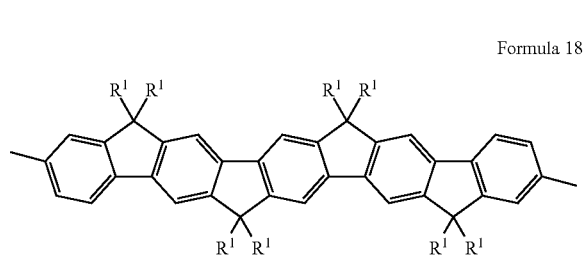

Formula 18

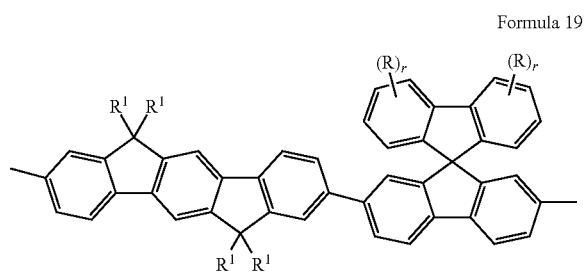

Formula 19

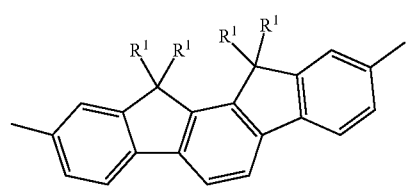

Formula 20 wherein R$^1$ is as defined in Formula 15, r is 0, 1, 2, 3 or 4, and R has one of the meanings of R$^1$.

R is preferably F, Cl, Br, I, —CN, —NO$_2$, —NCO, —NCS, —OCN, —SCN, —C(=O)NR$^0$R$^{00}$, —C(=O)X$^0$, —C(=O)R$^0$, —NR$^0$R$^{00}$, optionally substituted silyl, aryl or heteroaryl with 4 to 40, preferably 6 to 20 C atoms, or straight chain, branched or cyclic alkyl, alkoxy, alkylcarbonyl, alkoxycarbonyl, alkylcarbonyloxy or alkoxycarbonyloxy with 1 to 20, preferably 1 to 12 C atoms, wherein one or more H atoms are optionally replaced by F or Cl, and wherein R$^0$, R$^{00}$ and X$^0$ are as defined above.

Particularly preferred groups of Formula 15 are selected from the following Formulae 21 to 24:

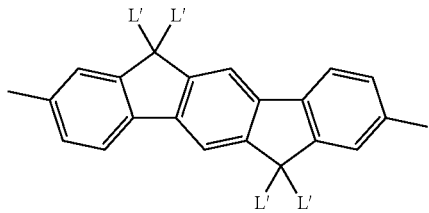

Formula 21

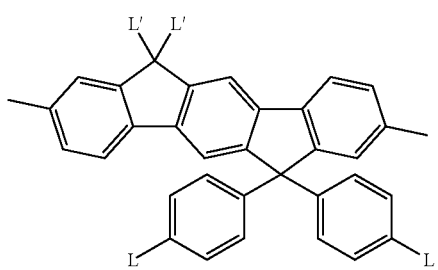

Formula 22

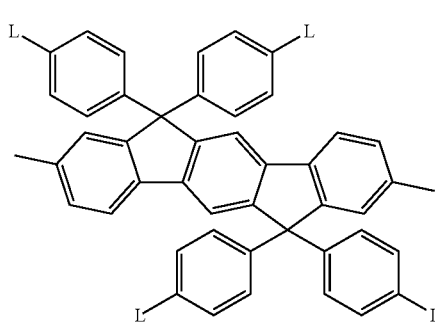

Formula 23

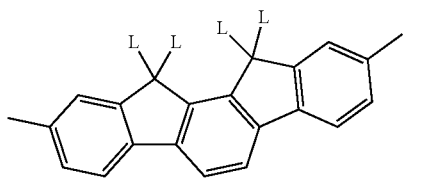

Formula 24 wherein
L is H, halogen or optionally fluorinated, linear or branched alkyl or alkoxy with 1 to 12 C atoms, and is preferably H, F, methyl, i-propyl, t-butyl, n-pentoxy, or trifluoromethyl, and L' is optionally fluorinated, linear or branched alkyl or alkoxy with 1 to 12 C atoms, and is preferably n-octyl or n-octyloxy.

Preference is given to polymers suitable for use in the invention which simultaneously comprise one or more units selected from groups 1 to 8. It may likewise be preferred for more than one structural unit from a group to be present simultaneously.

Preference is given to polymers suitable for use in the invention which, besides structural units of an emitter, also comprise at least one structural unit from the above-mentioned groups. At least two structural units are particularly preferably from different classes of those mentioned above.

The proportion of the different classes of groups, if present in the polymer, is preferably in each case at least 5 mol %, particularly preferably in each case at least 10 mol %. In particular, one of these structural units is selected from the group of hole-conducting units and the other group is an emitting unit, where these two functions (hole conduction and emission) may also be taken on by the same unit.

However, a smaller proportion of the emitting units, in particular green- and red-emitting units, may also be preferred, for example for the synthesis of white-emitting copolymers. The way in which white-emitting copolymers can be synthesised is described in detail in DE 10343606 A1.

In order to ensure adequate solubility, it is preferred for on average at least 2 non-aromatic C atoms to be present in the substituents per recurring unit. Preference is given here to at least 4 and particularly preferably at least 8 C atoms. In addition, individual C atoms of these may be replaced by O or S. However, it is entirely possible for this to mean that a certain proportion of recurring units does not carry any further nonaromatic substituents.

In order to avoid impairing the morphology of the film, it is preferred to have no long-chain substituents having more than 12 C atoms in a linear chain, particularly preferably none having more than 8 C atoms and in particular none having more than 6 C atoms.

The said polymer may be statistical or random copolymers, alternating or regioregular copolymers, block copolymers or combinations thereof.

In a very preferred embodiment, the polymer is a conjugated polymer, wherein the functional groups as described above and bellow are integrated into the polymer main chain.

In another preferred embodiments, the polymer is a non-conjugated or partially-conjugated polymer.

In a particularly preferred embodiment, the said polymer is a main-chain non-conjugated polymer, wherein the polymer comprises at least one non-conjugated spacer on main-chain. Very particularly preferred non-conjugated or partially-conjugated polymers comprise a non-conjugated backbone unit or a unit interrupting the conjugation of backbone units. Like side-chain non-conjugated polymers, main-chain non-conjugated polymers give also a high triplet level.

Preferred non-conjugated backbone units are selected from units comprising indenofluorene derivatives, as shown, for example, in the following Formulae 25 and 26 and as disclosed in DE 102009023156.0.

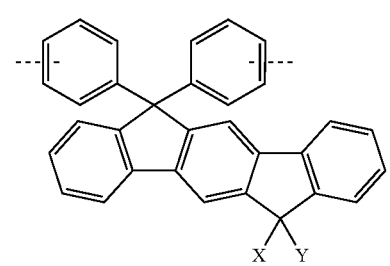

Formula 25

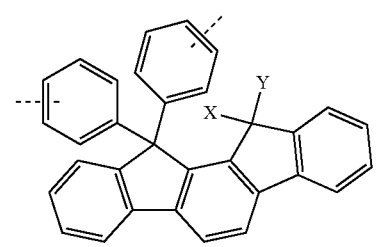

Formula 26 wherein X and Y are independently from each other selected from H, F, an alkyl group with 1 to 40 C-atoms, an alkylene group having 2 to 40 C-atoms, an alkinyl group having 2 to 40

C-Atoms, an substituted or unsubstituted aryl group having 6 to 40 C-atoms, and a substituted or unsubstituted heteroaryl group having 5 to 25 atoms.

Further preferred non-conjugated backbone units are selected from a unit comprising fluorene, phenanthrene, dehydrophenanthrene, indenofluorene derivatives, as shown, for example, in the following Formulae 27 to 0 and as disclosed in DE 102009023154.4.

Formula 27
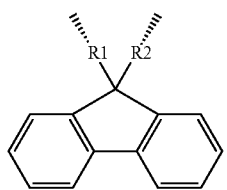

Formula 28
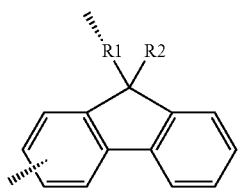

Formula 29
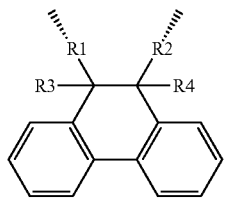

Formula 30
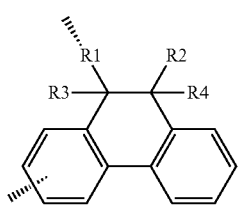

Formula 31
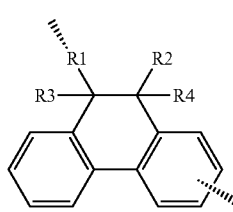

Formula 32
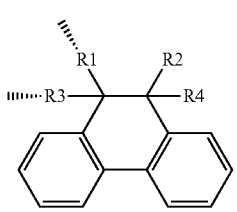

Formula 33
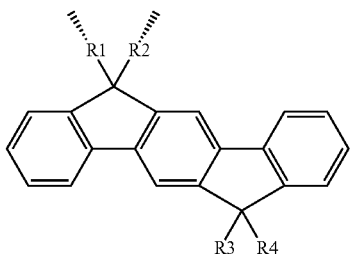

Formula 34
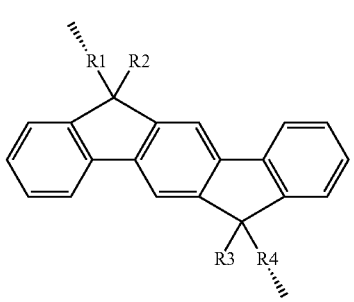

Formula 35
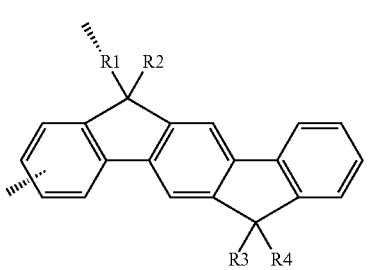

Formula 36
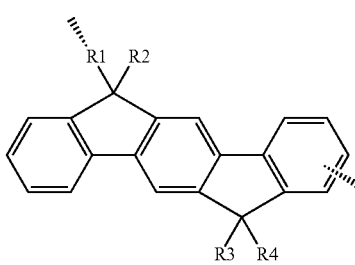

Formula 37
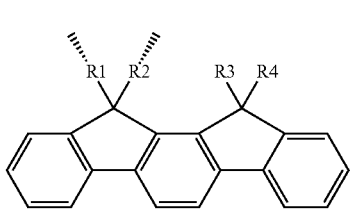

Formula 38
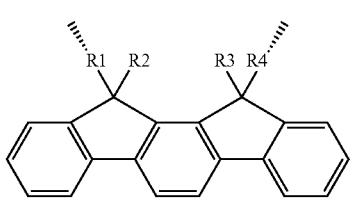

-continued

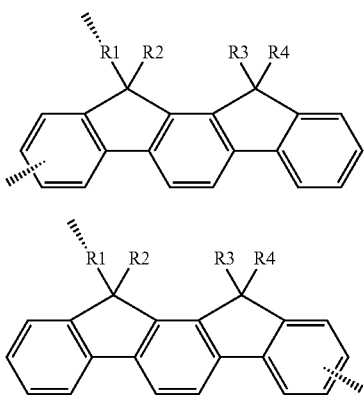

Formula 39

Formula 40 wherein R' to R$^4$ have the sae meaning as X and Y, as defined above.

In another preferred embodiment, the said polymer is a side-chain non-conjugated polymer, which is especially important for phosphorescent emission based on polymer. In general, such phosphorescent polymer is obtained by means of radical copolymerization of vinyl compounds, and comprises at least one phosphorescent emitter and at least one charge transport unit on side chain, as disclosed in U.S. Pat. No. 7,250,226 B2. Further examples for such phosphorescent polymer are disclosed for example in JP 2007/211243 A2, JP 2007/197574 A2, U.S. Pat. No. 7,250,226B2, JP 2007/059939A.

In a further embodiment, the said polymer can also be a non-conjugated polymer for fluorescent emission. Preferred singlet non-conjugated polymers are, for example, side-chain polymers with antracenenes, benzanthrecenes and their derivates in the side-chain, as disclosed in JP 2005/108556, JP 2005/285661, JP 2003/338375 etc.

The said polymers can also act as ETM or HTM, preferably the polymer is a non-conjugated polymer.

The organic functional materials according to the present invention can also be selected from host materials. Host materials are usually used in combination with emitter and have, in general, larger energy gaps between the HOMO and the LUMO as compared to emitter materials. In addition, host materials behave either as electron or hole transport material. Host materials can also have both electron and hole transport properties. In case singlet transitions are predominantly responsible for photoluminescence in OLEFCs, a maximal overlap between the absorption spectrum of the emitter with the photoluminescence spectrum of the host material is highly desirably. This ensures the energy transfer from the host material to the emitter.

Host material is also called matrix or matrix material, particularly if a host is meant which is used in combination with a phosphorescent emitter. In the case of a copolymer comprising emitter units, the polymer backbone acts as a host.

The present invention also relates to a OLEFC comprising at least one host material and at least one emitter material, wherein the host material is preferably selected from anthracenes, benzanthracenes, ketones, carbazoles, triarylamines, indenofluorenes, fluorenes, spirobifluorenes, phenanthrenes, dihydrophenanthrenes, thiophenes, triazines, imodazoles, isomers and derivatives thereof.

The OLEFC comprises 4, preferably 3, particularly preferably 2, and very particularly preferably 1 host materials.

Thus, the said OLEFC may also comprise more than one host material. If the OLEFC comprises more than one host material the host materials are also referred to as co-host or co-host materials.

Preferred host materials suitable for fluorescent emitter are selected from anthracenes, benzanthracenes, indenofluorenes, fluorenes, spirobifluorenes, phenanthrenes, dehydrophenanthrenes, thiophenes, triazines, imidazole and derivatives thereof.

Preferred host materials suitable for fluorescent emitter are selected from anthracenes, benzanthracenes, indenofluorenes, fluorenes, spirobifluorenes, phenanthrenes, dehydrophenanthrenes, thiophenes, triazines, and imidazole.

Particularly preferred host materials for fluorescent emitter are selected from the classes of the oligoarylenes (for example 2,2',7,7'-tetraphenylspirobifluorene in accordance with EP 676461 or dinaphthylanthracene), in particular the oligoarylenes containing condensed aromatic groups, such as, for example, phenanthrene, tetracene, coronene, chrysene, fluorene, spirofluorene, perylene, phthaloperylene, naphthaloperylene, decacyclene, rubrene, the oligoarylenevinylenes (for example 4,4'-bis(2,2-diphenylethenyl)-1,1'-biphenyl (DPVBi) or 4,4-bis-2,2-diphenylvinyl-1,1-spirobiphenyl (spiro-DPVBi) in accordance with EP 676461), the polypodal metal complexes (for example in accordance with WO 2004/081017), in particular metal complexes of 8 hydroxyquinoline, for example aluminium(III) tris(8-hydroxyquinoline) (aluminium quinolate, Alq$_3$) or bis(2-methyl-8-quinolinolato)-4-(phenylphenolinolato)aluminium, also with imidazole chelate (US 2007/0092753 A1) and quinoline-metal complexes, aminoquinoline-metal complexes, benzoquinoline-metal complexes, the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (e.g. DE 102007024850). Particularly preferred host materials are selected from the classes of the oligoarylenes, containing naphthalene, anthracene, benzanthracene and/or pyrene, or atropisomers of these compounds, the ketones, the phosphine oxides and the sulfoxides. Very particularly preferred host materials are selected from the classes of the oligoarylenes, containing anthracene, benzanthracene and/or pyrene, or atropisomers of these compounds. For the purposes of this invention, an oligoarylene is intended to be taken to mean a compound in which at least three aryl or arylene groups are bonded to one another.

Further preferred host materials for fluorescent emitter are selected, in particular, from compounds of the Formula 41

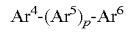  Formula 41 wherein
Ar$^4$, Ar$^5$, Ar$^6$ are on each occurrence, identically or differently, an aryl or heteroaryl group having 5 to 30 aromatic ring atoms, which may be substituted by one or more radicals and p is 1, 2, or 3,
the sum of the π-electrons in Ar$^4$, Ar$^5$ and Ar$^6$ is at least 30 if p=1 and is at least 36 if p=2 and is at least 42 if p=3.

It is particularly preferred in the host materials of the Formula 41 for the group Ar$^5$ to stand for anthracene, which may be substituted by one or more radicals R$^1$, and for the groups Ar$^4$ and Ar$^6$ to be bonded in the 9 and 10-positions. Very particularly preferably, at least one of the groups Ar$^4$ and/or Ar$^6$ is a condensed aryl group selected from 1- or 2-naphthyl, 2-, 3- or 9-phenanthrenyl or 2-, 3-, 4-, 5-, 6- or 7-benzanthracenyl, each of which may be substituted by one or more radicals R¹. Anthracene-based compounds are described in US 2007/0092753 A1 and US 2007/0252517 A1, for example 2-(4-methylphenyl)-9,10-di-(2-naphthyl)anthracene, 9-(2-naphthyl)-10-(1,1'-biphenyl)anthracene and 9,10-bis[4-(2,2-diphenylethenyl)phenyl]anthracene, 9,10-diphenylanthracene, 9,10-bis(phenylethynyl)anthracene and 1,4-bis(9'-ethynylanthracenyl)benzene. Preference is also given to host materials containing two anthracene units (US 2008/0193796 A1), for example 10,10'-bis[1,1',4',11"]terphenyl-2-yl-9,9'-bisanthracenyl.

Further preferred host materials are derivatives of arylamine, styrylamine, fluorescein, perynone, phthaloperynone, naphthaloperynone, diphenyl butadiene, tetraphenylbutadiene, cyclopentadienes, tetraphenylcyclopentadiene, pentaphenylcyclopentadiene, coumarine, oxadiazole, bisbenzoxazoline, oxazone, pyridine, pyrazine, imine, benzothiazole, benzoxazole, benzimidazole (US 2007/0092753 A1), for example 2,2',2"-(1,3,5-phenylene)tris[1-phenyl-1H-benzimidazole], aldazines, stilbene, styrylarylene derivatives, for example 9,10-bis[4-(2,2-diphenylethenyl)phenyl]anthracene, and distyrylarylene derivatives (U.S. Pat. No. 5,121,029), diphenylethylene, vinylanthracene, diaminocarbazole, pyran, thiopyran, diketopyrrolopyrrole, polymethine, mellocyanine, acridone, quinacridone, cinnamic acid esters and fluorescent dyes.

Particular preference is given to derivatives of arylamine and styrylamine, for example 4,4'-bis[N-(1-naphthyl)-N-(2-naphthyl)amino]biphenyl (TNB).

Preferred compounds with oligoarylene as hosts for fluorescent emitter are compounds as disclosed in, e.g., US 2003/0027016 A1, U.S. Pat. No. 7,326,371 B2, US 2006/043858 A, U.S. Pat. No. 7,326,371 B2, US 2003/0027016 A1, WO 2007/114358, WO 2008/145239, JP 3148176 B2, EP 1009044, US 2004/018383, WO 2005/061656 A1, EP 0681019B1, WO 2004/013073A1, U.S. Pat. No. 5,077,142, WO 2007/065678, and US 2007/0205412 A1. Particularly preferred oligoarylene-based compounds are compounds having the Formulae 42 to 48.

Formula 42

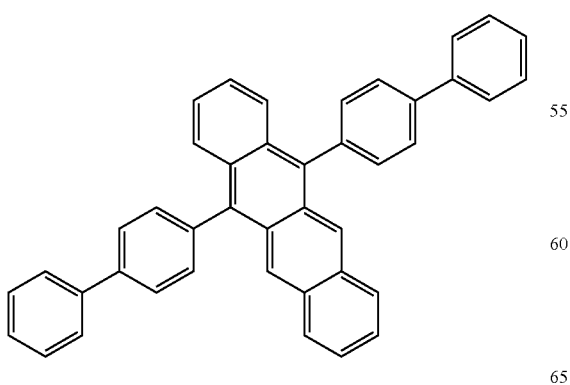

Formula 43

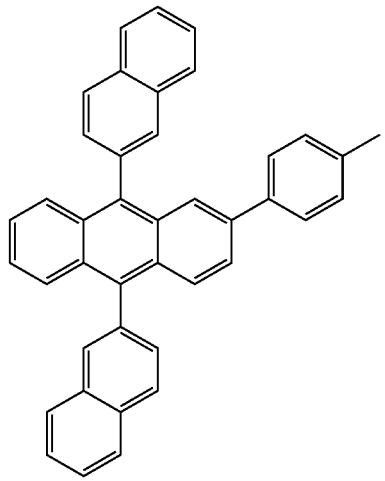

Formula 44

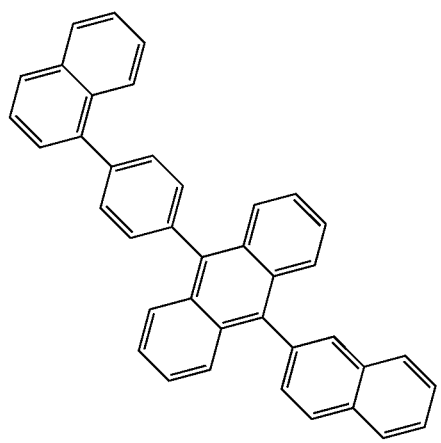

Formula 45

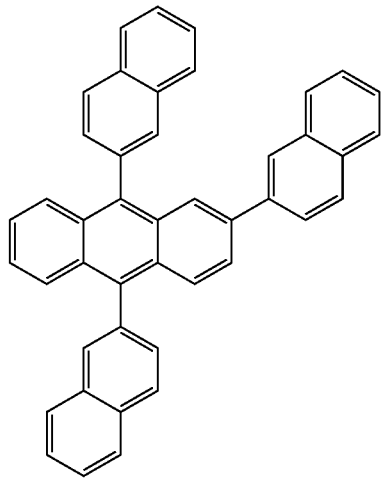

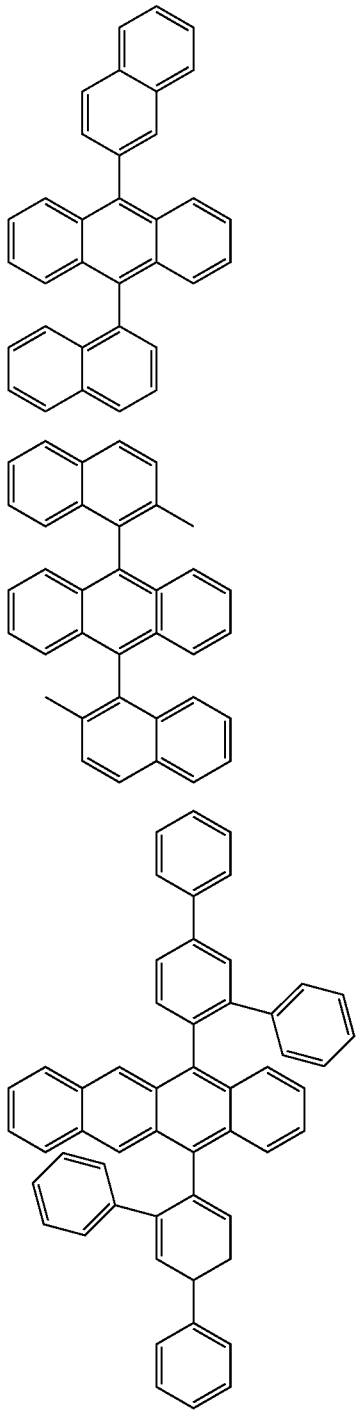

Formula 46

Formula 47

Formula 48

Further host materials for fluorescent emitter can be selected from spirobifluorene and derivates thereof, for example Spiro-DPVBi as disclosed in EP 0676461 and indenofluorene as disclosed in U.S. Pat. No. 6,562,485.

The preferred host materials for phosphorescent emitter, i.e. matrix materials, are selected from ketones, carbazoles, indolocarbazoles, triarylamines, indenofluorenes, fluorenes, spirobifluorenes, phenanthrenes, dehydrophenanthrenes, thiophenes, triazines, imidazoles and their derivatives. Some preferred derivatives are described below in more details.

If a phosphorescent emitter is employed the host material must fulfil rather different characteristics as compared to host materials used for fluorescent emitter. The host materials used for phosphorescent emitter are required to have a triplet level which is higher in energy as compared to the triplet level of the emitter. The host material can either transport electrons or holes or both of them. In addition, the emitter is supposed to have large spin-orbital coupling constants in order to facilitate singlet-triplet mixing sufficiently. This can be enabled by using metal complexes.

Preferred matrix materials are N,N-biscarbazolylbiphenyl (CBP), carbazole derivatives (for example in accordance with WO 2005/039246, US 2005/0069729, JP 2004/288381, EP 1205527 or DE 102007002714), azacarbazoles (for example in accordance with EP 1617710, EP 1617711, EP 1731584, JP 2005/347160), ketones (for example in accordance with WO 2004/093207), phosphine oxides, sulfoxides and sulfones (for example in accordance with WO 2005/003253), oligophenylenes, aromatic amines (for example in accordance with US 2005/0069729), bipolar matrix materials (for example in accordance with WO 2007/137725), silanes (for example in accordance with WO 2005/111172), 9,9-diarylfluorene derivatives (e.g. in accordance with DE 102008017591), azaboroles or boronic esters (for example in accordance with WO 2006/117052), triazole derivatives, oxazoles and oxazole derivatives, imidazole derivatives, polyarylalkane derivatives, pyrazoline derivatives, pyrazolone derivatives, distyrylpyrazine derivatives, thiopyran dioxide derivatives, phenylenediamine derivatives, tertiary aromatic amines, styrylamines, indoles, anthrone derivatives, fluorenone derivatives, fluorenylidenemethane derivatives, hydrazone derivatives, silazane derivatives, aromatic dimethylidene compounds, porphyrin compounds, carbodiimide derivatives, diphenylquinone derivatives, phthalocyanine derivatives, metal complexes of 8 hydroxyquinoline derivatives, such as, for example, $Alq_3$, the 8 hydroxyquinoline complexes may also contain triarylaminophenol ligands (US 2007/0134514 A1), various metal complex-polysilane compounds with metal phthalocyanine, benzoxazole or benzothiazole as ligand, hole-conducting polymers, such as, for example, poly(N-vinylcarbazole) (PVK), aniline copolymers, thiophene oligomers, polythiophenes, polythiophene derivatives, polyphenylene derivatives, polyfluorene derivatives.

Further particularly preferred matrix materials are selected from compounds comprising indolocarbazoles and their derivatives (e.g. Formulae 49 to 55), as disclosed for examples in DE 102009023155.2, EP 0906947B1, EP 0908787B1, EP 906948B1, WO 2008/056746A1, WO 2007/063754A1, WO 2008/146839A1, and WO 2008/149691A1.

Formula 49

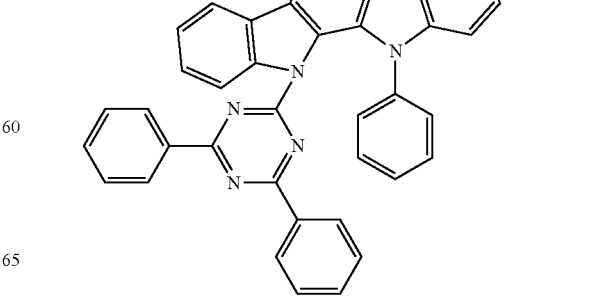

Formula 50
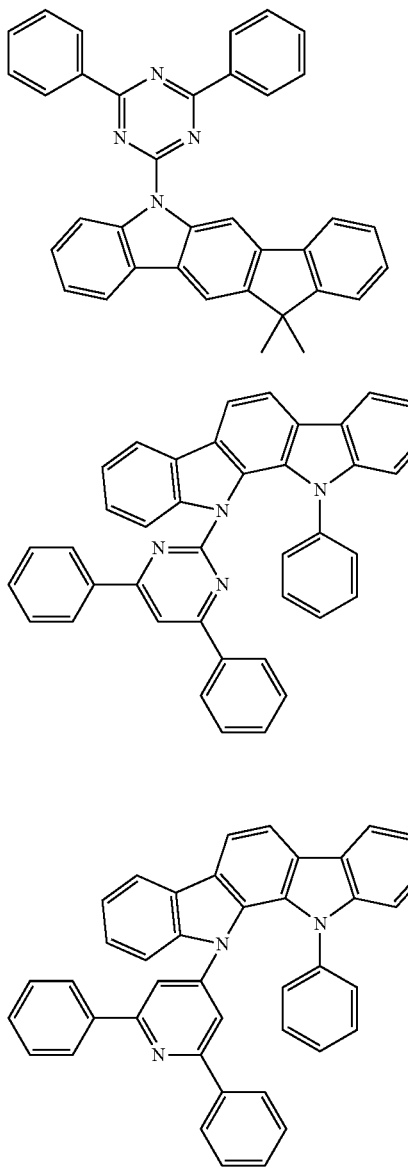
Formula 51
Formula 52
Formula 53
Formula 54
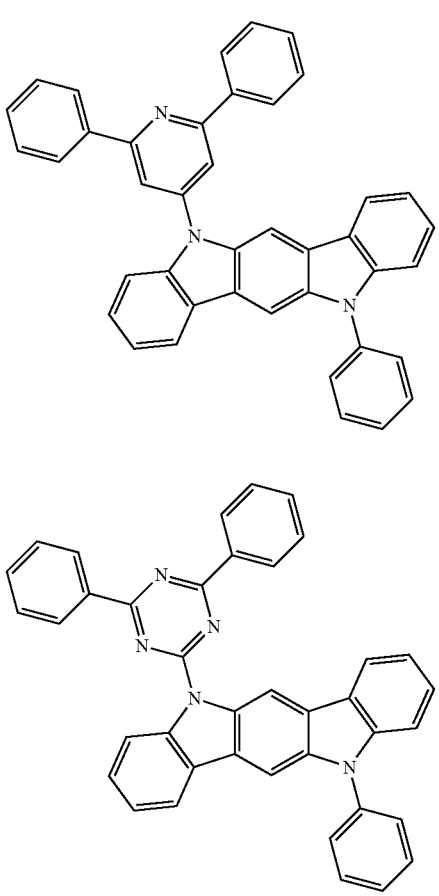
Formula 55
Examples of preferred carbazole derivatives are, 1,3-N,N-dicarbazolebenzene (=9,9'-(1,3-phenylene)bis-9H-carbazole) (mCP), 9,9'-(2,2'-dimethyl[1,1'-biphenyl]-4,4'-diyl)bis-9H-carbazole (CDBP), 1,3-bis(N,N'-dicarbazole)benzene (=1,3-bis(carbazol-9-yl)benzene), PVK (polyvinylcarbazole), 3,5-di(9H-carbazol-9-yl)biphenyl and compounds of the Formulae 56 to 60.
Formula 56
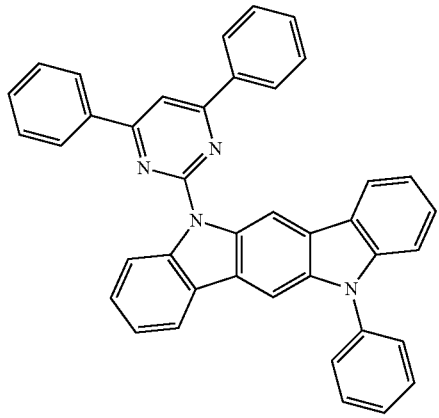
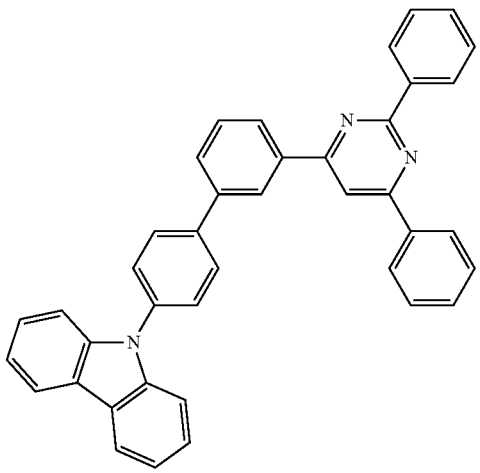

Formula 57
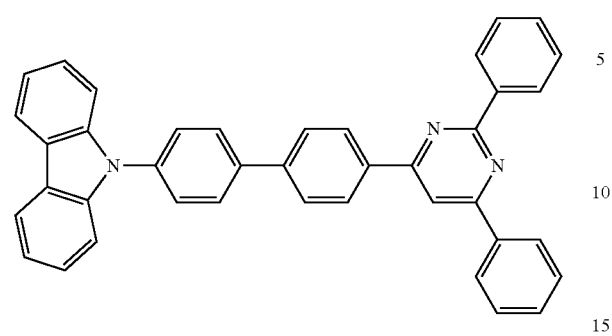
Formula 61
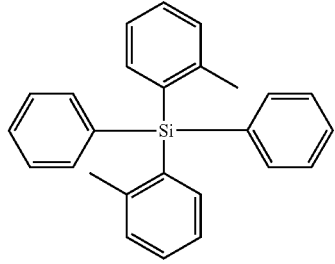
Formula 58
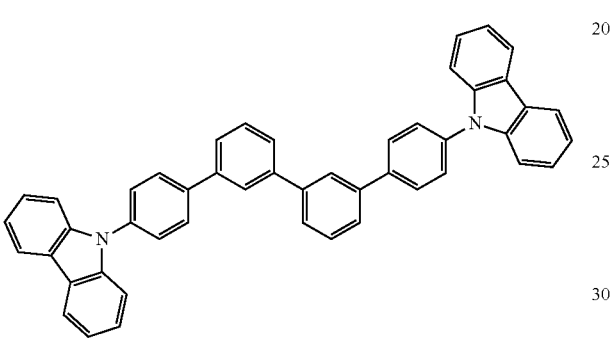
Formula 62
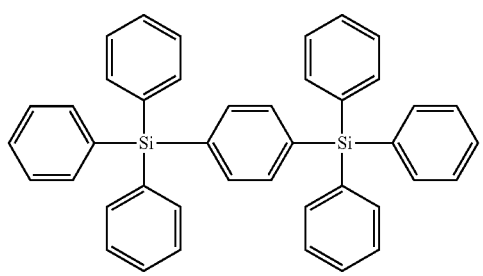
Formula 63
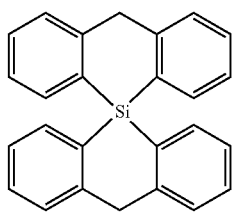
Formula 59
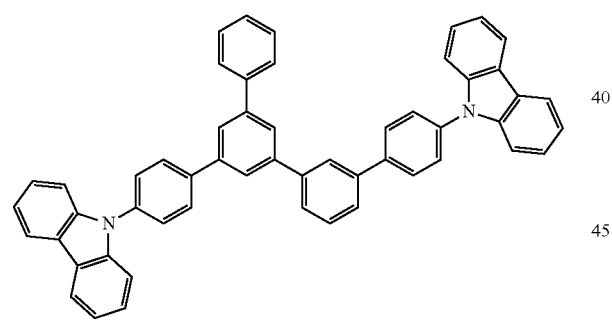
Formula 64
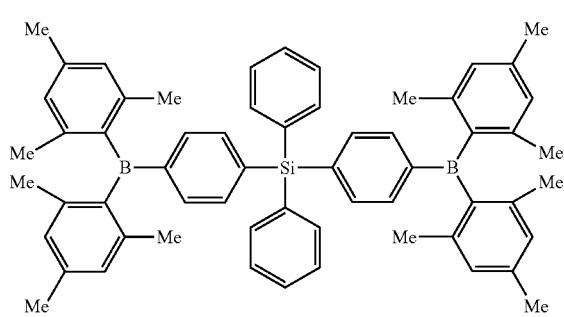
Formula 60
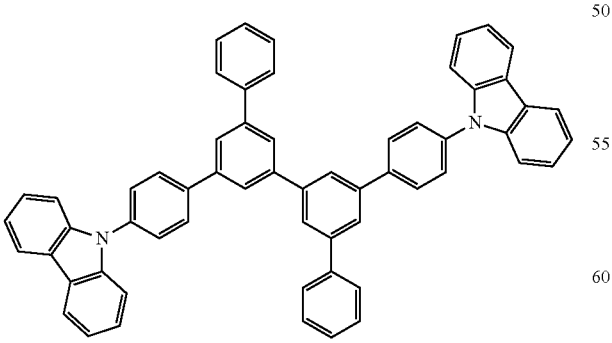
Formula 65
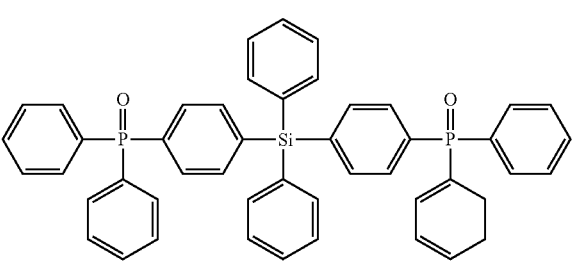
Preferred Si tetraaryl compounds are, for example, (US 2004/0209115, US 2004/0209116, US 2007/0087219 A1, US 2007/0087219 A1) the compounds of the Formulae 61 to 66.

Formula 66

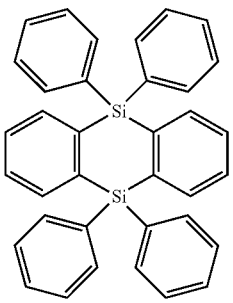

A particularly preferred matrix for phosphorescent dopants is the compound of Formula 67 (EP 652273 B1)

Formula 67

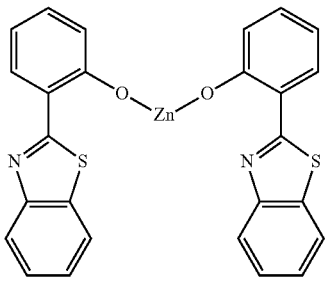

Further particularly preferred matrix materials for phosphorescent dopants are selected from compounds of the general Formula 68 (EP 1923448A1).

$$[M(L)_2]_n$$ Formula 68 wherein M, L, and n are defined as in the reference. Preferably M is Zn, and L is quinolinate, and n is 2, 3 or 4. Very particularly preferred are $[Znq_2]_2$, $[Znq_2]_3$, and $[Znq_2]_4$.

Preference is given to co-hosts selected from metal oxinoid complexes whereby lithium quinolate (Liq) or $Alq_3$ are particularly preferred.

The emitter compound is required to have a smaller band gap as compared to the host compound. In general, smaller band gaps can be achieved by extending the π-electron system of conjugated molecular systems. Emitter compounds tend, therefore, to have more extended conjugated π-electron systems than host molecules. Many examples have been published, e.g. styrylamine derivatives as disclosed in JP 2913116B and WO 2001/021729 A1, and indenofluorene derivatives as disclosed in WO 2008/006449 and WO 2007/140847.

Another subject of the present invention relates to said OLEFC comprising at least one further functional material selected from hole transport materials (HTM), hole injection materials (HIM), electron transport materials (ETM), and electron injection materials (EIM).

The organic functional materials can be selected from hole transport materials (HTM). A HTM is characterized in that it is a material or unit capable of transporting holes (i.e. positive charges) injected from a hole injecting material or an anode. A HTM has usually high HOMO, typically higher than −5.4 eV. In many cases, HIM can functions also as HTM, depending on the adjacent layer.

The OLEFC according to the present invention comprises 4, preferably 3, particularly preferably 2, and very particularly preferably 1 HTMs.

The organic functional materials can be selected from hole injection materials (HIM). A HIM refers to a material or unit capable of facilitating holes (i.e. positive charges) injected from an anode into an organic layer. Typically, a HIM has a HOMO level comparable to or higher than the work function of the anode, i.e. −5.3 eV or higher.

The OLEFC according to the present invention comprises 4, preferably 3, particularly preferably 2, and very particularly preferably 1 HIMs.

The organic functional materials can be selected from electron transport materials (ETM). An ETM refers to a material capable of transporting electrons (i.e. negative charges) injected from an EIM or a cathode. The ETM has usually a low LUMO, typically lower than −2.7 eV. In many The OLEFC according to the present invention comprises 4, preferably 3, particularly preferably 2, and very particularly preferably 1 ETMs.

The organic functional materials can be selected from electron injection materials (EIM). An EIM refers to a material capable of facilitating electrons (i.e. negative charges) injected from cathode into an organic layer. The EIM usually has a LUMO level comparable to or lower than the working function of cathode. Typically, the EIM has a LUMO lower than −2.6 eV.

The OLEFC according to the present invention comprises 4, preferably 3, particularly preferably 2, and very particularly preferably 1 EIMs.

In principle any HTM known to one skilled in the art can be employed in OLEFCs according to the present invention. Further to HTM mentioned elsewhere herein, HTM is preferably selected from amines, triarylamines, thiophenes, carbazoles, phthalocyanines, porphyrines, isomers and derivatives thereof. HTM is particularly preferably selected from amines, triarylamines, thiophenes, carbazoles, phthalocyanines, and porphyrines.

Suitable materials for hole-transporting layers are phenylenediamine derivatives (U.S. Pat. No. 3,615,404), arylamine derivatives (U.S. Pat. No. 3,567,450), amino substituted chalcone derivatives (U.S. Pat. No. 3,526,501), styrylanthracene derivatives (JP A 56-46234), polycyclic aromatic compounds (EP 1009041), polyarylalkane derivatives (U.S. Pat. No. 3,615,402), fluorenone derivatives (JP A 54-110837), hydrazone derivatives (U.S. Pat. No. 3,717,462), stilbene derivatives (JP A 61-210363), silazane derivatives (U.S. Pat. No. 4,950,950), polysilanes (JP A 2-204996), aniline copolymers (JP A 2-282263), thiophene oligomers, polythiophenes, PVK, polypyrroles, polyanilines and further copolymers, porphyrin compounds (JP A 63-2956965), aromatic dimethylidene-type compounds, carbazole compounds, such as, for example, CDBP, CBP, mCP, aromatic tertiary amine and styrylamine compounds (U.S. Pat. No. 4,127,412), and monomeric triarylamines (U.S. Pat. No. 3,180,730). Even more triarylamino groups may also be present in the molecule.

Preference is given to aromatic tertiary amines containing at least two tertiary amine units (U.S. Pat. No. 4,720,432 and U.S. Pat. No. 5,061,569), such as, for example, 4,4'-bis[N-(1-naphthyl)-N-phenylamino]biphenyl (NPD) (U.S. Pat. No. 5,061,569) or MTDATA (JP A 4-308688), N,N,N',N'-tetra(4-biphenyl)diaminobiphenylene (TBDB), 1,1-bis(4-di-p-tolylaminophenyl)cyclohexane (TAPC), 1,1-bis(4-di-p-tolylaminophenyl)-3-phenylpropane (TAPPP), 1,4-bis[2-[4-[N,N-di(p-tolyl)amino]phenyl]vinyl]benzene (BDTAPVB), N,N,N',N'-tetra-p-tolyl-4,4'-diaminobiphenyl (TTB), TPD, N,N,N',N'-tetraphenyl-4,4'''-diamino-1,1':4',1'':4'',1'''-quaterphenyl, likewise tertiary amines containing carbazole units, such as, for example, 4 (9H-carbazol-9-yl)-N,N-bis[4-(9H-carbazol- 9-yl)phenyl]benzeneamine (TCTA). Preference is likewise given to hexaazatriphenylene compounds in accordance with US 2007/0092755 A1.

Particular preference is given to the following triarylamine compounds of the Formulae 69 to 74, which may also be substituted, and as disclosed in EP 1162193 A1, EP 650955 A1, Synth. Metals 1997, 91(1-3), 209, DE 19646119 A1, WO 2006/122630 A1, EP 1860097 A1, EP 1834945 A1, JP 08053397 A, U.S. Pat. No. 6,251,531 B1, and WO 2009/041635.

Formula 69

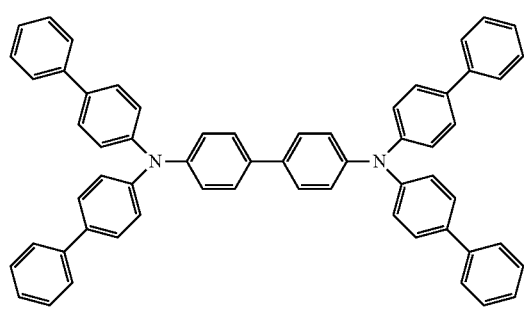

Formula 70

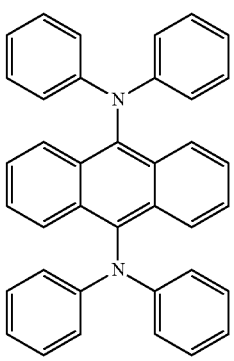

Formula 71

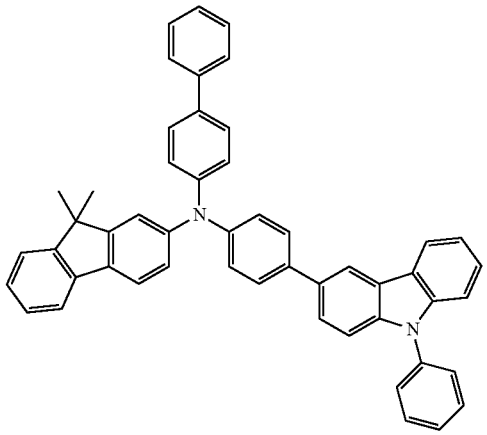

Formula 72

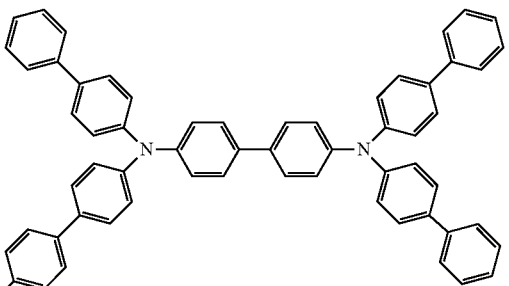

Formula 73

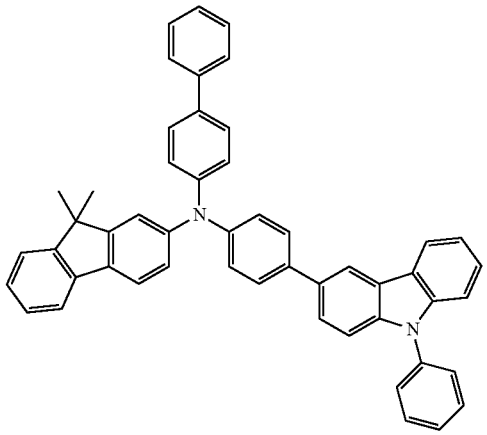

Formula 74

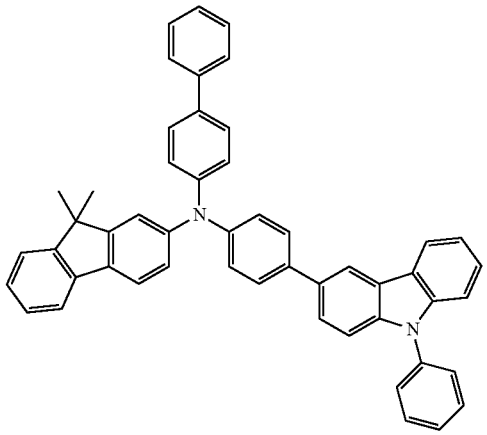

Further to HIMs mentioned elsewhere herein, suitable HIMs are phenylenediamine derivatives (U.S. Pat. No. 3,615,404), arylamine derivatives (U.S. Pat. No. 3,567,450), amino-substituted chalcone derivatives (U.S. Pat. No. 3,526,501), styrylanthracene derivatives (JP Showa 54 (1979) 110837), hydrazone derivatives (U.S. Pat. No. 3,717,462), acylhydrazones, stilbene derivatives (JP Showa 61 (1986) 210363), silazane derivatives (U.S. Pat. No. 4,950,950), polysilane compounds (JP Heisei 2 (1990) 204996), PVK and other electrically conductive macromolecules, aniline-based copolymers (JP Heisei 2 (1990) 282263), electrically conductive, macromolecular thiophene oligomers (JP Heisei 1 (1989) 211399), PEDOT:PSS (spin-coated polymer), plasma-deposited fluorocarbon polymers (U.S. Pat. No. 6,127,004, U.S. Pat. No. 6,208,075, U.S. Pat. No. 6,208,077), porphyrin compounds (JP Showa 63 (1988) 2956965, U.S. Pat. No. 4,720,432), aromatic tertiary amines and styrylamines (U.S. Pat. No. 4,127,412), triphenylamines of the benzidine type, triphenylamines of the styrylamine type, and triphenylamines of the diamine type. Arylamine dendrimers can also be used (JP Heisei 8 (1996) 193191), as can phthalocyanine derivatives, naphthalocyanine derivatives, or butadiene derivatives, are also suitable.

Preferably, the HIM is selected from monomeric organic compound comprising amines, triarylamines, thiophenes, carbazoles, phthalocyanines, porphyrines and their derivatives.

Particular preference is given to the tertiary aromatic amines (US 2008/0102311 A1), for example N,N'-diphenyl-N,N'-di(3-tolyl)benzidine (=4,4'-bis[N-3-methylphenyl]-N-phenylamino)biphenyl (NPD) (U.S. Pat. No. 5,061,569), N,N'-bis(N,N'-diphenyl-4-aminophenyl)-N,N-diphenyl-4,4'-diamino-1,1'-biphenyl (TPD 232) and 4,4',4"-tris[3-methylphenyl)phenylamino]-triphenylamine (MTDATA) (JP Heisei 4 (1992) 308688) or phthalocyanine derivatives (for example H2Pc, CuPc, CoPc, NiPc, ZnPc, PdPc, FePc, MnPc, ClAlPc, ClGaPc, ClInPc, ClSnPc, Cl2SiPc, (HO)AlPc, (HO)GaPc, VOPc, TiOPc, MoOPc, GaPc-O-GaPc).

Particular preference is given to the following triarylamine compounds of the Formulae 75 (TPD 232), 2, 3, and 4, which may also be substituted, and further compounds as disclosed in U.S. Pat. No. 7,399,537 B2, US 2006/0061265 A1, EP 1661888 A1, and JP 08292586 A.

Further compounds suitable as hole injection material are disclosed in EP 0891121 A1 and EP 1029909 A1.

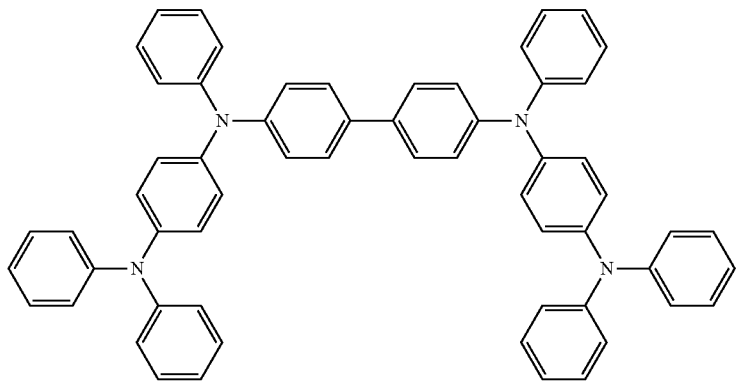

Formula 75

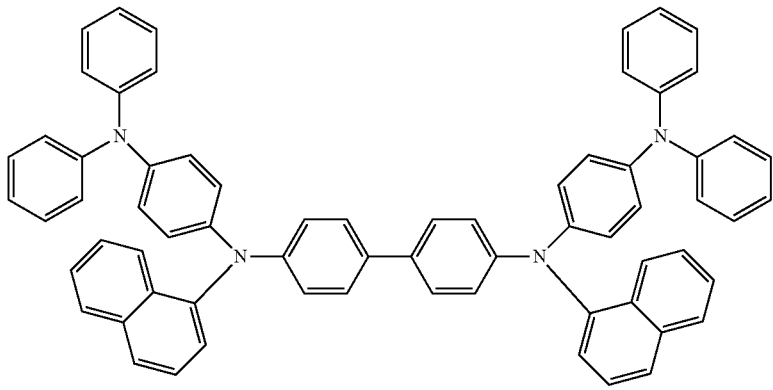

Formula 76

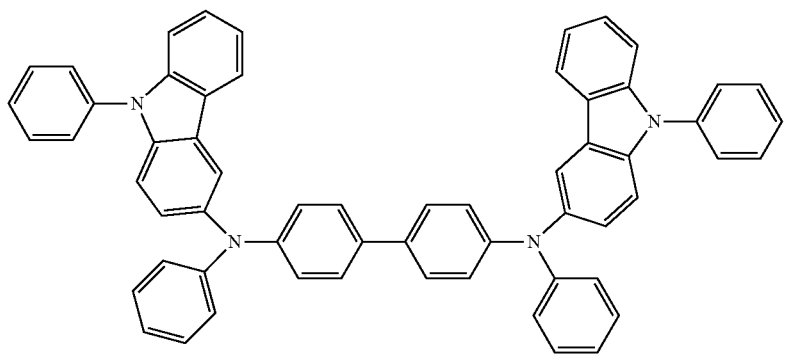

Formula 77

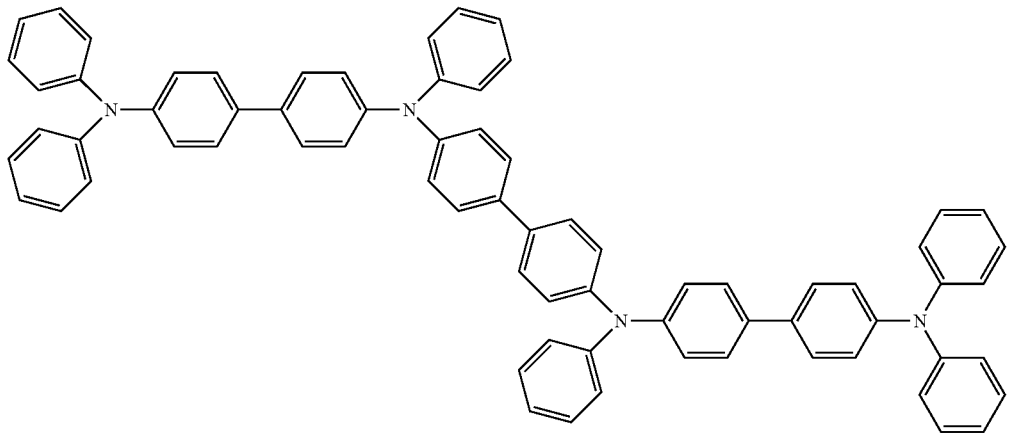

Formula 78

In principle any ETM known to one skilled in the art can be employed according to the present invention. Further to ETM mentioned elsewhere herein, suitable ETMs are selected from imidazoles, pyridines, pyrimidines, pyridazines, pyrazines, oxadiazoles, chinolines, chinoxalines, anthracenes, benzanthracenes, pyrenes, perylenes, benzimidazoles, triazines, ketones, phosphinoxides, phenazines, phenanthrolines, triarylboranes, isomers and derivatives thereof.

Further suitable ETMs are selected from imidazoles, pyridines, pyrimidines, pyridazines, pyrazines, oxadiazoles, chinolines, chinoxalines, anthracenes, benzanthracenes, pyrenes, perylenes, benzimidazoles, triazines, ketones, phosphinoxides, phenazines, phenanthrolines, and triarylboranes.

Further suitable ETMs are selected from metal chelates of 8 hydroxyquinoline (for example Liq, Alq$_3$, Gaq$_3$, Mgq$_2$, Znq$_2$, Inq$_3$, Zrq$_4$), Balq, 4 azaphenanthrene-5-ol/Be complexes (U.S. Pat. No. 5,529,853 A; e.g. Formula 79), butadiene derivatives (U.S. Pat. No. 4,356,429), heterocyclic optical brighteners (U.S. Pat. No. 4,539,507), benzazoles, such as, for example, 1,3,5-tris(2-N-phenylbenzimidazolyl)benzene (TPBI) (U.S. Pat. No. 5,766,779, Formula 80), 1,3,5-triazines, pyrenes, anthracenes, tetracenes, fluorenes, spirobifluorenes, dendrimers, tetracenes, for example rubrene derivatives, 1,10-phenanthroline derivatives (JP 2003/115387, JP 2004/311184, JP 2001/267080, WO 2002/043449), silacyl-cyclopentadiene derivatives (EP 1480280, EP 1478032, EP 1469533), pyridine derivatives (JP 2004/200162 Kodak), phenanthrolines, for example BCP and Bphen, also a number of phenanthrolines bonded via biphenyl or other aromatic groups (US 2007/0252517 A1) or phenanthrolines bonded to anthracene (US 2007/0122656 A1, e.g. Formulae 81 and 82), 1,3,4-oxadiazoles, for example Formula 83, triazoles, for example Formula 84, triarylboranes, for example also with Si (e.g. Formula 64), benzimidazole derivatives and other N heterocyclic compounds (cf. US 2007/0273272 A1), silacyclopentadiene derivatives, borane derivatives, Ga oxinoid complexes.

Preference is given to 2,9,10-substituted anthracenes (with 1- or 2-naphthyl and 4- or 3-biphenyl) or molecules which contain two anthracene units (US 2008/0193796 A1).

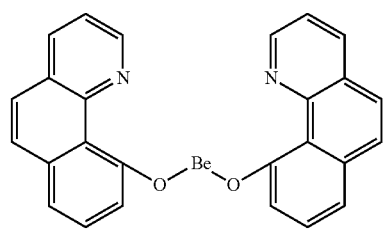

Formula 79

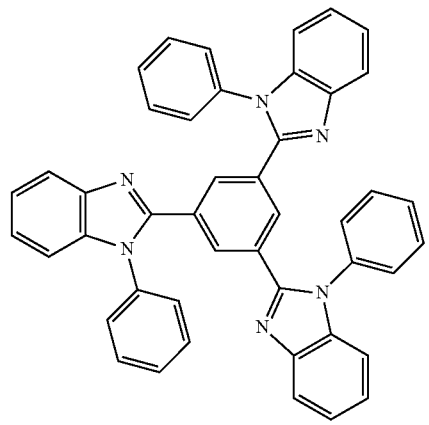

Formula 80

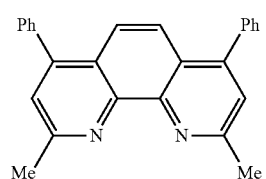

Formula 81

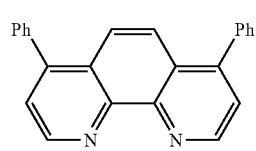

Formula 82

Formula 83

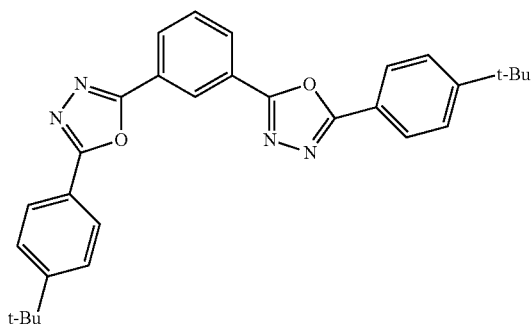

Formula 86

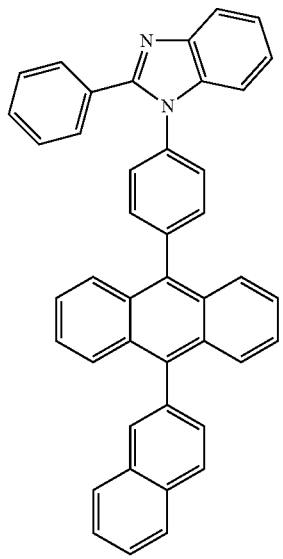

Formula 87

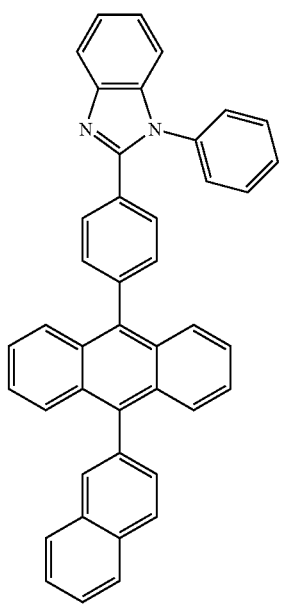

Formula 84

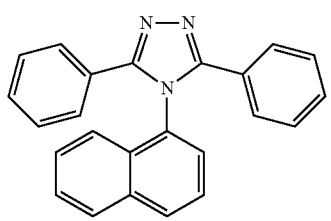

Preference is likewise given to anthracene-benzimidazole derivatives, such as, for example, the compounds of Formulae 85 to 87, and as disclosed in, e.g., U.S. Pat. No. 6,878,469 B2, US 2006/147747 A, and EP 1551206 A1.

Formula 85

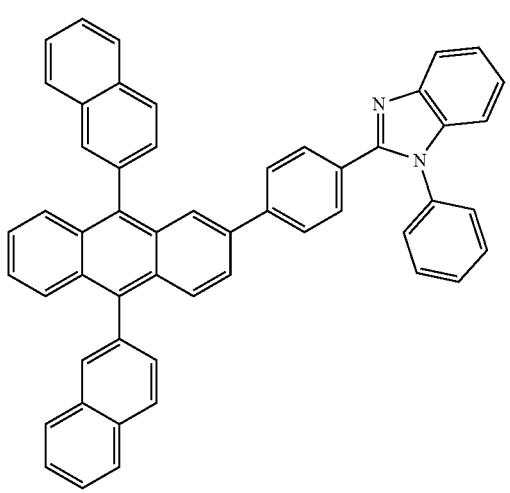

In principle any EIM known to one skilled in the art can be employed according to the present invention. Further to EIM mentioned elsewhere herein, suitable EIM comprises at least one organic compound selected from metal complexes of 8-hydroxyquinoline, heterocyclic organic compounds, fluorenones, fluorenylidene methane, perylenetetracarboxylic acid, anthraquinone dimethanes, diphenoquinones, anthrones, anthraquinonediethylene-diamines, isomers and derivates thereof can be used according to the invention.

Metal complexes of 8 hydroxyquinoline, such as, for example, $Alq_3$ and $Gaq_3$, can be used as EIM for electron-injection layers. A reducing doping with alkali metals or alkaline-earth metals, such as, for example, Li, Cs, Ca or Mg, at the interface to the cathode is advantageous. Preference is given to combinations which include Cs, for example Cs and Na, Cs and K, Cs and Rb or Cs, Na and K.

Heterocyclic organic compounds, such as, for example, 1,10-phenanthroline derivatives, benzimidazoles, thiopyran dioxides, oxazoles, triazoles, imidazoles or oxadiazoles, are likewise suitable. Examples of suitable five-membered rings containing nitrogen are oxazoles, thiazoles, oxadiazoles, thiadiazoles, triazoles, and compounds which are disclosed in US 2008/0102311 A1.

Preferred EIMs are selected from compounds with the Formulae 88 to 90, which may be substituted or unsubstituted.

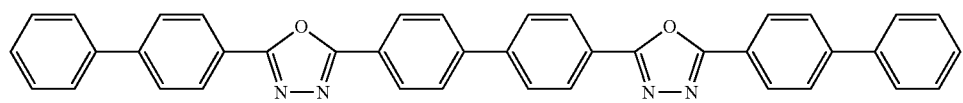

Formula 88

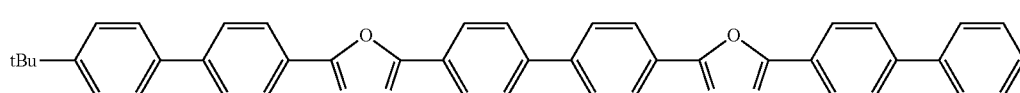

Formula 89

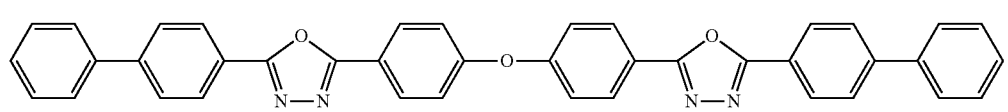

Formula 90

Organic compounds, such as fluorenones, fluorenylidene methane, perylenetetracarboxylic acid, anthraquinone dimethanes, diphenoquinones, anthrones and anthraquinonediethylenediamines, can also be employed, for example

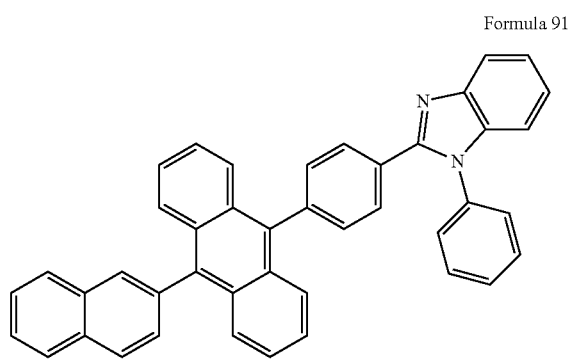

Formula 91

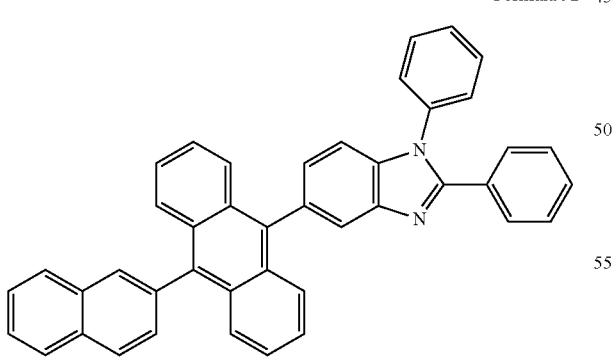

Formula 92

The OLEFC according to the present invention can comprise at least one ionic specie. Preferably the at least one ionic specie is mobile. The at least one ionic specie can be selected from small molecules, polymers, oligomers, dendrimers, blends, and/or mixtures thereof.

In a preferred embodiment the OLEFC can comprise at least one ionic organic electroluminescent compound in form of $K^+A^-$, wherein either $K^+$ or $A^-$ is an organic emissive material wherein $K^+$ and $A^-$ represent a cation and an anion, respectively. Preferably the OLEFC comprises 3, particularly preferably 2, and very particularly preferably 1 compound of the formula $K^+A^-$.

Preferably the ionic materials are soluble in the same solvent as the organic emissive material. This easily allows the preparation of a mixture comprising the said emitter material(s) and the ionic material(s). Typically organic emissive materials are soluble in common organic solvents, such as toluene, anisole, chloroform.

Preferably, the said ionic material is solid at room temperature and particularly preferably, the said ionic material is solid at room temperature and getting softer between 30 to 37° C.

Preferably the said ionic species is a cation. Suitable inorganic cations $K^+$ can be selected from, for example, $K^+$ (potassium) and $Na^+$. Suitable organic cations $K^+$ can be selected from ammonium-, phosphonium, thiouronium-, guanidinium cations as shown in Formulae 93 to 97 or heterocyclic cations as shown in Formulae 98 to 125.

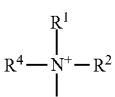

Formula 93

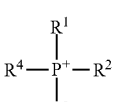

Formula 94

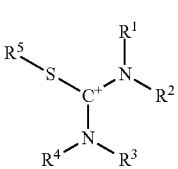

Formula 95

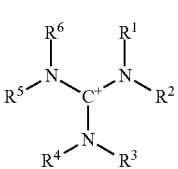

Formula 96

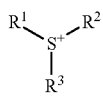

Formula 97 wherein $R^1$ to $R^6$ can be, independently from each other, selected from linear or hyperbranched alkyl rests with 1 to 20 C-atoms, linear or hyperbranched alkenyl rests with 2 to 20 C-atoms and one or more non-conjugated double bonds, linear or hyperbranched alkinyl rests with 2 to 20 C-atoms and one or more non-conjugated triple bond, saturated, partly saturated or completely saturated cycloalkyl with 3 to 7 C-atoms, which can further be substituted with alkyl groups having 1 to 6 C-atoms, wherein one or more substituents R may be partly or completely substituted with halogen, particularly with —F and/or —Cl, or partly substituted with —OR', —CN, —C(O)OH, —C(O)NR'$_2$, —SO$_2$NR'$_2$, —SO$_2$OH, —SO$_2$X, —NO$_2$, wherein one or two non adjacent and non α-carbon atoms of $R^1$ to $R^6$ can be substituted with groups selected from —O—, —S—, —S(O)—, —SO$_2$—, —N$^+$R'$_2$, —C(O)NR'—, —SO$_2$NR'—, and —P(O)R'—, wherein R'=H, unsubstituted, partly or completely with —F substituted C1 to C6-alkyl, C3 to C7-cycloalkyl, unsubstituted or substituted phenyl and X=halogen.

In Formula 93 $R^1$ to $R^4$ can be H, with the provision that at least one of the rests R' to $R^4$ is not H. In Formula 94 $R^1$ to $R^4$ can be H and NR'$_2$, wherein R' is defined as above. In Formula 95 $R^1$ to $R^5$ can be H. In Formula 96 $R^1$ to $R^6$ can be H, CN, and NR'$_2$, wherein R' is defined as above.

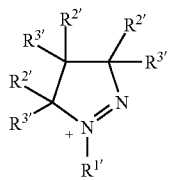

Formula 102

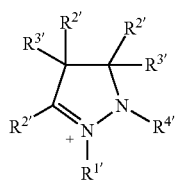

Formula 103

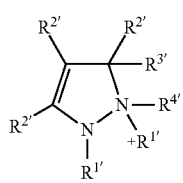

Formula 104

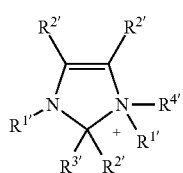

Formula 105

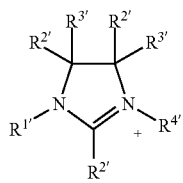

Formula 106

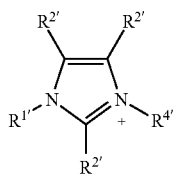

Formula 98

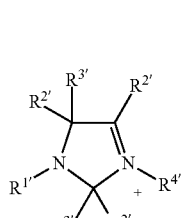

Formula 107

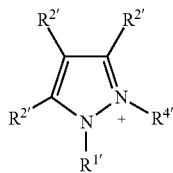

Formula 99

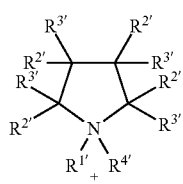

Formula 108

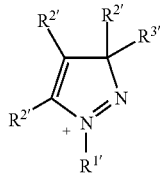

Formula 100

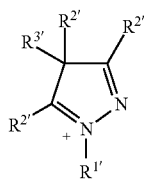

Formula 101

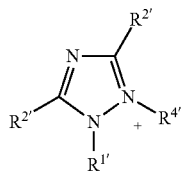

Formula 109

-continued
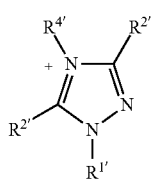
Formula 110
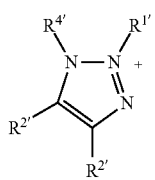
Formula 111
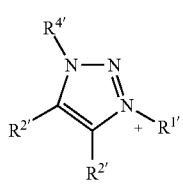
Formula 112
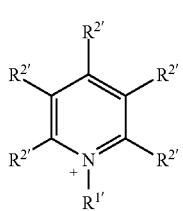
Formula 113
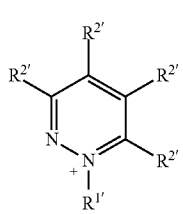
Formula 114
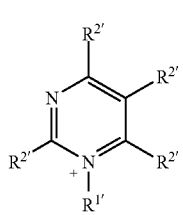
Formula 115
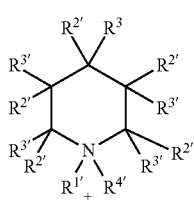
Formula 116
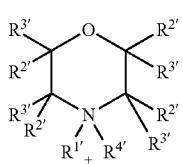
Formula 117
-continued
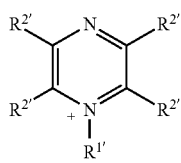
Formula 118
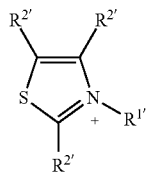
Formula 119
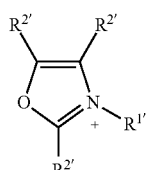
Formula 120
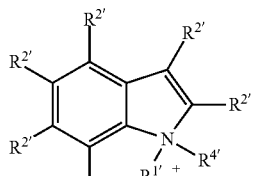
Formula 121
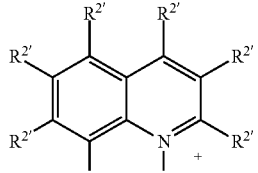
Formula 122
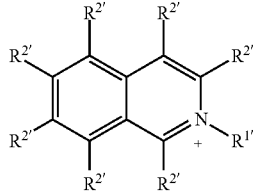
Formula 123
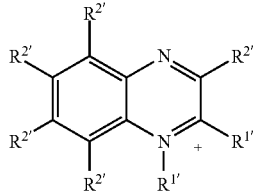
Formula 124
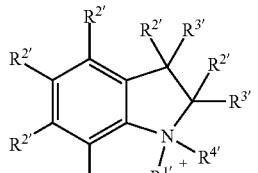
Formula 125
Wherein the substituents $R^{1'}$ to $R^{4'}$ are independently from each other selected from H, CN, linear and branched alkyl rest with 1 to 20 C-atoms, linear or branched alkenyl rest with 2 to 20 C-atoms and one or more non conjugated double bonds, linear or branched alkinyl rest with 2 to 20 C-atoms and one or more non conjugated triple bonds, partly or completely non saturated cycloalkyl rest with 3 to 7 C-atoms which can be substituted with alkyl rests with 1 to 6 C-atoms, saturated and partly or completely non saturated heteroaryls, heteroaryl-$C_1$-$C_6$-alkyl, or alkyl-$C_1$-$C_6$-alkyl, wherein the substituents $R^{1'}$, $R^{2'}$, $R^{3'}$ and/or $R^{4'}$ together can form a ring, wherein one or more of the substituents $R^{1'}$ to $R^{4'}$ can partly or completely be substituted with halogen, particularly with —F and/or —Cl, and —OR', —CN, —C(O)OH, —C(O)NR'$_2$, —SO$_2$NR'$_2$, —C(O)X, —SO$_2$OH, —SO$_2$X, —NO$_2$, wherein the substituents $R^{1'}$ and $R^{4'}$ are not substituted with halogen at the same time, wherein one or two carbon atoms of the substituents $R^{1'}$ and $R^{2'}$, which are non adjacent or bound to an heteroatom, can be substituted by a group selected from —O—, —S—, —S(O)—, —SO$_2$—, —N$^+$R'$_2$—, —C(O)NR'—, —SO$_2$NR'—, and —P(O)R'— wherein R'=H, unsubstituted, partly or completely with —F substituted alkyl with 1 to 6 C-atoms, cycloalkyl with 3 to 7 C-atoms, unsubstituted or substituted phenyl and X=halogen.

Preference is given to $R^{2'}$ selected from —OR', —NR'$_2$, —C(O)OH, —C(O)NR'$_2$, —SO$_2$NR'$_2$)—SO$_2$OH, —SO$_2$X, and —NO$_2$.

Further preferred ionic materials are disclosed in, e.g., US 2007/0262694 A1.

Further particularly preferred ionic materials comprise a cation having a structure represented by Formula 126. They include N,N,N-trimethylbutyl ammonium ion, N-ethyl-N,N-dimethyl-propyl ammonium ion, N-ethyl-N,N-dimethylbutyl ammonium ion, N,N,-dimethyl-N-propylbutyl ammonium ion, N-(2-methoxyethyl)-N,N-dimethylethyl ammoniumion, 1-ethyl-3-methyl imidazolium ion, 1-ethyl-2,3-dimethyl imidazoliun ion, 1-ethyl-3,4-dimethyl imidazolium ion, 1-ethyl-2,3,4-trimethyl imidazolium ion, 1-ethyl-2,3,5-trimethyl imidazolium ion, N-methyl-N-propyl pyrrolidinium ion, N-butyl-N-methyl pyrrolidinium ion, N-sec-butyl-N-methylpyrrolidinium ion, N-(2-methoxyethyl)-N-methylpyrrolidinium ion, N-(2-ethoxyethyl)-N-methylpyrrolidinium ion, N-methyl-N-propyl piperidinium ion, N-butyl-N-methyl pipridinium ion, N-sec-butyl-N-methylpiperidinium ion, N-(2-methoxyethyl)-N-methyl piperidiniumion and N-(2-ethoxyethyl)-N-methyl piperidinium ion.

Formula 126

Very particularly preferred is N-methyl-N-propyl piperidinium.

Particularly preferred ionic material is a compound selected from the group of ionic compounds, which are soluble in common organic solvents such as toluene, anisole, and chloroform, consisting of methyltrioctylammonium trifluoromethane-sulfonate (MATS), 1-methyl-3-octylimidazolium octylsulfate, 1-butyl-2,3-dimethylimidazolium octylsulfate, 1-octadecyl-3-methylimidazolium bis(trifluoromethylsulfonyl)imide, 1-octadecyl-3-methylimidazolium tris(pentafluoroethyl) trifluorophosphate, 1,1-dipropylpyrrolidimium bis(trifluoromethylsulfonyl)imide, trihexyl(tetradecyl) phosphonium bis(1,2-bezenediolato(2-)-O,O')borate, and N,N,N',N',N',N'-pentamethyl-N'-propylguanidinium trifluoromethanesulfonate.

Further preferred cations are selected from compounds of one of the general Formulae 127 to 132

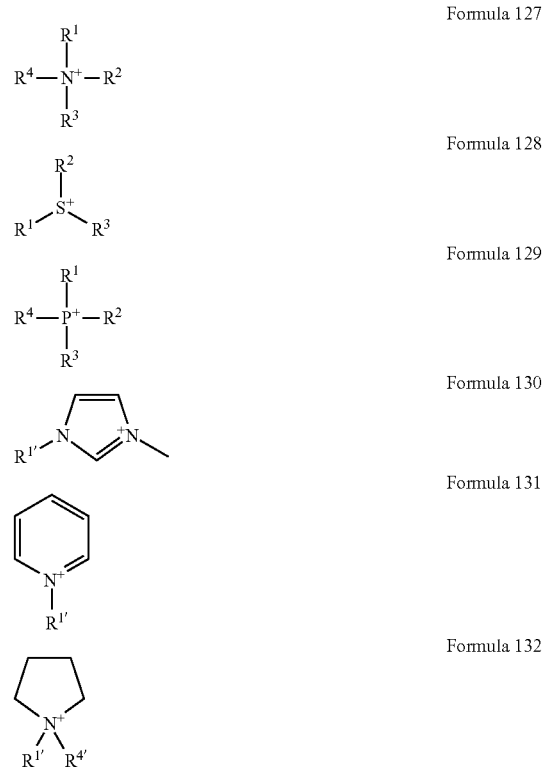

Wherein $R^1$ to $R^4$ are defined as in Formulae 93, 94, and 97, and $R^{1'}$ and $R^{4'}$ as in Formulae 98, 113, and 108.

Further preferred ionic materials suitable for the composition and device according to the present invention is a compound wherein one of $K^+$ or K is covalently bounded to a polymer backbone.

Further particularly preferred ionic materials suitable for the composition and device according to the present invention are conjugated polyelectrolytes (CPE) with an electronically delocalized backbone with pendant groups bearing ionic functionalities. Examples for CPEs are give by C. V. Hoven et al., in Adv. Mater. 2008, 20, 3793-3810.

Further preferred ionic materials suitable for use in an OLEFC according to the present invention are selected from compounds wherein one of $K^+$ or $A^-$ is an organic emissive material, which can be selected from small molecule and polymeric emissive materials as described elsewhere within the present invention.

Preferably the said ionic species is an anion. Suitable anions $A^-$ can be selected from $[HSO_4]^-$, $[SO_4]^{2-}$, $[NO_3]^-$, $[BF_4]^-$, $[(R_F)BF3]^-$, $[(R_F)_2BF_2]^-$, $[(RF)_3BF]^-$, $[(R_F)_4BF]^-$, $[B(CN)_4]^-$, $[PO_4]^{3-}$, $[HPO_4]^{2-}$, $[H_2PO_4]^-$, $[Alkyl-OPO_3]^{2-}$, $[(Alkyl-O)_2PO_2]^-$, $[Alkyl-PO_3]^{2-}$, $[R_FPO_3]^{2-}$, $[(Alkyl)_2PO_2]^-$, $[(R_F)_2PO_2]^-$, $[R_FSO_3]^-$, $[HOSO_2(CF_2)_nSO_2O]^-$, $[OSO_2(CF_2)_nSO_2O]^{2-}$, $[Alkyl-SO_3]^-$, $[HOSO_2(CH_2)_nSO_2O]^-$, $[OSO_2(CH_2)_nSO_2O]^{2-}$, $[Alkyl-OSO_3]^-$, $[Alkyl-C(O)O]^-$, $[HO(O)C(CH_2)_nC(O)O]^-$, $[R_FC(O)O]^-$, $[HO(O)C(CF_2)_nC(O)O]^-$, $[O(O)C(CF_2)_nC(O)O]^{2-}$, $[(R_FSO_2)_2N]^-$, $[(FSO_2)_2N]^-$, $[((R_F)_2P(O))_2N]^-$, $[R_FSO_2)_3C]^-$, $[(FSO_2)_3C]^-$, $Cl^-$ and/or $Br^-$ wherein:

n=1 to 8;

$R_F$ is fluorinated alkyl of formula ($C_mF_{2m-x+1}H_x$) with m=1 to 12 and x=0 to 7, wherein for m=1 and x=0 to 2, and/or fluorinated (also perfluorinated) aryl or alkyl-aryl.

The alkyl-group mentioned above can be selected from linear or hyperbranched alkyl groups with 1 to 20 C-atoms, preferably with 1 to 14 C-atoms and particularly preferably with 1 to 4 C-atoms. Preferably $R_F$ means $CF_3$, $C_2F_5$, $C_3F_7$ or $C_4F_9$.

Preferred anions are selected from $PF_6^-$, $[PF_3(C_2F_5)_3]^-$, $[PF_3(CF_3)_3]^-$, $BF_4^-$, $[BF_2(CF_3)_2]^-$, $[BF_2(C_2F_5)_2]^-$, $[BF_3(CF_3)]^-$, $[BF_3(C_2F_5)]^-$, $[B(COOCOO)_2^-(BOB)$, $CF_3SO_3^-$ (Tf$^-$), $C_4F_9SO_3$(Nf$^-$), $[(CF_3SO_2)_2N]^-$ (TFSI$^-$), $[(C_2F_5SO_2)_2N]^-$ (BETI$^-$), $[(CF_3SO_2)(C_4F_9SO_2)N]^-$, $[(CN)_2N]^-$(DCA$^-$), $[CF_3SO_2]_3C]^-$, and $[(CN)_3C]^-$.

Preferably the OLEFC comprises the ionic specie $K^+A^-$ in a concentration range between 1 wt % and 50 wt %, particularly preferably between 2 wt % and 30 wt %, and very particularly preferably between 1 wt % and 10 wt % with respect to the total mass of the emissive layer Further preferred ionic materials suitable for use in an OLEFC according to the present invention selected from compounds with the formula $(K^{n+})_a(A^{m-})_b$, wherein n, m, a, and b are integers from 1 to 3, and n×a−m×b=0 and wherein one of $K^{n+}$ or $A^{m-}$ is an organic emissive material, which can be selected from compound comprising groups of small molecule or polymeric emitters as outlined elsewhere within the present invention. Preferably, n. m a, b are 1.

One particular advantage of such composition is that no additional ionic compound is needed.

In a preferred embodiment, in the said compound in form of $(K^{n+})_a(A^{m-})_b$, one of $K^{n+}$ or $A^{m-}$ is an emissive metal complex, and particularly preferably $K^{n+}$ is an emissive metal complex, wherein the metal can be selected from transition metals, preferably those of group VIII elements, lanthanides, and actinides, particularly preferably selected from Rh, Os, Ir, Pt, Au, Sm, Eu, Gd, Tb, Dy, Re, Cu, W, Mo, Pd, Ag, Ru, and very particularly preferably selected from Ru, Os, Ir, Re. Some non-limiting examples for $K^{n+}$ are $[Ir(ppy)_2(bpy)]^+$, $[Ir(ppy)_2(dpp)]^+$, $[Ir(ppy)_2(phen)]^+$, $[Ru(bpy)_3]^{2+}$, $[Os(bpy)_2L]^{2+}$ (L=cis-1,2-bis(diphenylphosphino)ethylene).

This class of compounds is called ionic transition metal complexes (iTMCs) as reported for example by Rudmann et al., J. Am. Chem. Soc. 2002, 124, 4918-4921 and Rothe et al., Adv. Func. Mater. 2009, 19, 2038-2044.

An OLEFC according to the present invention comprising at least one ionic transition-metal complex (iTMC) is also subject of the present invention.

Preferably the OLEFC comprises the iTMC in a concentration range between 20 wt % and 95 wt %, particularly preferably between 30 wt % and 80 wt %, and very particularly preferably between 50 wt % and 75 wt % with respect to the total mass of the emissive layer.

In a further embodiment of the present invention the said OLEFC comprises a compound with the formula $(K^{n+})_a(A^{m-})_b$, wherein one of $K^{n+}$ or $A^{m-}$ is an emissive singlet emitter, and particularly preferably $K^{n+}$ an emissive singlet emitter. Such kind of compound can be selected from charged laser dyes, for examples p-quaterphenyl-4,4'''-disulfonicacid disodiumsalt (polyphenyl 1), p-quaterphenyl-4,4'''-disulfonicacid dipotassiumsalt (polyphenyl 2), 2-(4-biphenylyl)-6-phenylbenzoxazotetrasulfonicacid potassium salt (furan 2), [1,1'-biphenyl]-4-sulfonic acid, 4',4''-1,2-ethene-diylbis-, dipotassium salt (stilbene 1), 2,2'-([1,1'-biphenyl]-4,4'-diyldi-2,1-ethenediyl)-bisbenzenesulfonic acid disodium salt (stilbene 3), benzofuran,2,2'-[1,1'-biphenyl]-4,4'-diyl-bis-tetrasulfonic acid (tetrasodium salt) (furan 1), 2-(pdimethylaminostyryl)-pyridylmethyl Iodide (DASPI), 2-(pdimethylaminostyryl)-benzothiazolylethyl Iodide (DASBTI), 3,3'-diethyloxacarbocyanine Iodide (DOCI), 4,4-difluoro-1,3,5,7,8-pentamethyl-4-bora-3a,4a-diaza-s-indacene 1,3,5,7,8-pentamethylpyrromethenedifluoroborate complex (pyrromethene 546), 3,3'-dimethyl-9-ethylthiacarbocyanine Iodide (DMETCI), disodium-1,3,5,7,8-pentamethyl pyrromethene-2,6-disulfonate-difluoroborate complex (pyrromethene 556), 4,4-difluoro-2,6-diethyl-1,3,5,7,8-pentamethyl-4-bora-3a,4a-diaza-s-indacene 2,6-diethyl-1,3,5,7,8-pentamethylpyrromethenedifluoroborate complex (pyrromethene 567), o-(6-amino-3-imino-3H-xanthen-9-yl)-benzoic acid (rhodamine 110), benzoic acid, 2-[6-(ethylamino)-3-(ethylimino)-2,7-dimethyl-3H-xanthen-9-yl], perchlorate (rhodamine 19), 4,4-difluoro-2,6-di-n-butyl-1,3,5,7,8-pentamethyl-4-bora-3a,4a-diaza-s-indacene 2,6-di-n-butyl-1,3,5,7,8-pentamethylpyrromethenedifluoroborate complex (pyrromethene 580), benzoic acid, and 2-[6-(ethylamino)-3-(ethylimino)-2,7-dimethyl-3H-xanthen-9-yl]-ethyl ester, monohydrochloride (rhodamine 6G), which are commercially available at Lambda Physik AG, Goettingen, Germany.

Another subject of the present invention is a OLEFC comprising at least one compound of the formula $(K^{n+})_a(A^{m-})_b$, characterized in that one of $K^{n+}$ or $A^{m-}$ is an emissive singlet emitter.

Very preferably $K^{n+}$ is an emissive singlet emitter. $K^{n+}$ is preferably selected from the group as defined above.

Preferably the light emitting device is a electroluminescent device.

Preference is given to an OLEFC comprising 3, particularly preferably 2, and very particularly preferably 1 compound of said formula $(K^{n+})_a(A^{m-})_b$.

If desired, a luminescent material, such as a phosphor or a fluorescent dye may be added to the encapsulation material 50. The present invention also relates to an OLEFC comprising at least one phosphor material. The luminescent material emits light having a first wavelength, in response to being irradiated by visible or ultraviolet radiation having a shorter, second wavelength, emitted by the light emitting layer 30. For example, the luminescent material may emit yellow or white light in response to incident ultraviolet or blue radiation, respectively, from layer 30. The mixture of blue and yellow light appears as white light to an observer. Thus, the light emitting fiber appears to emit white light to the observer, even when layer 30 does not emit white light. The device may also emit any color of light other than white, if desired.

Examples of phosphor materials that can be utilized include those phosphors based on cerium doped into a $Y_3Al_5O_{12}$ (YAG) lattice which crystallizes in the garnet structure. Specific examples include $(Y_{1-x-y}Gd_xCe_y)_3Al_5O_{12}$ (YAG:Gd,Ce), $(Y_{1-x-y}Ce_x)_3Al_5O_{12}$ (YAG:Ce), $(Y_{1-x}Ce_x)_3(Al_{1-y}Ga_y)_5O_{12}$ (YAG:Ga,Ce) and $(Y_{1-x-y}Gd_xCe_y)_3(Al_{5-z}Ga_z)_5O_{12}$ (YAG:Gd,Ga,Ce) and $(Gd_{1-x}Ce_x)Sc_2Al_3O_{12}$ (GSAG). The YAG phosphors can be described generally as $(Y_{1-x-y}Gd_xCe_y)_3(Al_{1-z}Ga_z)_5O_{12}$, wherein x+y≤1; 0≤x≤1; 0≤y≤1; and 0≤z≤1. The position of the peak of the emission band varies considerably in the aforementioned phosphors. Depending on the garnet composition, the $Ce^{3+}$ emission can be tuned from the green (approximately 540 nm; YAG:Ga,Ce) to the red (approximately 600 nm; YAG:Gd:Ce) without appreciable loss in the luminescence efficiency. An appropriate phosphor material or blend of phosphor materials in combination with a blue or UV emission of the organic radiation emitting fiber can produce a white field.

Green-emitting phosphors that can be used according to the present invention: $Ca_8Mg(SiO_4)4Cl_2:Eu^{2+}$, $Mn^{2+}$; $GdBO_3:Ce^{3+},Tb^{3+}$; $CeMgAl_{11}O_{19}:Tb^{3+}$; $Y_2SiO_5:Ce^{3+},Tb^{3+}$; and $BaMg_2Al_{16}O:Eu^{2+},Mn^{2+}$.

Red-emitting phosphors that can be used according to the present invention: $Y_2O_3:Bi^{3+}$; $Sr_2P_2O_7:Eu^{2+},Mn^{2+}$; $SrMgP_2O_7:Eu^{2+}$, $Mn^{2+}$; $(Y,Gd)(V,B)O_4:Eu^{3+}$; and $3.5 MgO.0.5MgF_2.GeO_2: Mn^{4+}$.

Blue-emitting phosphors that can be used according to the present invention: $BaMg_2Al_{16}O_{27}:Eu^{2+}$ and $Sr_5(PO_4)_{10}Cl_2:Eu^{2+}$.

Still other ions may be incorporated into the inorganic phosphor to transfer energy from the light emitted from the organic material to other activator ions in the phosphor host lattice as a way to increase the energy utilization. For example, when $Sb^{3+}$ and $Mn^{2+}$ ions exist in the same phosphor lattice, $Sb^{3+}$ efficiently absorbs light in the blue region, which is not absorbed very efficiently by $Mn^{2+}$, and transfers the energy to $Mn^{2+}$ ion. Thus, a larger total amount of light emitted by the organic EL material is absorbed by both ions, resulting in higher quantum efficiency of the total device.

In addition, more than one phosphor material may be combined together and then utilized with an organic radiation emitting device to achieve different colors, color temperatures, and color rendition indices. Other phosphors which can be used are described in U.S. Ser. No. 09/469,702, which is hereby incorporated by reference. An example of a suitable red emitting inorganic phosphor is $SrB_4O_7:Sm^{2+}$, where the $Sm^{2+}$ following the colon represents an activator. This phosphor absorbs most visible wavelengths shorter than 600 nm and emits light as a deep red line with a wavelength greater than 650 nm. An example of a suitable green emitting inorganic phosphor is $SrGa_2S_4:Eu^{2+}$. This phosphor absorbs below 500 nm and has a maximum emission at 535 nm. An example of a suitable blue emitting inorganic phosphor is $BaMg_2Al_{16}O_{27}:Eu^{2+}$. $BaMg_2Al_{16}O_{27}:Eu^{2+}$ absorbs most wavelengths below 430 nm and has a maximum emission at 450 nm. Examples of organic dyes which can be utilized as the luminescent material include coumarin 460 (blue), coumarin 6 (green), and nile red.

Preferably the OLEFC comprises the phosphor material(s) in a concentration range between 5 wt % and 40 wt %, particularly preferably between 10 wt % and 30 wt %, and very particularly preferably between 15 wt % and 25 wt % with respect to the total mass of the encapsulation layer 50.

The OLEFC according the present invention can be typically prepared as follows:
a. Clean the fiber core The cleaning process which is typically used for glass fibers can also be used for fiber cores of OLEFCs: fiber cores are degreased with solvents and then cleaned by exposure to a UV-ozone ambient. The specific cleaning process can be adopted according to the specific fiber core used.

b. Deposition the first electrode, by conformally evaporating metal or coating from a solution or formulation comprising a conductive material. When employing the conformal evaporation, the fiber is axially rotated at a desired speed during the evaporation, for example from 30-60 rpm, to achieve uniformity. This is a preferred method when metal anodes are used.

In another preferred embodiment, the anode can be coated from an ink or solution or a formulation comprising a conductive material. Such conductive material can be metal or metal oxide nanoparticle, which can be dissolved in the solution or dispersed in the formulation, for example Ag or ITO, and organic conductive materials, for example PEDOT:PSSH. Suitable coating methods can be selected from dip coating, spin coating, ink jet printing, letter-press printing, screen printing, doctor blade coating, roller printing, reverse-roller printing, offset lithography printing, flexographic printing, web printing, spray coating, brush coating or pad printing, and slot-die coating, preferably from dip-coating or spray coating; The said formulation can be a solution, a dispersion, or an emulsion comprising one continuous phase and a discontinuous phase (nanodroplet). The electrode is heated to remove residual solvent(s).

A further suitable method for the deposition of electrode is the electrochemical deposition, for example galvanic deposition of metals, e.g. aluminium, which represents a potential low-cost method for mass production.

c. Deposition of the EML by coating a solution or formulation comprising at least one organic electroluminescent compound and at least one ionic specie. Suitable coating methods can be selected from dip coating, spin coating, ink jet printing, letter-press printing, screen printing, doctor blade coating, roller printing, reverse-roller printing, offset lithography printing, flexographic printing, web printing, spray coating, brush coating or pad printing, slot-die coating, particularly preferably by dip-coating or spray coating. The said formulation can be a solution, a dispersion, or an emulsion comprising one continuous phase and a discontinuous phase. If the ionic compound and the organic emissive compound are not soluble in a common solvent, the emulsion or dispersion is preferred. The examples of such dispersion and emulsion can be referred to WO 2003/050147, EP 09015860.1, EP 09015861.9, and EP 09015862.7.

d. Deposition the second electrode; The same method as described for the first electrode can be applied for the second electrode.

e. Optionally, encapsulation of the fiber device.

Encapsulation can be achieved by using a UV-cured resin, for example epoxy resin, or a thin film comprising for example $SiN_x$, $SiO_x$, $Al_2O_3$ etc. The OLEFCs according to the present invention can be preferably mass produced using dip-coating. One general production line is schematically shown in FIG. 13, taking, for example, an OLEFC having a structure of anode/HIM/interlayer/EML/cathode, wherein the electrodes are deposited by physical vapor deposition and the organic function layers, HIM, interlayer and EML are coated by dip-coating. The physical vapor deposition methods could be selected from such as thermal vacuum evaporation, sputtering, Cathodic Arc Deposition, Pulsed laser deposition and e-beam etc. Another particularly preferred production method is all solution based, as schematically shown in FIG. 14. The components used in both FIGS. 13 and 14 are explained as follows: 210 is a fiber core; 130 is a deposition chamber for the first electrode; 200 is a deposition chamber for the second electrode; 240 is a container comprising an ink comprising a conductive material for the first electrode; 140 is a container containing solution of buffer material or HIM; 160 is a container containing a solution or a formulation of HTM or interlayer material; 180 is a container containing a solution or a formulation of an emissive composition; 250 is a container containing an ink comprising a conductive material for the second electrode; 150, 170, 190, 220 and 230 are dryers.

The OLEFCs according to the present invention can be used to be arranged in a specific way in order to get any kind of canvas.

The parallel arrangement of light emitting fibers in a canvas is only one possibility. Any processing known for fibers can be employed to get a canvas. The fibers can, e.g. be woven as depicted in FIG. 5. Hereby different light emitting fibers can be processed in order to get a canvas emitting different wavelengths or ranges of wavelengths. The fibers emitting the same wavelength(s) can be arranged in parallel to each other so that fibers emitting different wavelength(s) are perpendicular to each other (FIG. 6). The fibers emitting different wavelength(s) can also be arranged in an alternating fashion. A canvas comprising at least one OLEFC according to the present invention is also subject of the present invention.

The OLEFCs and/or canvas according to the present invention can be used in order to set up a device. The device comprising the light emitting fibers can be stiff or flexible, wherein flexibility includes both plasticity and elasticity as defined above. By choosing the appropriate materials the degree of flexibility of the light emitting fibers can be tailored to any desired value. Stiffness can be achieved by either stiffness of the device, stiffness of the fibers or stiffness of both device and fibers. The overall device can be, at least in part, flexible even if the light emitting fibers are not. This can be accomplished, e.g., if the fibers are arranged on the device so that they run in paralell. The paralell fibers can be fixed on a flexible substrate, such as a plaster and flexibility occurs, at least in part, perpendicular to the fibers. The device comprising the fibers can therefore adopt any shape according to the physiognomy of the subject to be treated or the shape required for specific applications and it can follow the movements and changes of its shape instantaneously. In another preferred embodiment the fiber deforms plastically. If the fiber is, e.g., incorporated in a bandage or plaster, the plaster can be adopted to the physiognomy of the subject to be treated. It may or may not follow the subject's changes of the surface. Depending on the degree of plasticity and stiffness the plaster or bandage can also stabilize parts of the surface to be treated.

Flexibility in conjunction with plasticity of the said device can also be used to design panels of any desired shape that can be used, e.g., for general lighting or display applications or as display backlit or as information display such as signage.

The said OLEFC and/or canvas comprising the OLEFCs and/or devices comprising the OLEFCs and canvas can be used, e.g., in order to treat animals and/or humans. The can also be used for lighting applications as outlined within the present invention. For these purposes the device comprises an attachment means for attaching the device to a human or animal subject or to any technical substrate, e.g. for lighting applications.

The device according to the present invention can have any shape, be rigid or flexible. The device requires energy supply in any form. The energy supply may be directly associated to the device or separated by, e.g., a cable. A battery, particularly a printable battery, may be attached to the device in order to provide a device forming a totally self-contained portable unit. In the case of medical or cosmetic applications this self-contained portable unit represents a comfortable device for the subjects to be treated. Irradiation may, thus, occur at any time and at any place without disturbing the subject to be treated in its habits or daily life. Home use of devices according to the present invention is particularly preferable. The device may be self adhesive and detachable. It may conform a planar or non-planar portion of the body or be an implantable probe.

The device according to the present invention may comprise an interactive steering unit. The steering unit may allow a switch from continuous illumination to pulsed illumination. It also may allow the precise adaptation of irradiation intensities and/or wavelengths to be emitted. The steering unit may be directly associated to the device. It can also be separated via a permanent or temporary linkage. The device may be disposable and is suitable for uses in the hospital or outside the hospital.

In any case the device according to the present invention is suitable as light weight device for portable use. However, stationary devices can also be prepared. The device is sufficiently portable to enable ambulatory treatment i.e. treatment in which the subject can move around freely. It can be subsequently removed in the human subject's own time, so that treatment could take place almost everywhere. This results in a better convenience and lower costs (from avoiding either an out-patient or inpatient stay in hospital).

In the case of PDT the treatment is often associated with pain. Ambulatory devices according to the present invention can be used with lower light levels since exposure can occur for a longer period of time. This overcomes a problem of pain induced in some patients by the high irradiances from conventional sources used in hospitals. In addition lower irradiance is more effective in PDT due to reduction of the extent of photobleaching of the photopharmaceutical.

The devices may be provided with a photochemical and/or a photopharmaceutical preparation present. This may be in the form of a gel, ointment or cream. Alternatively, or as well, the device may be provided with a thin film impregnated with the photopharmaceutical. Typically, the photopharmaceutical preparation is provided as a layer in contact with the light source. Provided that the photopharmaceutical preparation is transparent or sufficiently translucent for the frequency of stimulating light, the resulting device can be readily applied without a separate step of applying the photopharmaceutical to a patient. Creams which would scatter the light may nevertheless be used if they are absorbed before the light source is switched on. A photopharmaceutical layer may be covered by a peelable release medium, such as a silicone-backed sheet. The photopharmaceutical preparation may comprise an inactive compound which is metabolised in vivo to an active compound. Delivery of the photopharmaceutical can be assisted by iontophoresis. The output of light from the device may be pulsed and an electronic control circuit or microprocessor may be provided to control this pulsing and/or other aspects of device function such as duration of exposure(s) of the area to be treated and the intensity of emitted light. Pulsed devices may be provided with a preparation of a photochemical and/or a photopharmaceutical substance which is photobleachable or which is metabolised in vivo to a photobleachable chemical species.

The output of the device may take the form of a train of pulses, preferably in which the duration of the pulses is substantially the same as the interval between successive pulses. The period of the pulse train may, for example, be in the range of 20 ms to 2000 s, depending on the photobleaching characteristics of said substance.

Preferably, the attachment means comprises an adhesive surface to enable the device to be attached to a patient.

Further preferred features correspond to the first aspect above.

Preferably, the ambulatory device is provided with a photochemical and/or a photopharmaceutical preparation present. Preferred features of the preparation and its delivery are as above. In particular, the photochemical and/or photopharmaceutical may be photobleachable or may be metabolised in vivo to a photobleachable chemical species.

The means for activating and deactivating the source may control other aspects of device function such as duration of exposure(s) of the area to be treated and the intensity of emitted light.

The control means may preferably be operable to cover the source to emit a pulse train having any one or more of the preferred features of the pulse train produced by a device.

Device according to the present invention can preferably be a flat panel, curved panel, plaster, bandage, blanket, sleeping bag, sleeve, implantable probe, nasogastric tube, chest drain, pad, stent, patch, any kind of clothes, and devices covering at least one tooth in the mouth.

The device may be used as a stent, for example a tube of 1.25 to 2.25 cm radius of say 10 to 12 cm length for use inside the oesophagus.

The device may be a blanket or sleeping bag in order to treat, e.g., jaundice of infants. Currently infants suffering from jaundice are separated from their parents and illuminated in incubators blindfold. This represents an unpleasant situation for both the infant and the parents. In addition, the infant is not able to adjust his body temperature as easily as adults can do and overheating in the incubator is a critical issue. Flexible blankets and sleeping bag provide a way to treat the infant without these problems. The infant covered by the blanket or sleeping bag can be irradiated while laying in his parents' arms and overheating of the infant's body is not as critical as compared to traditional therapies. This is due to the fact that the devices according to the present invention require less power and produce, in turn, less heat.

In psoriatic patients plaques are often found in body folds. Conventional phototherapy represents a problem which is due to the fact that light emitted by a light source does not reach the plaque in the body folds. OLEFCs and/or canvas and devices comprising them can be designed to fit into body folds in order to treat psoriasis and other diseases and/or conditions found in body folds. Ductile characteristics of the light emitting fibers and devices comprising them as outlined above can be beneficial for a device intended for the treatment in body folds.

Devices can generally spoken individually tailored in any form that is required for treatment or lighting applications.

The device itself may comprise a therapeutic agent which is released in a controlled way during the treatment.

FIG. 7 shows as exemplary embodiment of the present invention a light emitting device which is a plaster. It comprises a side for attaching 1 the plaster to the subject to be treated. It can also comprise a power supply 2 which can be, e.g., a battery and particularly a printed battery. In 2 also a steering unit may be incorporated. The plaster can also comprise a reflective material 3 which is not transparent or only partly transparent. The reflective material 3 improves the efficiency of the device. The device may, dependant on the light emitting fibers 4 emit different wavelengths $\lambda_1$ to $\lambda_n$, wherein n is preferably 3, particularly preferably 2, and very particularly preferably 1.

Another embodiment of the present invention is the use of the said device in general lighting, as display backlit, as information display such as signage.

The present invention also relates to a device according to the present invention for the treatment and/or prophylaxis and/or diagnosis of diseases and/or cosmetic conditions.

Herein any therapeutic strategy is included, ie. treatment of a subject with light can be performed with or without a combination with other treatment approaches. Treatment can, for example, be carried out with one or more wavelengths in one or more devices comprising the compounds of the present invention. Furthermore, in addition to said devices comprising the fibers (herein also referred to as fiber devices or light emitting fiber devices) and compounds according to the present invention, further light sources using different technologies can be used for the treatment, such as LEDs, planar OLECs, planar OLEDs, OLEDs having the form of a fiber, and lasers. In addition, the treatment with said compositions and devices comprising them can be combined with any known treatment strategy using drugs and cosmetics.

If phototherapy is combined with the treatment of chemical compounds such as a drugs and/or cosmetics light can be used to initiate a (photo-) chemical reaction or activation of the chemical compounds, which is called photodynamic therapy (PDT). Phototherapy according to the present invention can also be used in conjunction with chemical compounds without initiating a photochemical reaction or activation. Synergistic effects for the effectiveness and safety of the treatment of a disease can arise from sequential, parallel, and overlapping treatment with both light therapy and drugs and/or cosmetics. The drug(s) or cosmetic compound(s), e.g., can be administered first for a specific time period followed by the application of phototherapy using the OLEFCs, canvas, and/or a device according to the present invention. The time gap between both treatments may also vary, depending on the drug, its photoreactivity, individual circumstances of the subject, and the specific disease or condition. Both treatments may also overlap timely either partly or completely. The exact treatment strategy will depend on the individual circumstances and the severity of the disease or condition.

The combination therapy can have a synergistic effect and can reduce the side effects of traditional treatment strategies (e.g. the side effects of tetracyclines). This is due to the fact, that smaller doses of the drugs may be required when employing a combined approach as outlined herein.

Many diagnostic devices comprise light sources for either illumination only or as functional component for the diagnosis itself, e.g. for the determination of blood parameters such as oxygen. The present invention also relates to the use of an OLEFC, a canvas and/or a device according to the present invention for diagnostic purposes, characterized in that the said OLEFC comprises at least one ionic species and at least one organic electroluminescent compound. The use of light sources comprising the said OLEFC(s) for diagnostic purposes is also subject of the present invention. Based on the teaching of the present invention, one skilled in the art will have no problems to develop diagnostic devices for which light sources are required comprising the said OLEFCs.

Treatment is any exposure of a subject to the radiation of the fiber devices according to the present invention. The treatment may be performed by direct contact between the subject and the device or without direct contact between them. The treatment may be outside or inside the subject. Treatment outside the subject may be, for instance, treatment of the skin, wounds, eye, gingival, mucosa, tongue, hair, nail bed, and nails. Treatment inside the subject may be, for instance, treatment of blood vessels, heart, breast, lung, or any other organ of the subject. Particular devices are required for most applications inside the subject. One such example may be a stent fibers according to the present invention. The said subject may preferably be a human or an animal. The term cosmetic also includes aesthetic applications.

The wavelength of light that is emitted by the devices can be precisely tailored by the selection of the appropriate functional material. In addition, colour filter and colour converter can be used to get light of the desired wavelength. Depending on the application of the functional material and/or fiber devices comprising the functional material each therapeutic or cosmetic treatment requires a more or less defined wavelength or spectrum of wavelengths to be emitted.

The said OLEFCs, the said canvas and/or the said devices preferably emit light in the range between 200 and 1000 nm, preferably between 300 and 1000 nm, particularly preferably between 300 and 950 nm, and very particularly preferably between 400 and 900 nm.

As outlined above one of the primary effects of phototherapy is the stimulation of metabolism in the mitochondria. After phototherapy, the cells show an increased metabolism, they communicate better and they survive stressful conditions in a better way.

The said OLEFCs, the said canvas and/or the said devices can be used for cellular stimulation. Preferred wavelengths or ranges of wavelengths for cellular stimulation are in the range between 600 to 900 nm, particularly preferable between 620 and 880 nm, and very particularly preferably between 650 and 870 nm. Examples of particularly preferred wavelengths for cellular stimulation are 683.7, 667.5, 772.3, 750.7, 846, and 812.5 nm.

Any disease and/or cosmetic condition approachable by phototherapy can be treated with the said OLEFCs, the said canvas and/or the said devices.

These diseases and/or conditions include, e.g., skin diseases, and skin-related conditions including skin-ageing, and cellulite, enlarged pores, oily skin, folliculitis, precancerous solar keratosis, skin lesion, wrinkled and sun-damaged skin, crow's feet, skin ulcers (diabetic, pressure, venous stasis), acne rosacea lesions, cellulite, photomodulation of sebaceous oil glands and the surrounding tissues, reducing wrinkles, acne scars and acne bacteria, inflammation, pain, wounds, psychological and neurological related diseases and conditions, edema, Pagets disease, primary and metastatic tumors, connective tissue disease, manipulation of collagen, fibroblast, and fibroblast derived cell levels in mammalian tissue, illuminating retina, neoplastic, neovascular and hypertrophic diseases, inflammation and allergic reactions, perspiration, sweating and hyperhydrosis from eccrine (sweat) or apocrine glands, jaundice, vitiligo, ocular neovascular diseases, bulimia nervosa, herpes, seasonal affective disorders, mood, sleep disorders, skin cancer, crigler naijar, atopic dermatitis, diabetic skin ulcers, pressure ulcers, bladder infections, relief of muscular pains, pain, stiffness of joints, reduction of bacteria, gingivitis, whitening teeth, treatment of teeth and tissue in mouth, wound healing.

Cosmetic conditions are preferably selected from acne, skin rejuvenation and skin wrinkles, cellulite, and vitiligo. Many therapeutic treatments also have cosmetic component. Psoriasis, e.g., can be mild, mild-to-moderate, moderate, moderate-to-severe and severe. Any of these categories has a cosmetic component, which may be responsible for severe psychological problems of affected patients.

Preferably the present invention relates to said device for the treatment and/or prophylaxis and/or diagnosis of skin diseases and/or cosmetic skin conditions.

Skin as used herein is defined as the largest organ of the integumentary system including hair, scales, feathers and nails. The term skin also includes the tongue, mucosa and gingival.

In principle any therapeutic and cosmetic condition that is approachable by phototherapy is covered by the present invention. The distinction between the terms therapeutic and cosmetic depends, as outlined above, on individual circumstances, the severity of the condition and the assessment of the physician. As outlined in the present invention many therapeutic conditions are associated with cosmetic effects, independent of the severity of the disease.

The skin diseases and skin related conditions include, but are not limited to acneiform eruptions, autoinflammatory skin diseases or conditions, chronic blistering, conditions of the mucous membranes, conditions of the skin appendages, conditions of the subcutaneous fat, connective tissue diseases, abnormalities of dermal fibrous and elastic tissue, dermal and subcutaneous growths, dermatitis, atopic dermatitis, contact dermatitis, eczema, pustular dermatitis, seborrheic dermatitis and eczema, disturbances of pigmentation, drug eruptions, endocrine-related diseases and conditions, epidermal nevi diseases and conditions, neoplasms, cysts, erythemas, genodermatoses, infection-related diseases and conditions, bacterium-related diseases and conditions, *mycobacterium* related diseases and conditions, mycosis-related diseases and conditions, parasitic infestations, stings, and bites, virus-related diseases and conditions, lichenoid eruptions, lymphoid-related diseases and conditions, melanocytic nevi and neoplasms, monocyte- and macrophage-related diseases and conditions, mucinoses, neurocutaneous, noninfectious immunodeficiency-related diseases and conditions, nutrition-related diseases and conditions, papulosquamous hyperkeratotic related diseases and conditions, pruritic related diseases and conditions, psoriasis (mild, mild to severe, and severe), reactive neutrophilic diseases and conditions, recalcitrant palmoplantar eruptions, diseases and conditions resulting from errors in metabolism, diseases and conditions resulting from physical factors, urticaria and angioedema, vascular-related diseases and conditions, and periodontitis or other diseases and conditions of the gingival.

Skin related diseases and conditions also include skin tumors, pre-malignant tumors, malignant tumors, cell carcinomas, secondary metastasis, radiodermatitis and keratosis.

The healing of wounds can also be assigned to skin diseases and skin related conditions. Wound healing can, hereby, occur at the outer surface of the subject to be treated, at its internal parts, at the skin, eye, nail or nail bed, any surface in the subject's mouth, and at the mucosa, gingival, epithelial surface of the vascular system or other part of the subjects body.

The said OLEFCs, the said canvas and/or the said device can be used in cosmetics for skin care and skin repair, e.g. as light plaster. The wavelengths or range of wavelengths emitted by the said OLEFCs, said canvas and/or said device is in the range between 400 and 800 nm, preferably between 450 and 750 nm, particularly preferably between 500 and 700 nm, and very particularly preferably between 580 and 640 nm.

Preferably the devices according to the present invention can be used for the treatment and/or prophylaxis and/or diagnosis of skin diseases and/or cosmetic skin conditions selected from acne, psoriasis, eczema, dermatitis, atopic dermatitis, edema, vitiligo, skin desensibilization, Bowens disease, tumors, pre-malignant tumors, malignant tumors, basal cell carcinomas, squamous cell carcinomas, secondary metastases, cutaneous T-cell lymphomas, solar keratosis, arsenical keratosis, radiodermatitis, and cellulite.

Further preferred skin diseases and skin-related conditions are selected from psoriasis, polymorphous light eruption, solar urticaria, actinic reticuloid atopic eczema, vitiligo, pruritus, lichen planus, early cutaneous T-cell lymphoma, dermographism, and *pityriasis* lichenoides. Preferably theses diseases and conditions are treated with light emitted by the said devices having a wavelength or a range of wavelengths between 200 and 500 nm, particularly preferably between 250 and 400 nm, and very particularly preferably between 270 and 350 nm.

The said devices can be used for PUVA therapy. PUVA therapy is derived from the therapeutic application of psoralen (7H-furo[3,2-g]chromen-7-one) and derivatives thereof together with UV-A light. PUVA can be employed for the treatment of skin diseases characterized by hyperproliferative conditions. Psoralen is the parent compound in a family of natural products. It is structurally related to coumarines and can preferably be used for the treatment of psoriasis, eczema, vitiligo, mycosis fungoides, cuntaneous T-cell lymphoma, and other autoimmune diseases. With PUVA can also bet treated atopic eczema, lichen planus, urticaria pigmentosa, polymorphous light eruption, and alopecia areata.

Psoralen can be administered orally or topically to the skin. Preferred compounds are psoralen, 8-methoxypsoralen (8-MOP), 5-methoxypsoralen (5-MOP), and 4,5',8-trimethylpsoralen (TMP). After oral administration of 8-MOP, patients become gradually reactive to UV-A and therefore to photochemotherapeutic treatment. The patients are maximally reactive 2 to 3 hours after ingestion of the drug, and during this period the irradiation is carried out.

In the case of vitiligo khellin can be used instead of psoralen. The combined treatment with light and khellin is often called KUVA.

The said devices can also be used for photopheresis. Photophoreresis is a process by which peripheral blood is exposed in an extracorporeal flow system to photoactivate 5-MOP and represents a treatment for disorders caused by aberrant T lymphocytes. It is a therapy for advanced cutaneous T-cell lymphoma, pemphigus vulgaris and progressive systemic sclerosis (scleroderma). It can be used to treat autoimmune disorders. Further diseases that can be treated include multiple sclerosis, organ transplant rejection, rheumatoid arthritis, and AIDS.

The present invention particularly refers to said devices for the treatment of acneiform eruptions. The term acneiform eruption refers to a group of dermatoses including acne vulgaris, rosacea, folliculitis, and perioral dermatitis. Acneiform eruptions are, generally spoken, caused by changes in the pilosebaceous unit and are selected from acne *aestivalis* (Mallorca acne), acne conglobata, acne cosmetica, acne fulminans (acute febrile ulcerative acne), acne keloidalis (acne keloidalis nuchae, dermatitis papillaris capillitii, folliculitis keloidalis, folliculitis keloidis nuchae, nuchal keloid acne), acne mecánica, acne medicamentosa, acne miliaris necrotica (acne varioliformis), acne vulgaris, acne with facial edema (solid facial edema), acneiform eruptions, blepharophyma, erythrotelangiectatic rosacea (erthemaotelangiectatic rosacea), excoriated acne (acne excoriae des jeunes filles, Pickers acne), glandular rosacea, gnathophyma, gramnegative rosacea, granulomatous facial dermatitis, granulomatous perioral dermatitis, halogen acne, hidradenitis suppurativa (acne inversa, Verneuil's disease), idiopathic facial aseptic granuloma, infantile acne, lupoid rosacea (granulomatous rosacea, micropapular tuberculid, rosacea-like tuberculid of Lewandowsky), lupus miliaris disseminatus faciei, metophyma, neonatal acne (acne infantum, acne neonatorum), occupational acne, ophthalmic rosacea (ocular rosacea, ophthalmorosacea), otophyma, persistent edema of rosacea (chronic upper facial erythematous edema, Morbihan's disease, Rosaceous lymphedema), pomade acne, papulopustular rosacea, perifolliculitis capitis abscedens et suffodiens (dissecting cellulitis of the scalp, dissecting folliculitis, perifolliculitis capitis abscedens et suffodiens of Hoffman), perioral dermatitis, periorbital dermatitis (periocular dermatitis), pyoderma faciale (rosacea fulminans), rhinophyma, rosacea (acne rosacea), rosacea conglobata, rosacea fulminans, SAPHO syndrome, steroid rosacea, tropical acne.

Acne vulgaris (commonly called acne) is a common skin condition, caused by changes in pilosebaceous units, skin structures consisting of a hair follicle and its associated sebaceous gland, via androgen stimulation. It is characterized by noninflammatory follicular papules or comedones and by inflammatory papules, pustules, and nodules in its more severe forms. Acne vulgaris affects the areas of skin with the densest population of sebaceous follicles; these areas include the face, the upper part of the chest, and the back. Severe acne is inflammatory, but acne can also manifest in noninflammatory forms. Acne lesions are commonly referred to as pimples, blemishes, spots, zits, or simply acne.

Acne occurs most commonly during adolescence, affecting more than 89% of teenagers, and frequently continues into adulthood. In adolescence, acne is usually caused by an increase in male sex hormones, which people of both genders accrue during puberty. For most people, acne diminishes over time and tends to disappear—or at the very least decrease—after one reaches one's early twenties. There is, however, no way to predict how long it will take to disappear entirely, and some individuals will carry this condition well into their thirties, forties and beyond.

The face and upper neck are the most commonly affected, but the chest, back and shoulders may have acne as well. The upper arms can also have acne, but lesions found there are often keratosis pilaris. Typical acne lesions are comedones, inflammatory papules, pustules and nodules. Some of the large nodules are also called cysts and the term nodulocystic has been used to describe severe cases of inflammatory acne.

Aside from scarring, its main effects are psychological, such as reduced self-esteem and, in some cases, depression or suicide. Acne usually appears during adolescence, when people already tend to be most socially insecure. Early and aggressive treatment is therefore advocated by some to lessen the overall impact to individuals.

Light exposure can be used as treatment for acne. Used twice weekly, this has been shown to reduce the number of acne lesions by about 64% and is even more effective when applied daily. The mechanism appears to be that a porphyrin (Coproporphyrin III) produced within *P. acnes* generates free radicals when irradiated by 420 nm and shorter wavelengths of light. Particularly when applied over several days, these free radicals ultimately kill the bacteria. Since porphyrins are not otherwise present in skin, and no UV light is employed, it appears to be safe.

The treatment apparently works even better if used with a mixture of the violet/blue light and red visible light (e.g. 660 nm) resulting in a 76% reduction of lesions after three months of daily treatment for 80% of the patients; and overall clearance was similar or better than benzoyl peroxide. Unlike most of the other treatments few if any negative side effects are typically experienced, and the development of bacterial resistance to the treatment seems very unlikely. After treatment, clearance can be longer lived than is typical with topical or oral antibiotic treatments; several months is not uncommon. In addition, basic science and clinical work by dermatologists has produced evidence that intense blue/violet light (405 to 425 nm) can decrease the number of inflammatory acne lesion by 60 to 70% in four weeks of therapy, particularly when the *P. acnes* is pre-treated with delta-aminolevulinic acid (ALA), which increases the production of porphyrins.

The present invention therefore also relates to a combination devices according to the present invention and further active drugs for the treatment of diseases and/or cosmetic conditions. In particular, the present invention relates to the combined use of said devices and drugs used for the treatment of acne. The drugs can be selected from any drugs typically employed in order to treat acne, such as antibiotics (topical and/or oral), hormonal treatments, topical retinoids, topical bactericidals, sulfur. Suitable topical bactericidals are, for example, benzoyl peroxide, triclosan, and chlorhexidine gluconate. Suitable topical antibiotics are, for example, erythromycin, clindamycin, and tetracycline. Suitable oral antibiotics are, for example, erythromycin, tetracycline antibiotics (e.g. oxytetracycline, doxycycline, minocycline, or lymecycline), trimethoprim, and minocycline.

Suitable hormones are, e.g., selected from estrogen, progestogen, a combination of estrogen and progestogen, cyproterone, oestrogen, a combination of cyproterone and oestrogen, drospirenone, spironolactone, and cortisone. Suitable oral retinoids are, for example, vitamin A derivatives such as isotretinoin (e.g. Accutane, Amnesteem, Sotret, Claravis, Clarus). Suitable topical retinoids are, for example, tretinoin (e.g. Retin-A), adapalene (e.g. Differin), tazarotene (e.g. Tazorac), isotretinoin, and retinol. Further suitable drugs are, e.g. selected from anti-inflammatory drugs.

The said devices can also be used in combination with dermabrasion to treat or prevent acne. Dermabrasion is a cosmetic medicial procedure in which the surface of the skin is removed by abrasion (sanding).

Hereby any therapeutic strategy is included. The drug, e.g., can be administered first for a specific time period followed by the application of phototherapy using the said devices. The time gap between both treatments may also vary, depending on the drug, its photoreactivity, individual circumstances of the subject, and the specific disease or condition. Both treatments may also overlap timely either partly or completely. The exact treatment strategy will depend on the individual circumstances and the severity of the disease or condition.

The combination therapy can have a synergistic effect and can reduce the side effects of traditional treatment strategies (e.g. the side effects of tetracyclines). This is due to the fact, that smaller doses of the drugs may be required when following the combined approach as outlined herein.

Comedones, also called blackhead, can also be treated by phototherapy employing the said devices. A comedon is a yellow or blackish bump or plug on the skin. Actually, it is a type of acne vulgaris. Comedones are caused by excess oils that have accumulated in the sebaceous gland's duct. The substance found in these bumps mostly consists of keratin and modified sebum, which darkens as it oxidizes. Clogged hair follicles, where blackheads often occur, reflect light irregularly to produce a comedon. For this reason, the blockage might not necessarily look black when extracted from the pore, but may have a more yellow-brown colour as a result of its melanin content.

In contrast, a so called whitehead, which is also called closed comedo, is a follicle that is filled with the same material, sebum, but has a microscopic opening to the skin surface. Since the air cannot reach the follicle, the material is not oxidized, and remains white.

The said devices preferably emit light, when used for the treatment of acne, in the range between 350 and 900 nm, preferably between 380 and 850 nm, particularly preferably between 400 and 850 nm, and very particularly preferably between 400 and 800 nm.

Further particularly preferred light for the treatment of acne is blue light.

Preferred blue light has emission wavelengths for the treatment of acne are 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429 and 430 nm. For example 414 and 415 nm are particularly suitable in order to kill $P.$ $acnes$ bacteria and to help cure existing blemishes and to prevent further outbreaks.

Studies on the application of phototherapy to treat acne revealed that a combination of different wavelengths or ranges of wavelengths are particularly suitable to treat acne efficiently. Particularly preferred is therefore a combination of red light and blue light to treat acne. The said red light is preferably selected from the range between 590 to 750 nm, particularly preferably between 600 and 720 nm, and very particularly preferably between 620 and 700 nm. Two further preferred wavelengths for the treatment of acne are 633 and 660 nm. The blue light can be selected from the wavelengths as described above.

In the case of comedo the said devices preferably emit light with a wavelength of 500 nm or light in the range between 500 and 700 nm are particularly preferred.

Cellulite describes a condition that is claimed to occur in most women, where the skin of the lower limbs, abdomen, and pelvic region becomes dimpled. The causes of cellulite are poorly understood and may involve changes in metabolism and physiology such as gender specific dimorphic skin architecture, alteration of connective tissue structure, vascular changes and inflammatory processes. A couple of therapies are applied to prevent or to treat cellulite. Heat and the increase of blood flow are two common techniques. Therefore light therapy is considered to be beneficial to individuals suffering from cellulite. Said devices are suitable for the treatment and/or prophylaxis of cellulite. PDT is also suitable for the treatment and/or prophylaxis of cellulite.

The wavelength for the treatment and/or prophylaxis of cellulite that is to be emitted by the said devices is in the range between 400 and 1000 nm, preferably in the range between 400 and 900 nm, particularly preferably between 450 and 900 nm, and very particularly preferably between 500 and 850 nm.

The more general term skin ageing refers to both the formation of wrinkles and hyperpigmentation. The signs of ageing of the human skin resulting from the effects on the skin of intrinsic and extrinsic factors are defined by the appearance of wrinkles and fine lines, by the yellowing of the skin which develops a wizened appearance along with the appearance of pigmentation blemishes, by a change in the thickness of the skin, generally resulting in a thickening of the stratum corneum and of the epidermis and a thinning of the dermis, by disorganization of the elastin and collagen fibers which causes a loss of elasticity, of suppleness and of firmness, and by the appearance of telnagiectasia.

Some of these signs are more particularly associated with intrinsic or physiological ageing, that is so to say with "normal" ageing associated with age, whereas others are more specific to extrinsic ageing, that is so to say ageing caused by the environment in general; such ageing is more particularly photo-ageing due to exposure to the sun. Other factors causing ageing of the skin are atmospheric pollution, wounds, infections, traumatisms, anoxia, cigarette smoke, hormonal status, neuropeptides, electromagnetic fields, gravity, lifestyle (e.g. excessive consumption of alcohol), repetitive facial expressions, sleeping positions, and psychological stressors.

The changes in the skin which occur due to intrinsic ageing are the consequence of a genetically programmed sequence involving endogenous factors. This intrinsic ageing in particular causes slowing down of the regeneration of skin cells, which is reflected essentially in the appearance of clinical damage such as a reduction of the subcutaneous adipose tissue and the appearance of fine lines or small wrinkles, and in histopathological changes such as an increase in the number and thickness of the elastic fibers, a loss of vertical fibers from the elastic tissue membrane and the presence of large irregular fibroblasts in the cells of this elastic tissue.

In contrast, extrinsic ageing results in clinical damage such as thick wrinkles and the formation of flabby and weather-beaten skin, and in histopathological changes such as an excessive accumulation of elastic substance in the upper dermis and degeneration of the collagen fibers.

There are different biological and molecular mechanisms which are responsible for the ageing of the skin and the process is currently not fully understood. However, it was recognized that both intrinsic and extrinsic factors of ageing of the skin share common mechanisms [P. U. Giacomoni et al., Biogerontology 2004, 2, 219-229]. These factors trigger a process leading to the accumulation of damages in the skin resulting in skin ageing since the expression of cell adhesion molecules provokes recruitment and diapedesis of circulating immune cells, which digest the extracellular matrix (ECM) by secreting collagenases, myeloperoxidases and reactive oxygen species.

The activation of these lytic processes provokes random damage of these resident cells, which in turn secrete prostaglandins and leukotrienes. These signaling molecules induce the degranulation of resident mast cells which release the autacoid histamine and the cytokine TNFalpha thus activating endothelial cells lining adjacent capillaries which release P*selectin and the synthesis of cell adhesion molecules such as E-selectin and ICAM-1. This closes a self-maintained micro-inflammatory cycle, which results in the accumulation of ECM damage, i.e. skin ageing.

There is a strong cosmetic and therapeutic need for novel strategies, materials, and devices for the treatment or prophylaxis of skin ageing. Various cosmetic and therapeutic compositions (including for skin care) intended inter alia to prevent or treat ageing of the skin are known. Retinoic acid and derivatives thereof have been described as anti-ageing agents in skin care, cosmetic, or dermatological compositions, in particular in U.S. Pat. No. 4,603,146. Hydroxy acids such as lactic acid, glycolic or alternatively citric acid are also known for this same application, these acids having been described in numerous patents and publications (e.g. EP-A-413528) and introduced into numerous skin care, cosmetic, or dermatological compositions on the market. Aromatic orthohydroxy acids such as salicylic acid have also been proposed (e.g. WO 93/10756 and WO 93/10755).

All of these compounds act against ageing of the skin by desquamation, that is to say removal of the dead cells at the surface of the stratum corneum. This desquamation is also referred as to a keratolytic property. However, these compounds also have side effects, consisting of stinging and redness, which the user finds unpleasant. Thus, there remains a need for anti-ageing strategies which are at least as effective as the known compounds, but do not exhibit their drawbacks. Unlike the established strategies to treat or prevent skin ageing, intervening the micro-inflammation cascade at a very early stage is a novel concept and treating and preventing intrinsic and extrinsic skin ageing according to the present inventions represents a strategy without the drawbacks known from other strategies.

Phototherapy provides a new way to treat ageing of the skin. Thus, another subject of the invention is the use of the said devices for the treatment and/or prophylaxis of skin ageing. This means, that the present invention provides solutions, inter alia, for skin rejuvenation and to reduce or prevent the formation of wrinkles.

The wavelength for the treatment of skin ageing that is to be emitted by the said devices is in the range between 400 and 950 nm. Preferably the wavelength is in the range between 550 and 900 nm, and particularly preferably between 550 and 860 nm.

The said devices may also emit light of different wavelengths or wavelength ranges which also applies for other embodiments of the present invention.

In another preferred embodiment of the present invention the said devices are used for the treatment of skin ageing emits light in the range of 600 nm and 650 nm, particularly preferably in the range between 620 nm and 650 nm.

The said devices used for the treatment and/or prevention of skin ageing preferably comprises at least one organic electroluminescent compound which emits light in the range between 350 and 950 nm, preferably between 380 and 900 nm, and particularly preferably between 400 and 900 nm.

Further particularly preferred light for the treatment and/or prophylaxis of skin ageing is blue light. Preferred blue light has emission wavelengths for the treatment and/or prophylaxis of skin ageing are 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, and 430 nm. For example 415 nm is particularly suitable.

Further particular preferred light for the treatment and/or prophylaxis of skin ageing has a wavelength between 400 and 900 nm.

Skin rejuvenation can also be achieved with light of the wavelength of 830 nm or slightly below or above that value. Therefore, devices according to the present invention emitting light in the range between 700 nm and 1000 nm, preferably between 750 nm and 900 nm, particularly preferably between 750 nm and 860 nm, and very particularly preferably between 800 nm and 850 nm are also subject of the present invention.

Redness of the skin of a subject can be treated by devices according to the present invention. The wavelength for the treatment and/or prophylaxis of redness that is to be emitted by the said devices is in the range between 460 and 660 nm. Preferably the wavelength is in the range between 500 and 620 nm, and particularly preferably between 540 and 580 nm. One particularly preferred wavelength for this purpose is 560 nm.

Dermatitis of a subject can be treated by said devices. The wavelength for the treatment and/or prophylaxis of dermatitis that is to be emitted by the devices is in the range between 470 and 670 nm. Preferably the wavelength is in the range between 490 and 650 nm, and particularly preferably between 530 and 610 nm. Two particularly preferred wavelengths for this purpose are 550 nm and 590 nm.

Atopic eczema of a subject can be treated by devices according to the present invention. The wavelength for the treatment and/or prophylaxis of atopic eczema that is to be emitted by the said devices is in the range between 470 and 670 nm. Preferably the wavelength is in the range between 490 and 650 nm, and particularly preferably between 530 and 610 nm. One particularly preferred wavelength for this purpose is 320 nm.

Psoriasis can be treated by said devices according to the present invention. The wavelength for the treatment and/or prophylaxis of psoriasis that is to be emitted by the said devices is in the range between 240 and 600 nm. Preferably the wavelength is in the range between 290 and 500 nm, and particularly preferably between 300 and 480 nm.

Examples of particularly preferred wavelengths for the treatment of psoriasis are 310, 311, 320, 400, 410, and 420 nm.

Vitiligo can be treated by devices according to the present invention. The wavelength for the treatment and/or prophylaxis of vitiligo that is to be emitted by the said devices is in the range between 240 and 500 nm. Preferably the wavelength is in the range between 290 and 400 nm, and particularly preferably between 300 and 330 nm. One particularly preferred wavelength for this purpose is 311 nm.

Targeted phototherapy has enabled therapeutic dosing of ultraviolet light to specific dermatoses while minimizing exposure of healthy skin. Specifically, the 308 nm wavelength of light within the ultraviolet B range has been shown as particularly effective for many dermatoses, including vitiligo; psoriasis; and leukoderma such as that associated with scars, striae alba and post-$CO_2$ laser resurfacing.

The devices according to the present invention can also be used for the treatment of edema. Edema, formerly known as dropsy or hydropsy, is an abnormal accumulation of fluid beneath the skin or in one or more cavities of the body. Generally, the amount of interstitial fluid is determined by the balance of fluid homeostasis, and increased secretion of fluid into the interstitium or impaired removal of this fluid may cause edema. Five factors can contribute to the formation of edema: (1) It may be facilitated by increased hydrostatic pressure or by reduced oncotic pressure within blood vessels or (2) by increased blood vessel wall permeability as in inflammation or (4) by obstruction of fluid clearance via the lymphatic or (5) by changes in the water retaining properties of the tissues themselves. Raised hydrostatic pressure often reflects retention of water and sodium by the kidney.

The devices according to the present invention used for the treatment of edema preferably comprises at least one organic electroluminescent compound (which is a functional material) which emits light in the range between 760 and 940 nm, preferably between 780 and 920 nm, particularly preferably between 800 and 900 nm, and very particularly preferably between 820 and 880 nm.

One further particularly preferred emission wavelength for the treatment of edema is 850 nm.

The devices according to the present invention can also be used for the treatment and/or prophylaxis and/or diagnosis of infections and inflammatory, neurological, and psychological diseases and/or conditions.

Many inflammatory diseases, disorder, and conditions can be treated with phototherapy. Thus, the use of said devices for the treatment and/or prophylaxis and/or diagnosis of inflammatory disorders wherein the device comprises a least one organic light emitting device is also subject of the present invention.

Inflammatory diseases and conditions cover a wide range of indications. Many diseases or condition which are seemingly unrelated to inflammation have inflammatory components that can be treated with the functional materials according to the present invention. The skin diseases and conditions mentioned in the present invention all have inflammatory components, such as acne, psoriasis, atopic dermatitis, eczema. A non limiting selection of further inflammatory diseases and conditions that can be treated with functional materials according to the present invention are arthritis, inflammatory bowel disease, gingival inflammation, inflammation of the mucosa, inflammation of the nail bed, arteriosclerosis, and inflammation of the vascular system.

Preferred wavelengths for the treatment and/or prophylaxis of inflammation are in the range between 350 and 900 nm, particularly preferably between 380 and 900 nm, and very particularly preferably between 400 and 860 nm. Further preferred wavelengths for the treatment and/or prophylaxis of inflammation are 405, 420, and 850 nm.

The said devices can be used for the treatment and/or prophylaxis of infections. Infections can be caused by bacteria and viruses. Light has several positive effects on infections. Light has, e.g., anti-inflammatory effects through the stimulation of the tissue as outlined elsewhere within the present invention.

Phototherapy with said devices are beneficial for the use to treat wounds. Wound healing is often associated with inflammation. Therefore the same wavelengths and ranges of wavelengths as outlined for the treatment and/or prophylaxis of inflammation can be applied. Treating wounds by phototherapy also prevents the formation of scares. Particularly preferred wavelengths for the treatment and/or prophylaxis of wounds and/or scares are in the range between 600 and 950 nm and very particularly preferably between 650 and 900 nm. Further preferred wavelengths for the treatment and/or prophylaxis of wounds and scares are 660, 720, and 880 nm.

Other infections that can efficiently be treated with said devices are caused by bacteria.

Further infections that can efficiently be treated with said devices are caused by viruses. A preferred embodiment of this invention is the use of the said devices for the treatment and/or prophylaxis of viral infections particularly caused by cytomegalovirus (CMV), encephalo myocarditis virus (EMCV), poliovirus, influenca virus, parainfluenza respiratory influenza virus, respiratory syncytial virus, Japanese encephalitis virus, Dengue virus, hepatitis A virus (HAV), hepatitis B virus (HBV), hepatitis C virus (HCV), hepatitis D virus (HDV), hepatitis E virus (HEV), hepatitis F virus (HFV), hepatitis G virus (HGV) Epstein Barr Virus (EBV), human immunodeficiency virus type 1 (HIV-I), human immunodeficiency virus type 2 (HIV-2), varicella zoster virus, herpes simplex virus, in particular herpes simplex virus type 1 (HSV-I), herpes simplex virus type 2 (HSV-2), or human herpes virus 1, 2, 3, 4, 7, or 8, Kaposi's sarcoma-associated herpesvirus (KSHV), rotavirus, papilloma virus, and human papilloma virus (HPV), in particular HPV of the types: 1, 2, 3, 4, 5, 8, 9, 11, 12, 13, 14, 15, 16, 17, 18, 19-29, 31, 32, 34, 36-38, 46-50, 56, or 58.

In particular viral skin diseases and/or tumor disorders can be treated with said devices such as genital warts, benign tumors of the skin and/or mucosa caused by papilloma viruses, in particular verrucae plantares, verrucae vulgares, verrucae planae juveniles, epidermodysplasia verruciformis, Condylomata acuminate, Condylomata plana, bowenoid papulosis, papilloma on the larynx and oral mucosa, focal epithelial hyperplasia, herpes labialis, varicella and shingles.

In a particularly preferred embodiments of the present invention said devices can be used for the treatment and/or prophylaxis of warts and very particularly preferably genital warts. Pulsed light therapy might be one way to treat warts with said devices.

Said devices used for the treatment and/or prophylaxis of neurological or psychological diseases and/or conditions is also subject of the present invention.

A preferred neurological disease according to the present invention is Morbus Parkinson (MB). When light reaches a certain level of intensity, it inhibits melatonin which in turn limits the production of dopamine. Limiting the melatonin concentration leads to a better production and use of dopamine in the brain. Recent case studies of light therapy on MB patients involving bright light therapy have had positive results with marked improvement in bradykinesia and rigidity in most patients while being exposed for only ninety minutes.

Further preferred neurological and psychological diseases and/or conditions according to the present invention are mood and sleep related. Light is well known to be beneficial on the mood in many circumstances. Phototherapy can also be employed to treat depression, seasonal affective disorder (SAD), non seasonal depression, circadian rhythm sleep disorder (chronic circadian rhythm sleep disorder (CRSD), situational CRSD).

The US National Library of Medicine notes that some people experience a serious mood change when the seasons change. They may sleep too much, have little energy, and crave sweets and starchy foods. They may also feel depressed. Though symptoms can be severe, they usually clear up. The condition in the summer is often referred to as Reverse Seasonal Affective Disorder, and can also include heightened anxiety. It has been estimated that 1.5 to 9% of adults in the US experience SAD.

There are different treatments for classic (winter-based) seasonal affective disorder, including light therapy with bright lights, antidepressant medication, cognitive-behavioral therapy, ionized-air administration, and carefully timed supplementation of the hormone melatonin.

The wavelength for the treatment and/or prophylaxis of these neurological and psychological diseases and/or conditions that is to be emitted by the said devices is in the range between 350 and 600 nm. Preferably the wavelength is in the range between 400 and 550 nm, and particularly preferably between 440 and 500 nm. Two particularly preferred wavelengths for this purpose are 460 and 480 nm.

Said devices may also be used for the treatment and/or prophylaxis of pain. Pain relief by phototherapy is well known. The following conditions produce pain that can be treated successfully with phototherapy: carpal tunnel syndrome, chronic wounds, epicondylitis, headache, migraine, plantar fasciitis, tendonditis and bursitis, neck pain, back pain, muscle pain, trigeminal neuralgia, and Whiplash-associated injuries. Preferably, muscle pain is treated with said devices emitting red or infrared light.

Alopecia areata is a condition affecting humans, in which hair is lost from some or all areas of the body, usually from the scalp. Because it causes bald spots on the scalp, especially in the first stages, it is sometimes called spot baldness. In 1 to 2% of cases, the condition can spread to the entire scalp (alopecia totalis) or to the entire epidermis (alopecia universalis). Conditions resembling alopecia areata, and having a similar cause, occur also in other species.

Alopecia areata (autoimmune hair loss) can be treated with said devices.

The wavelength for the treatment and/or prophylaxis of alopecia areata that is to be emitted by the said devices is in the range between 240 and 500 nm. Preferably the wavelength is in the range between 290 and 400 nm, and particularly preferably between 300 and 330 nm. One particularly preferred wavelength for this purpose is 311 nm.

As already mentioned within the present application the devices according to the present invention and/or the said OLEFCs and canvas can be employed, inter alia, for the treatment of animals and humans. However, phototherapy or light therapy can be used in order to treat any other material or organism. Further subjects and objects suitable to be treated by the irradiation with said devices are, e.g., plants, microbes, bacteria, fungi, and any kind of liquids and solids. Microbes include, but are not limited to, prokaryotes such as bacteria and archaea and eukaryotes such as protists, animals, fungi and plants. Preferred liquids are soft drinks, beverages and particularly preferably water and drinking water. Further preferred objects to be treated are foodstuff and nutrition.

The use of light as disinfectant is well known. The said devices can be used for disinfection. Hereby any kind of disinfection is meant and includes without limitation the disinfection of wounds, nutrition, and solid and liquids objects, such cosmetic, medical devices, devices used for surgery and beverages.

Preference is given to the use of said devices for the disinfection of soft drinks, beverages, preferably water, and particularly preferably drinking water. Contaminated water causes many infections worldwide and leads often to severe diseases or death of the individuals. The said devices provide a simple means to disinfect water. Water filter systems of commercial providers take advantage of ion exchange technology. The filter, however, often tend to microbial contamination, which, in turn results in water which is contaminated with microbes. One solution is to add silver salt which is from a toxicological point of view problematic. The said devices comprising them provide a solution to this problem. They can be incorporated into the water filter system in order to provide a safe, efficient, and low cost way to provide water with a low degree of microbial contamination. The light source can irradiate both the water before or after filtering or the filter cartridge itself. Preferably the said device irradiates both the filter cartridge and the already filtered water.

The procedure of disinfection of water as outlined above can basically be applied to any other liquid, particularly for soft drinks and beverages analogously.

Therefore, the said functional materials and light emitting fiber devices comprising them can be used for the disinfection of beverages and nutrition for humans and animals.

Wavelengths for disinfection according to the present invention are in the range between 200 nm and 600 nm, preferably between 250 nm and 500 nm, and very particularly preferably between 280 nm and 450 nm.

The present invention also relates to devices according to the present invention for the disinfection of water, drinking water, soft drinks, beverages, foodstuff, and nutrition.

The device according to the present invention can also be used for the use in photodynamic therapy (PDT).

Wavelengths required for PDT according to the present invention are in the range between 300 and 700 nm, preferably between 400 and 700 nm, and very particularly preferably between 500 and 700 nm. Four further preferred wavelengths are 595, 600, 630, and 660 nm.

Any therapy known as PDT can be carried out using the said devices. The property of dyes with a polycyclic hydrocarbon type chemical structure to accumulate in greater amounts in tumor tissues than in normal tissues is well known. The dyes include acridines, xanthenes, psoralens, and porphyrins. The latter dyes, in particular, hematoporphyrin (Hp) and some of its chemical derivatives (e.g. Hp D, wherein Hp D is a mixture of Hp derivatives), have superior tumor-localizing properties, which are the basis of phototherapeutic treatment of tumors with red light irradiation at predetermined times after systemic administration of the drug.

Drug used for PDT are preferably selected from aminolevulinic acid/methyl aminolevulinate, efaproxiral porphyrin derivatives (porfimer sodium, talaporfin, temoporfin, verteporfin).

The devices according to the present invention can also be used for the treatment and/or prophylaxis of jaundice and crigler naijar.

Jaundice, which is also known as icterus, is a yellowish discoloration of the skin, the conjunctival membranes over the sclerae (whites of the eyes), and other mucous membranes. The discoloration is caused by hyperbilirubinemia (increased levels of bilirubin in the blood). This hyperbilirubinemia subsequently causes increased levels of bilirubin in the extracellular fluids. Jaundice is classified in three groups, pre-hepatic (hemolytic) jaundice, hepatic (hepatocellular) jaundice, and post-hepatic (obstructive) jaundice.

Pre-hepatic jaundice is caused by anything which causes an increased rate of hemolysis, i.e. breakdown of red blood cells. In tropical countries, malaria can cause jaundice in this manner. Certain genetic diseases, such as sickle cell anemia, spherocytosis and glucose 6-phosphate dehydrogenase deficiency can lead to increased red cell lysis and therefore hemolytic jaundice. Commonly, diseases of the kidney, such as hemolytic uremic syndrome, can also lead to coloration. Defects in bilirubin metabolism also present as jaundice. Jaundice usually comes with high fevers. Rat fever (leptospirosis) can also cause jaundice.

Hepatic jaundice causes include acute hepatitis, hepatotoxicity and alcoholic liver disease, whereby cell necrosis reduces the liver's ability to metabolise and excrete bilirubin leading to a buildup in the blood. Less common causes include primary biliary cirrhosis, Gilbert's syndrome (a genetic disorder of bilirubin metabolism which can result in mild jaundice, which is found in about 5% of the population), Crigler-Najjar syndrome, metastatic carcinoma and Niemann-Pick disease, type C. Jaundice seen in the newborn, known as neonatal jaundice, is common, occurring in almost every newborn as hepatic machinery for the conjugation and excretion of bilirubin does not fully mature until approximately two weeks of age.

Post-hepatic jaundice, also called obstructive jaundice, is caused by an interruption to the drainage of bile in the biliary system. The most common causes are gallstones in the common bile duct, and pancreatic cancer in the head of the pancreas. Also, a group of parasites known as "liver flukes" can live in the common bile duct, causing obstructive jaundice. Other causes include strictures of the common bile duct, biliary atresia, ductal carcinoma, pancreatitis and pancreatic pseudocysts. A rare cause of obstructive jaundice is Mirizzi's syndrome.

Jaundice, in particular neonatal jaundice, can lead to severe medical consequences if not or not appropriately treated. Increased concentrations of bilirubin can result in a brain-damaging condition known as kernicterus, leading to significant lifelong disability; there are concerns that this condition has been rising in recent years due to inadequate detection and treatment of neonatal hyperbilirubinemia. Early treatment often consists of exposing the infant to intensive phototherapy in an more or less isolated incubator. The therapy often represents an emotionally or psychologically difficult situation for both the infant and the parents. The said devices can be employed in order to provide flexible and ambulatory devices such as blankets in order to treat any kind of the aforementioned types of jaundice. Thus, the infant can be treated while laying in its parents' arms. Traditional therapies also easily lead to overheating of the infant, which can also be significantly reduced with the treatment approach according to the present invention.

Preferably the present invention relates to the use of said light emitting devices for the treatment of neonatal jaundice.

The wavelength for the treatment and/or prophylaxis of jaundice is in the range between 300 and 700 nm. Preferably the wavelength is in the range between 350 and 600 nm, and particularly preferably between 370 and 580 nm. Further preferred wavelengths are in the range between 400 and 550 nm. Particularly preferred wavelengths are in the range between 410 and 470 nm. Two particular preferred wavelengths for this purpose are 450 and 466 nm.

In analogy to the use of said devices as mentioned above, the OLEFCs and or canvas according to the present invention can be used for the treatment and/or prophylaxis and/or diagnosis of diseases and cosmetic conditions. The present invention also relates to an OLEFC for the preparation of a device for the treatment and/or prophylaxis and/or diagnosis of diseases and/or cosmetic conditions. Further the present invention also relates to a canvas for the preparation of a device for the treatment and/or prophylaxis and/or diagnosis of diseases and/or cosmetic conditions. Hereby, the diseases and cosmetic conditions are the same as mentioned above.

In a further embodiment the present invention relates to the use of an OLEFC for the treatment and/or prophylaxis and/or diagnosis of diseases and cosmetic conditions. In yet another embodiment the present invention relates to the use of an canvas for the treatment and/or prophylaxis and/or diagnosis of diseases and cosmetic conditions. Hereby, the diseases and cosmetic conditions are the same as mentioned above.

In a further embodiment the present invention relates to the use of an OLEFC according to the present invention for the treatment and/or prophylaxis and/or diagnosis of diseases. In yet another embodiment the present invention relates to the use of the said OLEFC for the treatment and/or prophylaxis and/or diagnosis of cosmetic conditions.

In a further embodiment the present invention relates to the use of an canvas according to the present invention for the treatment and/or prophylaxis and/or diagnosis of diseases. In yet another embodiment the present invention relates to the use of the said canvas for the treatment and/or prophylaxis and/or diagnosis of cosmetic conditions.

Hereby, the diseases and cosmetic conditions are the same as mentioned above.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

It will be appreciated that many of the features described above, particularly of the preferred embodiments, are inventive in their own right and not just as part of an embodiment of the present invention. Independent protection may be sought for these features in addition to or alternative to any invention presently claimed.

The teaching as disclosed here can be abstracted and combined with other examples disclosed.

Other features of the invention will become apparent in the course of the following description of exemplary embodiments and drawings, which are given for illustration of the invention and are not intended to be limiting thereof.

WORKING EXAMPLES

Example 1

Materials

The following polymers are synthesized by employing the Suzuki coupling. The reaction can be carried out according to synthetic methods well known to the person skilled in the art. The method is described, for example, in WO 2003/048225.

Polymer PB1, a blue emitting polymer, is a copolymer comprising the following monomers with mol % as indicated:

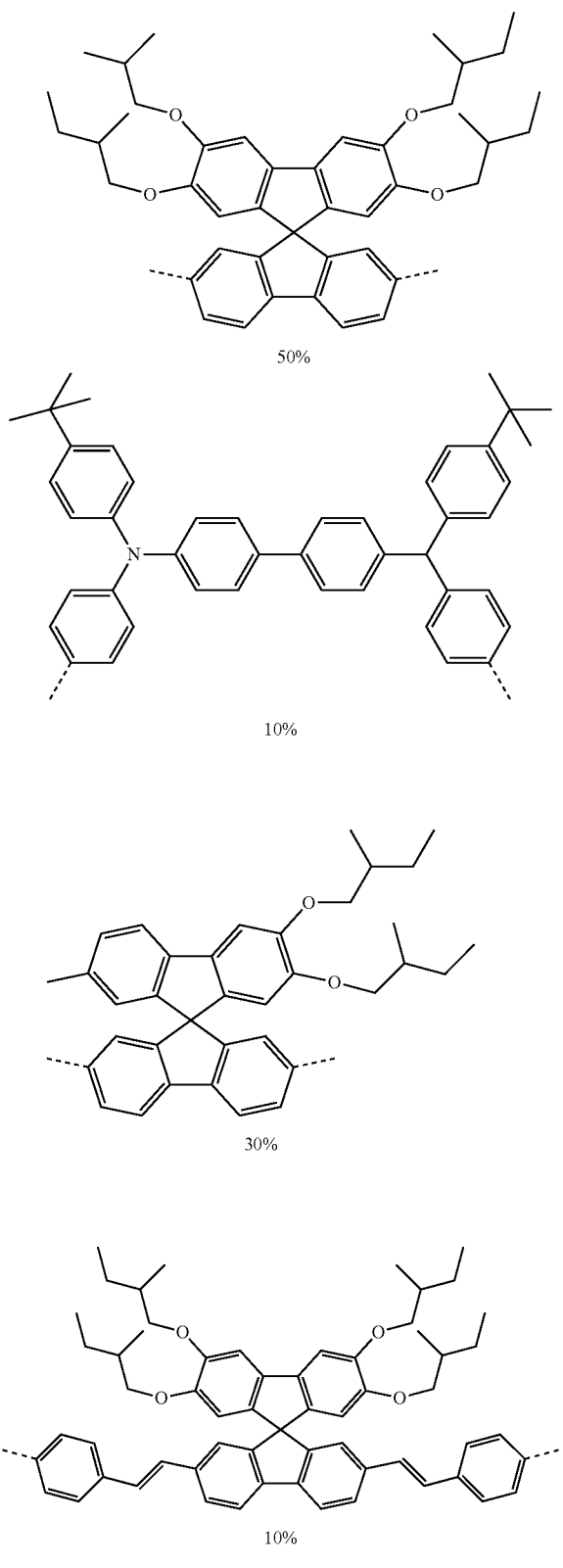

The molecular weight (MW) of the PB1 is distributed between 200000 and 300000 g/mol.

Polymer PR1, a red emitting polymer, is a copolymer comprising the following monomers with mol % as indicated by the indices of the repeating units:

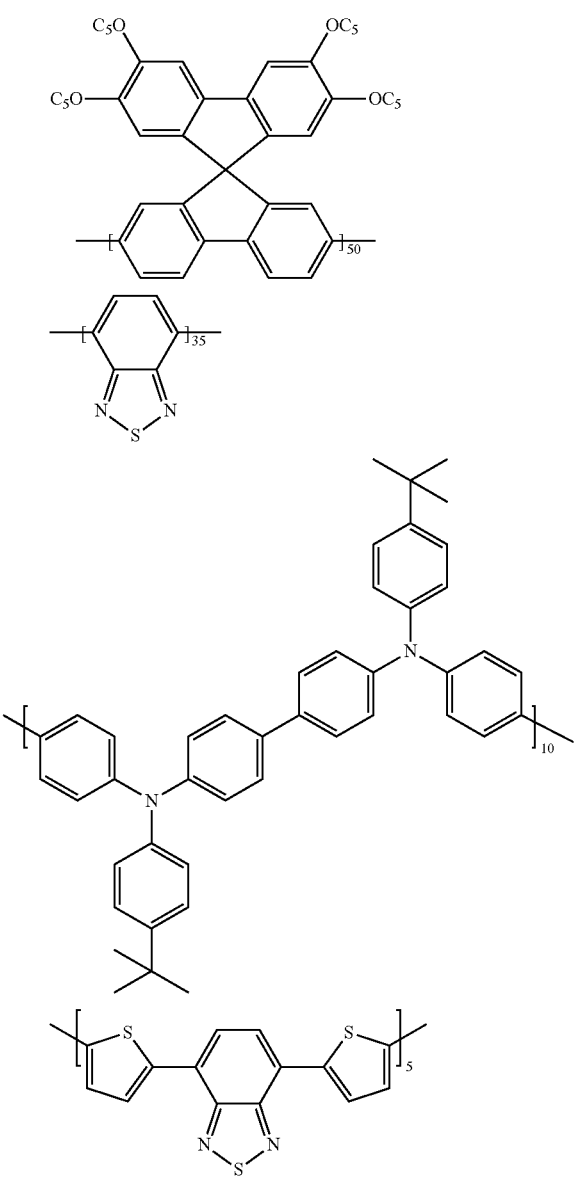

The molecular weight (MW) of the PR1 is distributed between 120000 and 720000 g/mol.

Polymer P3, used as interlayer, is a copolymer comprising the following repeating units:

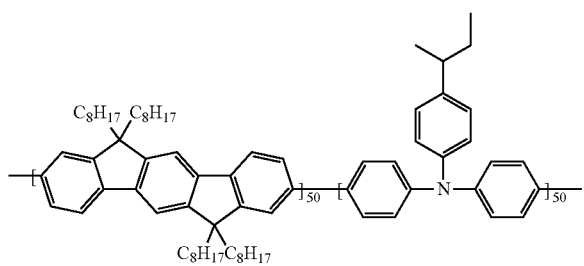

The molecular weight (MW) of the resulting polymer P3 is distributed between 200000 to 300000 g/mol.

All polymers, PB1, PR1 and P3 are well soluble in toluene.
Additionally, a soluble phenyl-substituted poly(para-phenylene vinylene) (PPV) (Super Yellow by Merck KGaA) (hereafter referred to as SY) is used as yellow emitter.

Poly(ethylene oxide) (PEO, MW=5106, Aldrich) is used as ion conductor; and Lithium trifluoromethane sulfonate (LiTf, 99.995% metal basis; Aldrich) as ion source.

Example 2

Preparation of an OLEFC

The fiber core 10 used in the present invention is a hard polymer-clad silica optical fiber (by CeramOptec Industries, Inc.), which has a silica core of 400 µm in diameter and 25 µm polyimide as jacket. Prior to the deposition of electrode, the fibers are cleaned successively by rubbing with a detergent, rinsing in deionized water, and cleaning by sonication in trichloroethylene, acetone and then isopropyl alcohol.

Figure 1:
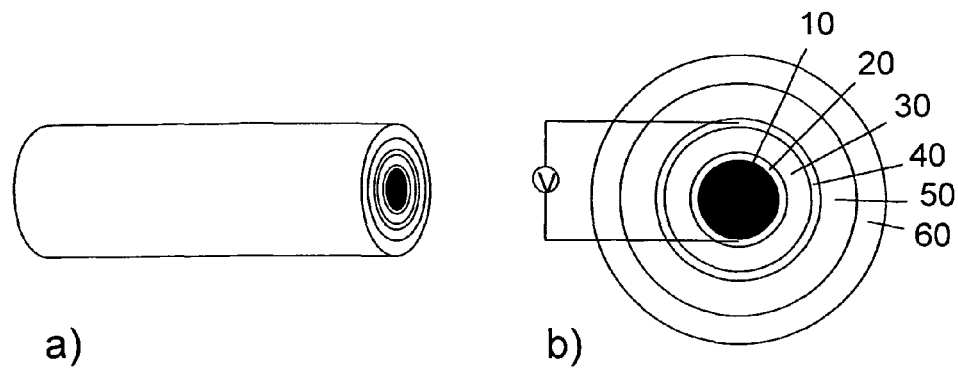
FIG. 1: Fiber with a fiber core 10 having an outer first electrode 20, a light emitting layer 30, a radiation transmissive second electrode 40 positioned over the organic light emitting layer 30. Eventually the OLEFC may also comprise an optional radiation transmissive moisture and/or air barrier layer 50 and/or an optional radiation transmissive encapsulating material 60.
Figure 2:
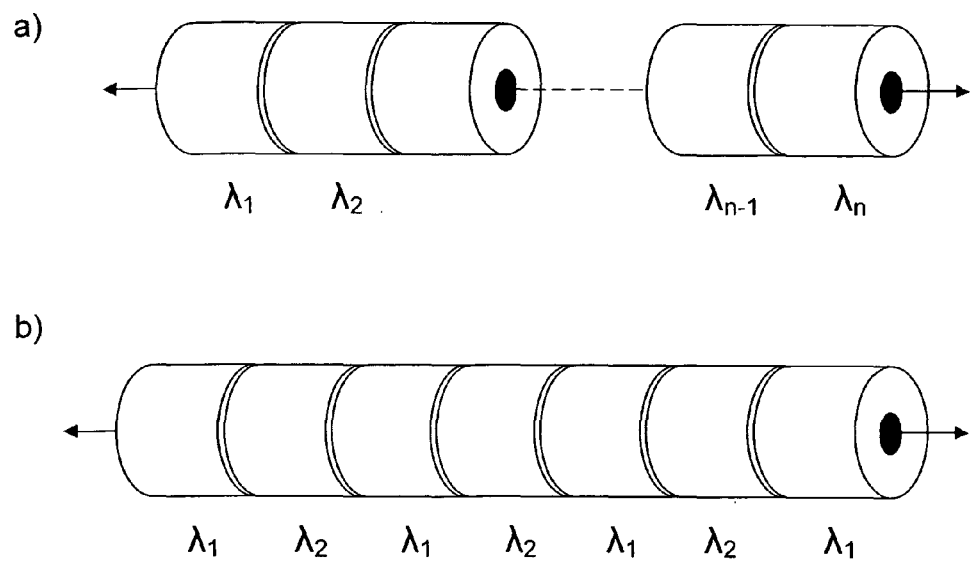
FIG. 2: Fiber divided into segments emitting n different wavelengths $\lambda_i$ (i=1 to n) or ranges of wavelengths (a). Preferably n=2 (b).
Figure 3:
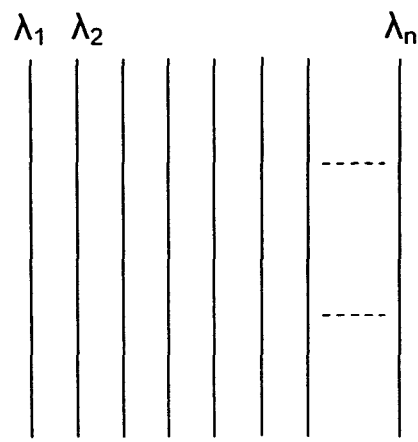
FIG. 3: Parallel arrangement of light emitting fibers in a device which emits light with n different wavelengths or ranges of wavelengths.
Figure 4:
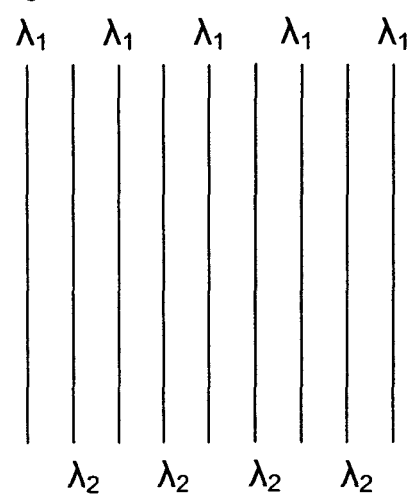
FIG. 4: Parallel arrangement of light emitting fibers in a device which emits light with two different wavelengths or ranges of wavelengths.
Figure 5:
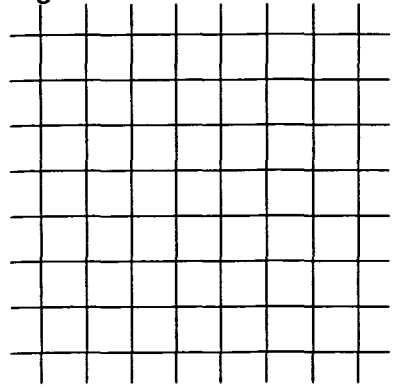
FIG. 5: Woven fibers.
Figure 6:
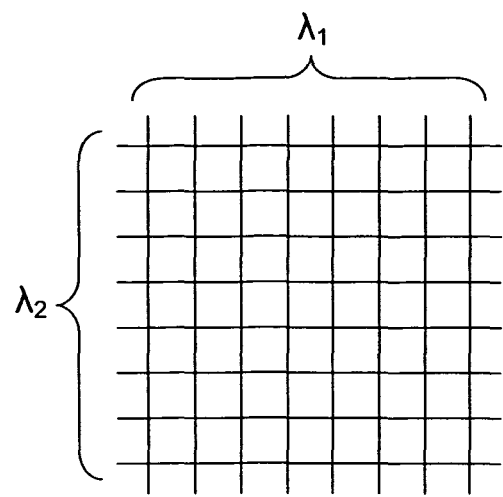
FIG. 6: Woven fibers emitting two different wavelengths or ranges of wavelengths.
Figure 7:
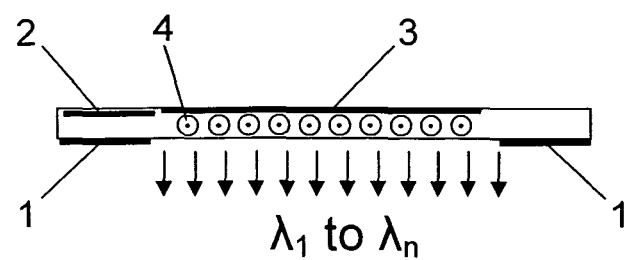
FIG. 7: Plaster with attachment side 1, power supply 2, reflective material 3, and light emitting fibers 4.
Figure 8:
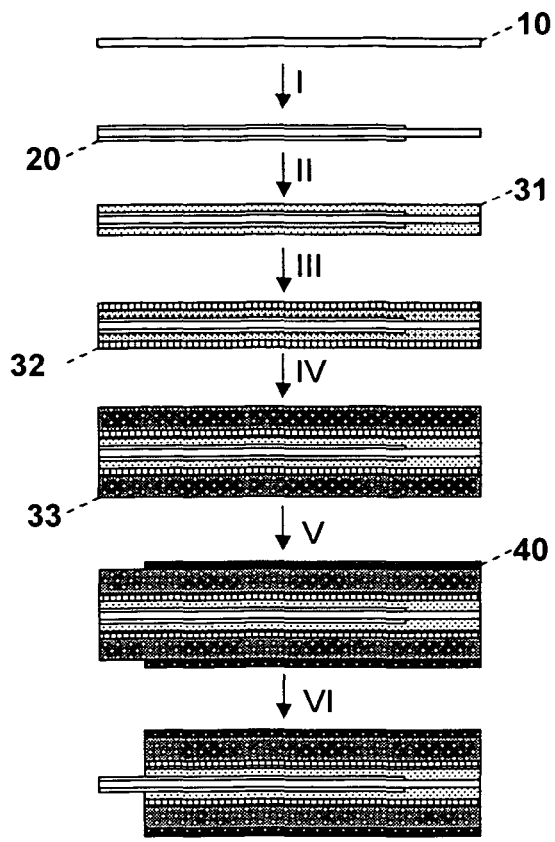
FIG. 8: One way to prepare a fiber comprising the following steps. Step I: deposition of anode 20 on fiber core 10; step II: deposition of buffer layer 31; step III: deposition of interlayer 32; step IV: deposition of emissive layer 33; step V: deposition of cathode 40; step VI: free anode

The fabrication steps I to VI are schematically depicted in FIG. 8.

Step I: Anode Deposition

The anode 20 is deposited conformally through a shadow mask using vacuum thermal evaporation at $10^{-7}$ Torr. The fibers are axially rotated at a speed of 60 rpm during the evaporation. Then, 150 nm Al is evaporated on the cleaned fiber core 10 as first electrode (anode).

Step II: Buffer Layer 31 Deposition

PEDOT (Baytron P AI 4083) is deposited as buffer layer or hole injection layer (HIL) with a thickness of 80 nm onto the fiber by dip-coating and then heated for 10 min. at 180° C.; the thickness can be controlled through the concentration and the pulling speed during the dip-coating. The fiber is then heated for 10 min. at 180° C. to remove residual water.

Step III: Interlayer 32 Deposition

The interlayer 32 is then coated by dip-coating from a toluene solution comprising interlayer polymer P3 with a concentration of 0.1 to 0.5 wt % yielding a layer with a thickness of about 40 nm;

The thickness of the film on the fiber is determined as follows. A flat glass substrate is coated by dip-coating in the same solution; the thickness of the film on glass substrate was then measured by Surface Profiler (Dektak³ ST). The concentration of the solution and pulling speeding are adjusted until the desired thickness is obtained. The same condition, concentration and pulling speed will be applied to coat P3 on the fiber.

The interlayer 32 is heated at 180° C. for 60 minutes to remove residual solvent, and to immobilize the polymer;

For OLEFCs without interlayer, step III is skipped.

Step IV: Emissive Layer 33 Deposition

The emissive layer (EML) 33 is then coated by dip-coating a chlorobenzene solution comprising emissive polymer (EM) and PEO and LiTf in a mass ratio of EM:PEO:LiTf=1:1:0.25 yielding a layer with a thickness of about 500 nm; The concentration of the compositions are listed in Table 1.

TABLE 1

| | Interlayer | EM | Solvent | Concentration [mg/ml] |
|---|---|---|---|---|
| OLEFC 1 | No | PB1 | Chlorbenzol | 27 |
| OLEFC 2 | No | PR1 | Chlorbenzol | 22.5 |
| OLEFC 3 | No | SY | Chlorbenzol | 22.5 |
| OLEFC 4 | Yes | PB1 | Chlorbenzol | 27 |
| OLEFC 5 | Yes | PR2 | Chlorbenzol | 22.5 |
| OLEFC 5 | Yes | SY | Chlorbenzol | 22.5 |

The thickness of the film on the fiber is determined as follows. A flat glass substrate was coated by dip-coating in the same solution; the thickness of the film on glass substrate was then measured by Surface Profiler (Dektak³ ST). The concentration of the solution and pulling speeding are adjusted until the desired thickness is obtained. The same condition, concentration and pulling speed will be applied to coat the corresponding film on the fiber.

The device is heated at 180° C. for 10 minutes to remove the residual solvent;

Step V: Cathode 40 Deposition

A cathode 40 consisting of Ag is conformally deposited through a shadow mask by thermal vacuum evaporation onto the emissive layer with a thickness of 25 nm; both anode and cathode along the fiber have a length of 4 cm in one segment. They displace with each other so that both electrodes overlap for ca 3 cm in length, which also corresponds to the emissive area on the fiber.

Step VI: Free Anode

The fiber is cut into segments of 5 cm in length. One end of the cut fiber, where no cathode is deposited, is washed away at first with toluene and then with ethanol to remove the polymer and PEDOT in order to get a free anode which can be contacted.

Figure 9:
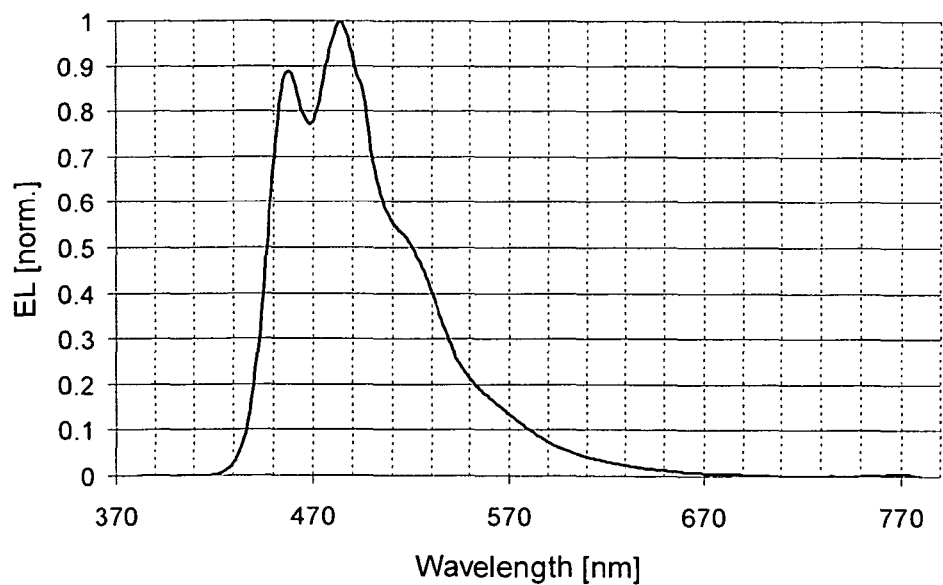
FIG. 9: Electroluminescence (EL) spectrum of OLEFC1 using PB1 as EML.
Figure 10:
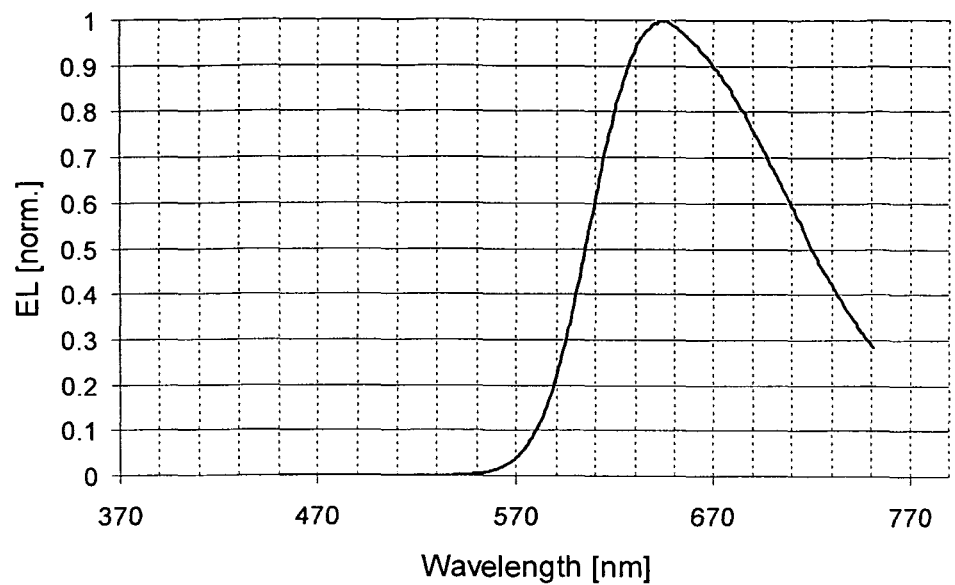
FIG. 10: EL spectrum of OLEFC2 using PR1.
Figure 11:
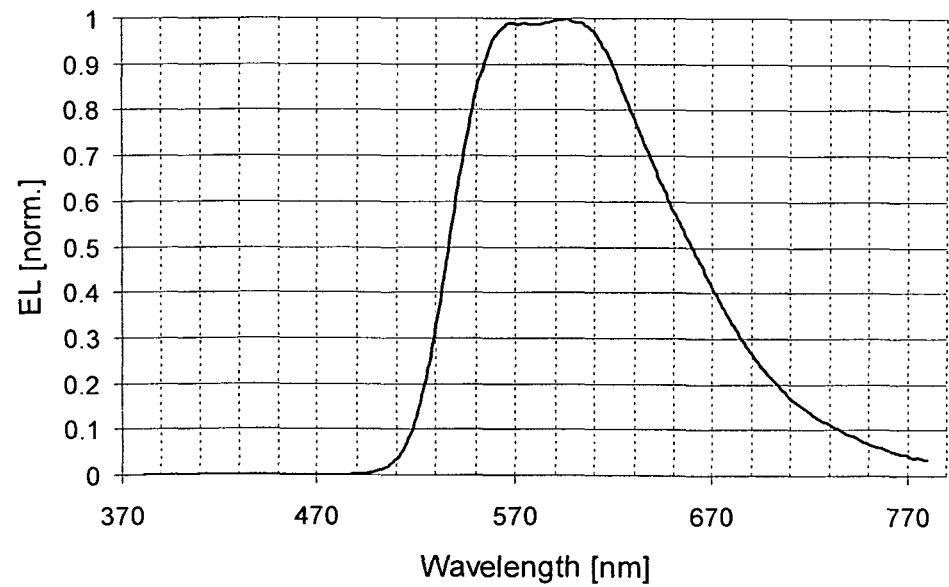
FIG. 11: EL spectrum of OLEFC3 using SY.

Prior to the preparation of plasters, the OLEFCs are tested in a glovebox. An EL spectrum is recorded by Ocean Optics USB2000 spectrometer. The EL spetrum of OLEFC1 using PB1 as EML is shown in FIG. 9, and that of fiber OLEFC2 using PR1 in FIG. 10, and that of OLEFC3 using SY in FIG. 11. The fibers are selected for the preparation of a plaster with respect to homogeneity of emission and brightness by optical observation.

Example 3

Preparation of Plasters Comprising OLEFCs

The transparent flexible poly(ethylene naphthalate) (PEN) foil is used as substrate for the preparation of plasters.

Figure 12:
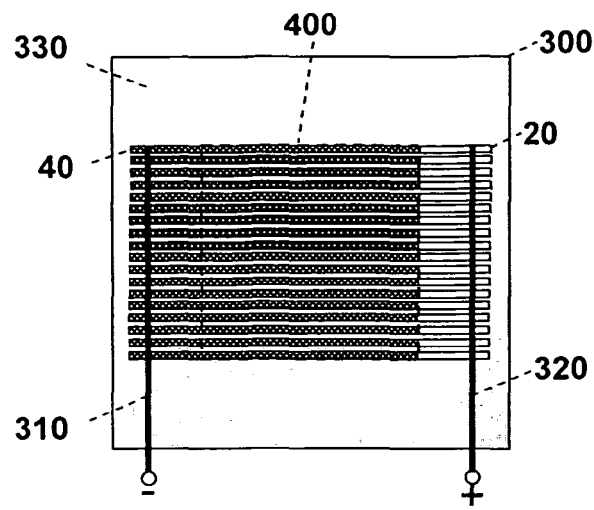
FIG. 12: Schema of a plaster according to present invention with PEN substrate 300, OLEC fibers 400, cathode 40, anode 20, thin conducting wires 310 and 320, and epoxy resin encapsulation 330.
Figure 13:
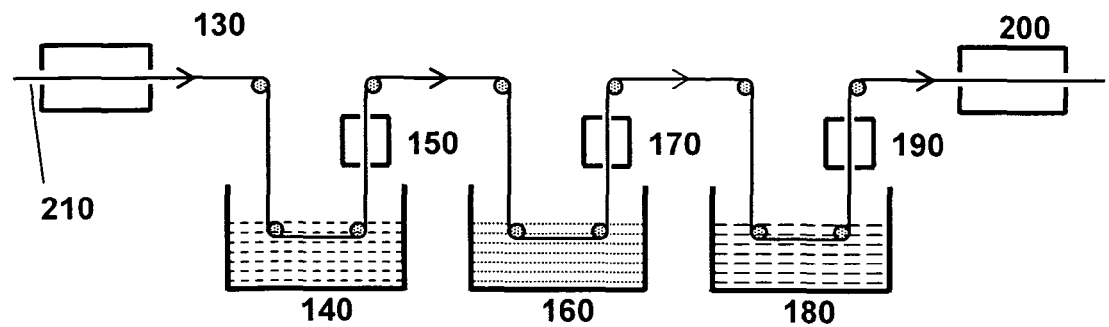
FIG. 13: Fiber production line by employing dip coating. 210—fiber core; 130—deposition chamber for the first electrode; 200—deposition chamber for the second electrode; 140—container containing solution of buffer material or HIM; 160—container containing a solution or a formulation of HTM or interlayer material; 180—container containing a solution or a formulation of an emissive composition; 150, 170, and 190 are dryers.
Figure 14:
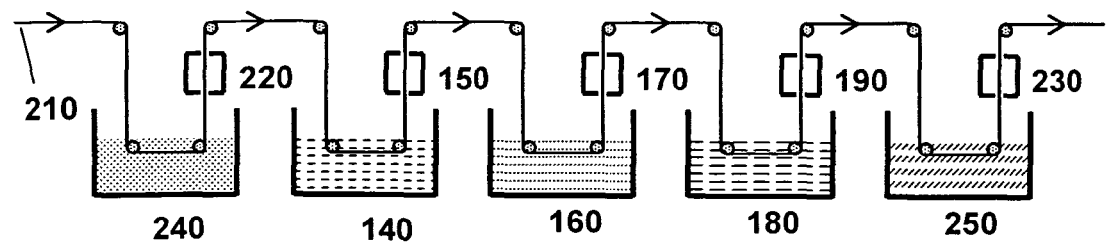
FIG. 14: Production method which is all solution based. 250—container containing an ink comprising a conductive material for the second electrode; 220 and 230 are dryers; 240—container comprising an ink comprising a conductive material for the first electrode.

A plaster according to present invention is schematically shown in FIG. 12. The PEN substrate 300 has an area of ca. 5.5 cm×5.5 cm. The fiber OLECs 400 prepared in Example 2 are arranged in parallel in the middle of the substrate, with cathode 40 on one side and free anode 20 on the other side.

Then thin conducting wires 310 and 320 are connected to both the ends of the cathodes ends and the ends of the anodes of the OLEFCs with the help of silver conductive glue. The emissive area is defined in the middle area of the substrate, as marked by a dashed line in FIG. 12.

The device is then fixed and encapsulated by using UV-cured epoxy resin. UV Resin T-470C2, an advanced UV adhesives for OLED made by Nagase & Co., LTD, is applied to the area as marked as 330 in FIG. 12 being thick enough to cover all fibers on the substrate. The device is then exposed to an UV lamp with a dose of about 6 J/cm² to cure the resin. The cured resin colors slightly yellow. Other transparent resin may be good to get more light out. A reflection foil can then be put on the plaster to further enhance light output of the plaster.

In this manner, the plasters comprising OLEFCs 1 to 6 are prepared, and lifetime is tested under constant current with an initial luminescence of about 200 Cd/m² by optical observation. After two days, the difference between OLEFC1 to 3 and OLEFC 3 to 6 is noticeable. The OLEFCs with interlayer, OLEFC 3 to 6, show longer lifetimes as compared to those without interlayer with respect to dark spots, brightness decay and homogeneity.

Another set of plasters comprising OLEFC3 and OLEFC4, which are positioned alternatively on the PEN substrate, are prepared. Such plasters are suitable for the treatment of, e.g., acne vulgaris.

The invention claimed is:

1. An organic electroluminescent device, wherein the device is an organic light emitting electrochemical cell (OLEC) comprising at least one ionic specie of formula $(K^{n+})_a (A^{m-})_b$, wherein $K^+$ is a cation, $A^-$ is an anion, and either $K^+$ or $A^-$ is an organic emissive material, where n, m, a and b are independently selected from the integers 1, 2 or 3, and $n*a-m*b=0$, and the OLEC has the form of a fiber (OLEFC).

2. The electroluminescent device according to claim 1, wherein the OLEFC comprises a fiber core which is flexible or rigid.

3. The electroluminescent device according to claim 1, wherein the OLEFC comprises:
   a) a fiber core having an outer electrode;
   b) a light emitting layer (EML) comprising at least one organic electroluminescent compound and at least one ionic specie, positioned over an outer surface of the outer electrode; and
   c) a radiation transmissive electrode positioned over the light emitting layer.

4. The electroluminescent device according to claim 1, wherein the form of the fiber has a circular, oval, or polygonal cross section or a combination thereof.

5. The electroluminescent device according to claim 1, wherein the OLEC further comprises at least one organic electroluminescent compound selected from the group consisting of a fluorescent emitter material, a phosphorescent emitter material, and an emissive organo metallic complex.

6. The electroluminescent device according to claim 1, wherein the OLEC further comprises at least one host material and at least one emitter material in a light emitting layer (EML), wherein the host material is selected from the group consisting of an anthracene, a benzanthracene, a ketone, a carbazole, a triarylamine, an indenofluorene, a fluorene, a spirobifluorene, a phenanthrene, a dihydrophenanthrene, a thiophene, a triazine, an imidazole, an isomer and a derivative thereof.

7. The electroluminescent device according to claim 1, wherein the OLEFC further comprises at least one functional material selected from the group consisting of a hole transport material (HTM), a hole injection material (HIM), an electron transport material (ETM), and electron injection material (EIM).

8. The electroluminescent device according to claim 1, wherein the OLEFC comprises at least one ionic transition-metal complex (iTMC).

9. A canvas comprising at least one OLEFC according to claim 1.

10. An article comprising at least one OLEFC according to claim 1.

11. An article comprising at least one canvas according to claim 9.

12. The article according to claim 10 is selected from a flat panel, curved panel, plaster, bandage, blanket, sleeping bag, sleeve, implantable probe, nasogastric tube, chest drain, pad, stent, patch, any kind of clothes, or a device covering at least one tooth in the mouth.

13. The article according to claim 10 as a light source for use in general lighting, as display backlit, or information display.

14. The device according to claim 1 for the treatment and/or prophylaxis and/or diagnosis of diseases and/or cosmetic conditions.

15. The device according to claim 1 for the treatment and/or prophylaxis and/or diagnosis of skin diseases and/or cosmetic skin conditions.

16. The device according to claim 15, wherein the skin diseases and/or cosmetic skin conditions selected from acne, psoriasis, eczema, dermatitis, atopic dermatitis, edema, vitiligo, skin desensibilization, Bowens disease, tumors, pre-malignant tumors, malignant tumors, basal cell carcinomas, squamous cell carcinomas, secondary metastases, cutaneous T-cell lymphomas, solar keratosis, arsenical keratosis, radiodermatitis, or cellulite.

17. The device according to claim 1 for the treatment and/or prophylaxis and/or diagnosis of infections and inflammatory, neurological, and psychological diseases and/or conditions.

18. The device according to claim 1 for the disinfection of water, drinking water, soft drinks, beverages, foodstuff, and nutrition.

19. The device according to claim 1 for use in photodynamic therapy (PDT) and/or for the treatment and/or prophylaxis of jaundice and crigler naijar.

20. The device according to claim 1, wherein one of $K^{n+}$ or $A^{m-}$ is an organic emissive material, and each of n, m, a, and b is 1.

21. A method for the preparation of an organic light emitting electrochemical fiber cell (OLEFC) comprising:
 a) cleaning of a fiber core;
 b) deposition of an outer electrode by conformal evaporation of a metal, or as a coating from a solution or formulation that includes a conductive material;
 c) deposition of a light emitting layer (EML) as a coating from a solution or formulation that includes at least one organic electroluminescent compound and at least one ionic species of formula $(K^{n+})_a(A^{m-})_b$, wherein $K^+$ is a cation, $A^-$ is an anion, and either $K^+$ or $A^-$ is an organic emissive material, where n, m, a and b are independently selected from the integers 1, 2 or 3, and $n*a-m*b=0$;
 d) deposition of a radiation transmissive electrode.

22. A method for the preparation of an organic light emitting electrochemical fiber cell (OLEFC) comprising:
 a) cleaning of a fiber core;
 b) deposition of an outer electrode by conformal evaporation of a metal, or as a coating from a solution or formulation that includes a conductive material, by dip-coating or spray coating;
 c) deposition of a light emitting layer (EML) as a coating from a solution or formulation that includes at least one organic electroluminescent compound and at least one ionic species of formula $(K^{n+})_a(A^{m-})_b$, wherein $K^+$ is a cation, $A^-$ is an anion, and either $K^+$ or $A^-$ is an organic emissive material, where n, m, a and b are independently selected from the integers 1, 2 or 3, and $n*a-m*b=0$, by dip-coating or spray coating;
 d) deposition of the radiation transmissive electrode.

23. An organic light emitting electrochemical fiber cell (OLEFC) that includes an organic electrochemical cell comprising;
 a fiber core that is flexible or rigid, wherein the fiber core includes an outer electrode, an emissive layer (EML) that includes at least one organic electroluminescent compound and at least one ionic specie of formula $(K^{n+})_a (A^{m-})_b$, wherein $K^+$ is a cation, $A^-$ is an anion, and either $K^+$ or $A^-$ is an organic emissive material, where n, m, a and b are independently selected from the integers 1, 2 or 3, and $n*a-m*b=0$, and the EML is positioned over an outer surface of the outer electrode,
 a radiation transmissive electrode positioned over the EML, and
 at least one organic electroluminescent compound selected from the group consisting of a fluorescent emitter material, a phosphorescent emitter material, and an emissive organo metallic complex.

24. The OLEFC according to claim 23, wherein the EML includes at least one ionic transition-metal complex (iTMC).

* * * * *